US011584935B2

(12) United States Patent
Serafini et al.

(10) Patent No.: US 11,584,935 B2
(45) Date of Patent: Feb. 21, 2023

(54) MATERIALS AND METHODS FOR THE DELIVERY OF THERAPEUTIC NUCLEIC ACIDS TO TISSUES

(71) Applicant: UNIVERSITY OF MIAMI, Miami, FL (US)

(72) Inventors: Paolo Serafini, Miami Shores, FL (US); Dimitri Van Simaeys, Miami Beach, FL (US); Adriana De La Fuente, Miami, FL (US); Alessia Zoso, Miami Shores, FL (US); Silvio Bicciato, Modena (IT); Jimmy Caroli, Modena (IT); Cristian Taccioli, Legnaro (IT); Andrea Grilli, Modena (IT); Midhat Abdulreda, Hialeah Gardens, FL (US)

(73) Assignees: UNIVERSITY OF MIAMI, Miami, FL (US); UNIVERSITY OF MODENA AND REGGIO EMILLA—UNIMORE, Modena (IT)

( * ) Notice: Subject to any disclaimer, the term of this patent is extended or adjusted under 35 U.S.C. 154(b) by 0 days.

(21) Appl. No.: 17/053,193

(22) PCT Filed: May 8, 2019

(86) PCT No.: PCT/US2019/031346
§ 371 (c)(1),
(2) Date: Nov. 5, 2020

(87) PCT Pub. No.: WO2019/217571
PCT Pub. Date: Nov. 14, 2019

(65) Prior Publication Data
US 2021/0139907 A1 May 13, 2021

Related U.S. Application Data

(60) Provisional application No. 62/668,463, filed on May 8, 2018.

(51) Int. Cl.
| | | |
|---|---|---|
| *C12N 15/115* | (2010.01) | |
| *C12N 15/113* | (2010.01) | |
| *A61P 37/06* | (2006.01) | |
| *A61P 3/10* | (2006.01) | |
| *G01N 33/50* | (2006.01) | |
| *G01N 33/566* | (2006.01) | |
| *A61K 48/00* | (2006.01) | |

(52) U.S. Cl.
CPC .............. *C12N 15/115* (2013.01); *A61P 3/10* (2018.01); *A61P 37/06* (2018.01); *C12N 15/113* (2013.01); *G01N 33/507* (2013.01); *G01N 33/566* (2013.01); *A61K 48/00* (2013.01); *C12N 2310/16* (2013.01); *C12N 2310/3519* (2013.01)

(58) Field of Classification Search
None
See application file for complete search history.

(56) References Cited

U.S. PATENT DOCUMENTS

| | | | |
|---|---|---|---|
| 2004/0258619 A1 | 12/2004 | Archer et al. | |
| 2010/0322850 A1 | 12/2010 | Eizirik et al. | |
| 2013/0289258 A1* | 10/2013 | Saetrom | ................... A61P 3/10 536/23.1 |
| 2015/0315573 A1* | 11/2015 | Monteleone | ......... A61K 9/0019 514/44 A |

FOREIGN PATENT DOCUMENTS

| | | |
|---|---|---|
| WO | 2010/042697 A1 | 4/2010 |
| WO | 2014/193800 A2 | 12/2014 |
| WO | 2019/217571 A1 | 11/2019 |

OTHER PUBLICATIONS

Berezhony et al. Molecular Therapy—Nucleic Acids e51: 1, pp. 1-8 (Year: 2012).*
TMED6 transmembrane p24 trafficking protein 6-Gene-NCBI Gene ID: 146456, retrieved on-line Aug. 15, 2022, pp. 1-8 (Year: 2022).*
Mehta et al., Practical management of hyperinsulinism in infancy, Archives of disease in childhood. Fetal and neonatal edition, 84(3):F218 (2001).
Meier et al., Sustained beta cell apoptosis in patients with long-standing type 1 diabetes: indirect evidence for islet regeneration?, Diabetologia, 48(11):2221-2228 (2005).
Meng et al., Small activating RNA binds to the genomic target site in a seed-region-dependent manner, Nucleic Acids Research, 44(5):2274-2282 (2016).
Menni et al., Neurologic outcomes of 90 neonates and infants with persistent hyperinsulinemic hypoglycemia, Pediatrics, 107(3):476-479 (2001).
Miska et al., Real-time immune cell interactions in target tissue during autoimmune-induced damage and graft tolerance, J. Exp. Med., 211(3):441-456 (2014).
Mukherjee et al., HIV sequence variation associated with env antisense adoptive T-cell therapy in the hNSG mouse model, Mol. Ther., 18(4):803-811 (2010).
Nakata et al., Potent anti-R5 human immunodeficiency virus type 1 effects of a CCR5 antagonist, AK602/ONO4128/GW873140, in a novel human peripheral blood mononuclear cell nonobese diabetic-SCID, interleukin-2 receptor gamma-chain-knocked-out AIDS mouse model, J. Virol., 79(4):2087-2096 (2005).
Neff et al., An aptamer-siRNA chimera suppresses HIV-1 viral loads and protects from helper CD4(+) T cell decline in humanized mice, Science translational medicine, 3(66):66ra66 (2011).
Ng et al., Pegaptanib, a targeted anti-VEGF aptamer for ocular vascular disease, Nat. Rev. Drug. Discov., 5(2):123-132 (2006).

(Continued)

*Primary Examiner* — Brian Whiteman
(74) *Attorney, Agent, or Firm* — Marshall, Gerstein & Borun LLP

(57) ABSTRACT

The present disclosure provides materials and methods for the delivery of therapeutic nucleic cells (and imaging agents) to tissues.

10 Claims, 36 Drawing Sheets

Specification includes a Sequence Listing.

(56) References Cited

OTHER PUBLICATIONS

Oram et al., The majority of patients with long-duration type 1 diabetes are insulin microsecretors and have functioning beta cells, Diabetologia., 57(1):187-191 (2014).
Pan et al., Inactivation of tumor suppressor gene HIC1 in gastric cancer is reversed via small activating RNAs, Gene., 527(1):102-108 (2013).
Parashar, Aptamers in Therapeutics, J. Clin. Diagn. Res., 10(6):Be01-06 (2016).
Pardoll et al., Cancer and the Immune System: Basic Concepts and Targets for Intervention, Semin. Oncol., 42(4):523-538 (2015).
Pastor et al., Induction of tumour immunity by targeted inhibition of nonsense-mediated mRNA decay, Nature, 465:227-230 (2010).
Pizarro et al., PD-L1 gene polymorphisms and low serum level of PD-L1 protein are associated to type 1 diabetes in Chile, Diabetes/metabolism research and reviews, 30(8):761-766 (2014).
Plesner et al., The X-linked inhibitor of apoptosis protein enhances survival of murine islet allografts, Diabetes, 54(9):2533-2540 (2005).
Potter et al., Death and dysfunction of transplanted β-cells: lessons learned from type 2 diabetes?, Diabetes, 63(1):12-19 (2014).
Qin et al., RNAa-mediated overexpression of WT1 induces apoptosis in HepG2 cells, World journal of surgical oncology, 10:11 (2012).
Qu et al., Aptamer and its applications in neurodegenerative diseases, Cell Mol. Life Sci., 74(4):683-695 (2016).
Rajesh et al., Th1 and Th17 immunocompetence in humanized NOD/SCID/IL2rgammanull mice, Hum Immunol., 71(6):551-559 (2010).
Ren et al., Targeted induction of endogenous NKX3-1 by small activating RNA inhibits prostate tumor growth, Prostate, 73(14):1591-1601 (2013).
Richardson et al., Islet cell hyperexpression of HLA class I antigens: a defining feature in type 1 diabetes, Diabetologia., 59(11):2448-2458 (2016).
Roep, Insulitis Revisited, Diabetes, 65(3):545-547 (2016).
Rojas et al., Pancreatic beta cell death: Novel potential mechanisms in diabetes therapy, Journal of Diabetes Research, Article ID 9601801 (2018).
Rother et al., Effects of exenatide alone and in combination with daclizumab on beta-cell function in long-standing type 1 diabetes, Diabetes Care, 32(12):2251-2257 (2009).
Sakurai et al., Upregulation of RECK gene expression by small double-stranded RNA targeting the promoter region, Cancer Gene Ther., 21(4):164-170 (2014).
Sato et al., Dynamics of memory and naive CD8+ T lymphocytes in humanized NOD/SCID/IL-2Rgammanull mice infected with CCR5-tropic HIV-1, Vaccine, 28 Suppl 2:B32-37 (2010).
Schwartz et al., Antisense transcripts are targets for activating small RNAs, Nature structural & molecular biology, 15(8):842-848 (2008).
Serafini et al., High-dose granulocyte-macrophage colony-stimulating factor-producing vaccines impair the immune response through the recruitment of myeloid suppressor cells, Cancer Res., 64(17):6337-6343 (2004).
Shapiro et al., Clinical pancreatic islet transplantation, Nat. Rev. Endocrinol., 13(5):268-277 (2016).
Shapiro et al., Combination therapy with low dose sirolimus and tacrolimus is synergistic in preventing spontaneous and recurrent autoimmune diabetes in non-obese diabetic mice, Diabetologia, 45(2):224-230 (2002).
Shultz et al., Human lymphoid and myeloid cell development in NOD/LtSz-scid IL2R gamma null mice engrafted with mobilized human hemopoietic stem cells, J. Immunol., 174(10):6477-6489 (2005).
Song et al., CD4 aptamer-ROR?t shRNA chimera inhibits IL-17 synthesis by human CD4(+) T cells, Biochem Biophys Res. Commun., 452(4):1040-1045 (2014).
Strbo et al., Secreted heat shock protein gp96-Ig: an innovative vaccine approach, Am. J. Reprod. Immunol., 59(5):407-416 (2008).
Subramanian et al., Nucleic acid therapeutics, (2015).
Sullenger et al., From the RNA world to the clinic, Science, 352:1417-1420 (2016).
Taghdisi et al., Targeted delivery of daunorubicin to T-cell acute lymphoblastic leukemia by aptamer, J. Drug. Target., 18(4):277-281 (2010).
Thiel et al., Rapid identification of cell-specific, internalizing RNA aptamers with bioinformatics analyses of a cell-based aptamer selection, PLoS One, 7(9):e43836 (2012).
Thomas et al., Progress and problems with the use of viral vectors for gene therapy, Nat. Rev. Genet., 4(5):346-358 (2003).
Turley et al., Physiological beta cell death triggers priming of self-reactive T cells by dendritic cells in a type-1 diabetes model, The Journal of Experimental Medicine, 198(10):1527-1537 (2003).
Turner et al., Autoregulation of lin-4 microRNA transcription by RNA activation (RNAa) in C. elegans, Cell Cycle, 13(5):772-781 (2014).
Ulrich et al., RNA and DNA aptamers in cytomics analysis, Cytometry A., 59(2):220-231 (2004).
Vanbuecken et al., Residual C-peptide in type 1 diabetes: what do we really know?, Pediatric diabetes, 15(2):84-90 (2014).
Vater et al., A mixed mirror-image DNA/RNA aptamer inhibits glucagon and acutely improves glucose tolerance in models of type 1 and type 2 diabetes, The Journal of Biological Chemistry, 288(29):21136-21147 (2013).
Viste et al., Primary nonfunction of pancreatic islet allografts in different rat strains, Transplant Proc., 22(2):808-809 (1990).
Wang et al., Induction of NANOG expression by targeting promoter sequence with small activating RNA antagonizes retinoic acid-induced differentiation, Biochem. J., 443(3):821-828 (2012).
Wang et al., Persistence of prolonged C-peptide production in type 1 diabetes as measured with an ultrasensitive C-peptide assay, Diabetes Care, 35(3):465-470 (2012).
Wang et al., Prognostic value and function of KLF4 in prostate cancer: RNAa and vector-mediated overexpression identify KLF4 as an inhibitor of tumor cell growth and migration, Cancer Res., 70(24):10182-10191 (2010).
Wang et al., Protective role of programmed death 1 ligand 1 (PD-L1)in nonobese diabetic mice: the paradox in transgenic models, Diabetes, 57(7):1861-1869 (2008).
Watanabe et al., Hematopoietic stem cell-engrafted NOD/SCID/IL2Rgamma null mice develop human lymphoid systems and induce long-lasting HIV-1 infection with specific humoral immune responses, Blood, 109(1):212-218 (2007).
Gu et al., Precise engineering of targeted nanoparticles by using self-assembled biointegrated block copolymers, Proc. Natl. Acad. Sci. USA, 105(7):2586-2591 (2008).
Guo et al., RNAa in action: from the exception to the norm, RNA biology, 11(10):1221-1225 (2014).
Guo et al., Specific delivery of therapeutic RNAs to cancer cells via the dimerization mechanism of phi29 motor pRNA, Hum. Gene. Ther., 16(9):1097-1109 (2005).
Guo, RNA nanotechnology: engineering, assembly and applications in detection, gene delivery and therapy, J. Nanosci. Nanotechnol., 5(12):1964-1982 (2005).
Hanayama et al., Efficient Gene Transduction of Dispersed Islet Cells in Culture Using Fiber-Modified Adenoviral Vectors, Cell Medicine, 8(1-2):31-38 (2015).
Hao et al., Efficient delivery of micro RNA to bone-metastatic prostate tumors by using aptamer-conjugated atelocollagen in vitro and in vivo, Drug delivery, 23(3):864-871 (2016).
Herrmann et al., CTLA4 aptamer delivers STAT3 siRNA to tumor-associated and malignant T cells, J. Clin. Invest., 124(7):2977-2987 (2014).
Hu et al., Inhibition of monocyte adhesion to brain-derived endothelial cells by dual functional RNA chimeras, Nucleic acids, 3(11):e209 (2014).
Hu, Recent Advances in Aptamers Targeting Immune System, Inflammation, 40(1):295-302 (2016).
Huang et al., Cancer cell targeting using multiple aptamers conjugated on nanorods, Anal. Chem., 80(3):567-572 (2008).
Huang et al., Molecular assembly of an aptamer-drug conjugate for targeted drug delivery to tumor cells, Chembiochem., 10(5):862-868 (2009).

(56) References Cited

OTHER PUBLICATIONS

Huang et al., RNAa is conserved in mammalian cells, PLoS One, 5(1):e8848 (2010).
Hughes et al., Gene therapy to improve pancreatic islet transplantation for Type 1 diabetes mellitus, Current diabetes reviews, 6(5):274-284 (2010).
Hughes et al., Precipitation of autoimmune diabetes with anti-PD-1 immunotherapy, Diabetes Care, 38(4):e55-57 (2015).
Hughes et al., Targeted Therapy and Checkpoint Immunotherapy Combinations for the Treatment of Cancer, Trends Immunol., 37(7):462-476 (2016).
Hui et al., Role of caspases in the regulation of apoptotic pancreatic islet beta-cells death, Journal of Cellular Physiology, 200(2):177-200 (2004).
International Application No. PCT/US19/31346, Invitation to Pay Additional Fees, dated Jul. 18, 2019.
International Application No. PCT/US19/31346, International Preliminary Report on Patentability, dated Nov. 19, 2020.
International Application No. PCT/US19/31346, International Search Report and Written Opinion, dated Sep. 13, 2019.
Ishikawa et al., Development of functional human blood and immune systems in NOD/SCID/IL2 receptor {gamma} chain(null) mice, Blood, 106(5):1565-1573 (2005).
Ito et al., NOD/SCID/gamma(c)(null) mouse: an excellent recipient mouse model for engraftment of human cells, Blood, 100(9):3175-3182 (2002).
Janowski et al., Activating gene expression in mammalian cells with promoter-targeted duplex RNAs, Nature chemical biology, 3(3):166-173 (2007).
Javier et al., Aptamer-targeted gold nanoparticles as molecular-specific contrast agents for reflectance imaging, Bioconjug Chem., 19(6):1309-1312 (2008).
Jimenez-Moreno et al., A Simple High Efficiency Intra-Islet Transduction Protocol Using Lentiviral Vectors, Curr. Gene. Ther., 15(4):436-446 (2015).
Joseph et al., Inhibition of in vivo HIV infection in humanized mice by gene therapy of human hematopoietic stem cells with a lentiviral vector encoding a broadly neutralizing anti-HIV antibody, J. Virol., 84(13):6645-6653 (2010).
Kang et al., A liposome-based nanostructure for aptamer directed delivery, Chem. Commun (Camb), 46(2):249-251 (2010).
Kanwar et al., Nucleic acid-based aptamers: applications, development and clinical trials, Current medicinal chemistry, 22(21):2539-2557 (2015).
Kassem et al., p57(KIP2) expression in normal islet cells and in hyperinsulinism of infancy, Diabetes, 50(12):2763-9 (2001).
Keenan et al., Residual insulin production and pancreatic β-cell turnover after 50 years of diabetes: Joslin Medalist Study, Diabetes, 59(11):2846-2853 (2010).
Keir et al., PD-1 regulates self-reactive CD8+ T cell responses to antigen in lymph nodes and tissues, J. Immunol., 179(8):5064-5070 (2007).
Kosaka et al., Targeted p21WAF1/CIP1 activation by RNAa inhibits hepatocellular carcinoma cells, Nucleic acid therapeutics, 22(5):335-343 (2012).
Kumar et al., T cell-specific siRNA delivery suppresses HIV-1 infection in humanized mice, Cell, 134(4):577-586 (2008).
Lai et al., Synergistic inhibition of lung cancer cell invasion, tumor growth and angiogenesis using aptamer-siRNA chimeras, Biomaterials, 35(9):2905-2914 (2014).
Lao et al., Aptamer nanomedicine for cancer therapeutics: barriers and potential for translation, ACS nano, 9(3):2235-2254 (2015).
Lazard et al., Induction of beta-cell resistance to hypoxia and technologies for oxygen delivery to transplanted pancreatic islets, Diabetes/metabolism research and reviews, 28(6):475-484 (2012).
Lee et al., Blocking the monocyte chemoattractant protein-1/CCR2 chemokine pathway induces permanent survival of islet allografts through a programmed death-1 ligand-1-dependent mechanism, J. Immunol., 171(12):6929-6935 (2003).
Lee et al., Therapeutic aptamers: developmental potential as anti-cancer drugs, BMB reports, 48(4):234-237 (2015).
Lepus et al., Comparison of human fetal liver, umbilical cord blood, and adult blood hematopoietic stem cell engraftment in NOD-scid/gammac-/-, Balb/c-Rag1-/-gammac-/-, and C.B-17-scid/bg immunodeficient mice, Hum. Immunol., 70(10):790-802 (2009).
Li et al., Directed evolution of gold nanoparticle delivery to cells, Chem. Commun (Camb), 46(3):392-394 (2010).
Li et al., PD-L1-driven tolerance protects neurogenin3-induced islet neogenesis to reverse established type 1 diabetes in NOD mice, Diabetes, 64(2):529-540 (2015).
Li et al., Small dsRNAs induce transcriptional activation in human cells, Proc. Natl. Acad. Sci. USA, 103(46):17337-17342 (2006).
Liu et al.,Pancreatic beta cell function persists in many patients with chronic type 1 diabetes, but is not dramatically improved by prolonged immunosuppression and euglycaemia from a beta cell allograft, Diabetologia., 52(7):1369-1380 (2009).
Llegems et al., Reporter islets in the eye reveal the plasticity of the endocrine pancreas, Proc. Natl. Acad. Sci. USA, 110(51):20581-6 (2013).
Loiler et al., Targeting recombinant adeno-associated virus vectors to enhance gene transfer to pancreatic islets and liver, Gene. Ther., 10(18):1551-1558 (2003).
Lonlay et al., Somatic deletion of the imprinted 11p15 region in sporadic persistent hyperinsulinemic hypoglycemia of infancy is specific of focal adenomatous hyperplasia and endorses partial pancreatectomy, J. Clin. Invest., 100(4):802-807 (1997).
Magalhaes et al., A general RNA motif for cellular transfection, Mol. Ther., 20(3):616-624 (2012).
Mathis et al., beta-Cell death during progression to diabetes, Nature, 414:792-798 (2001).
Mazurier et al., A novel immunodeficient mouse model—RAG2 x common cytokine receptor gamma chain double mutants—requiring exogenous cytokine administration for human hematopoietic stem cell engraftment, J. Interferon Cytokine Res., 19(5):533-541 (1999).
Mcnamara et al., Cell type-specific delivery of siRNAs with aptamer-siRNA chimeras, Nat. Biotechnol., 24(8):1005-1015 (2006).
Mehrotra et al., Short interfering RNA therapeutics: nanocarriers, prospects and limitations, JET Nanobiotechnology, 9(6):386-395 (2015).
Weinberg et al., An RNA targeted to the HIV-1 LTR promoter modulates indiscriminate off-target gene activation, Nucleic Acids Res., 35(21):7303-7312 (2007).
Weir et al., Finally! A human pancreatic β cell line, The Journal of Clinical Investigation, 121(9):3395-3397 (2011).
Wheeler et al., Durable knockdown and protection from HIV transmission in humanized mice treated with gel-formulated CD4 aptamer-siRNA chimeras, Mol. Ther., 21(7):1378-1389 (2013).
Wheeler et al., Inhibition of HIV transmission in human cervicovaginal explants and humanized mice using CD4 aptamer-siRNA chimeras, J. Clin. Invest., 121(6):2401-2412 (2011).
Woodruff et al., Modulation of the Coagulation Cascade Using Aptamers, Arteriosclerosis, thrombosis, and vascular biology, 35(10):2083-2091 (2015).
Wu et al., XIAP gene expression protects β-cells and human islets from apoptotic cell death, Mol. Pharm., 7(5):1655-1666 (2010).
Wullner et al., Cell-specific induction of apoptosis by rationally designed bivalent aptamer-siRNA transcripts silencing eukaryotic elongation factor 2, Curr. Cancer Drug Targets, 8(7):554-565 (2008).
Yang et al., Glucose-modulated transgene expression via recombinant adeno-associated virus, Pharm. Res., 19(7):968-975 (2002).
Yang et al., Human beta cells are exceedingly resistant to streptozotocin in vivo, Endocrinology, 143(7):2491-2495 (2002).
Yang et al., Promoter-targeted double-stranded small RNAs activate PAWR gene expression in human cancer cells, Int. J. Biochem. Cell Biol., 45(7):1338-1346 (2013).
Yu et al., Molecular Selection, Modification and Development of Therapeutic Oligonucleotide Aptamers, International journal of molecular sciences, 17(3):358 (2016).
Zhang et al., Co-delivery of hydrophobic and hydrophilic drugs from nanoparticle-aptamer bioconjugates, ChemMedChem, 2(9):1268-1271 (2007).

(56) References Cited

OTHER PUBLICATIONS

Zhang et al., Proteomic profiling of human islets collected from frozen pancreata using laser capture microdissection, J. Proteomics, 150:149-159 (2017).
Zheng et al., RNA activation: promise as a new weapon against cancer, Cancer Lett., 355(1):18-24 (2014).
Zhou et al., Current progress of RNA aptamer-based therapeutics, Front. Genet., 3:234 (2012).
Zhou et al., Functional in vivo delivery of multiplexed anti-HIV-1 siRNAs via a chemically synthesized aptamer with a sticky bridge, Mol. Ther., 21(1):192-200 (2013).
Zhou et al., Methods for assembling B-cell lymphoma specific and internalizing aptamer-siRNA nanoparticles via the sticky bridge, Methods Mol. Biol., 1297:169-185 (2015).
Zhou et al., Novel dual inhibitory function aptamer-siRNA delivery system for HIV-1 therapy, Mol. Ther., 16(8):1481-1489 (2008).
Zhou et al., The therapeutic potential of cell-internalizing aptamersm, Curr. Top Med. Chem., 9(12):1144-1157 (2009).
Zhu et al., Nucleic acid aptamers: an emerging frontier in cancer therapy, Chem. Commun (Camb), 48(85):10472-10480 (2012).
Abdulreda et al., High-resolution, noninvasive longitudinal live imaging of immune responses, Proc. Natl. Acad. Sci. USA, 108(31):12863-12868 (2011).
Abdulreda et al., Transplantation into the anterior chamber of the eye for longitudinal, non-invasive in vivo imaging with single-cell resolution in real-time, J. Vis. Exp., (73):e50466 (2013).
Abe et al., Folia pharmacologica Japonica, 147:362-367, doi:10.1254/fpj.147.362 (2016).
Akkina et al., Humanized Rag1-/- ?c-/- mice support multilineage hematopoiesis and are susceptible to HIV-1 infection via systemic and vaginal routes, PLoS One, 6(6):e20169 (2011).
Alagia et al., siRNA and RNAi optimization, Wiley interdisciplinary reviews RNA, 7(3):316-29 (2016).
Almaca et al., Young capillary vessels rejuvenate aged pancreatic islets, Proc. Natl Acad. Sci. USA, 111(49):17612-7 (2014).
Ansari et al., The programmed death-1 (PD-1) pathway regulates autoimmune diabetes in nonobese diabetic (NOD) mice, J. Exp. Med., 198(1):63-69 (2003).
Avrahami et al., Targeting the cell cycle inhibitor p57Kip2 promotes adult human β cell replication, J. Clin. Invest., 124(2):670-674 (2014).
Bagalkot et al., An aptamer-doxorubicin physical conjugate as a novel targeted drug-delivery platform, Angew. Chem. Int. Ed. Engl., 45(48):8149-8152 (2006).
Bain et al., An adenovirus vector for efficient RNA interference-mediated suppression of target genes in insulinoma cells and pancreatic islets of langerhans, Diabetes, 53(9):2190-2194 (2004).
Bandello et al., Anti-VEGF Molecules for the Management of Diabetic Macular Edema, Current pharmaceutical design, 21(32):4731-4737 (2015).
Becker et al., Overexpression of hexokinase I in isolated islets of Langerhans via recombinant adenovirus. Enhancement of glucose metabolism and insulin secretion at basal but not stimulatory glucose levels, J. Biol. Chem., 269(33):21234-21238 (1994).
Bellin et al., Total pancreatectomy with islet autotransplantation: summary of an NIDDK workshop, Ann. Surg., 261(1):21-29 (2015).
Benazra et al., A human beta cell line with drug inducible excision of immortalizing transgenes, Molecular metabolism, 4(12):916-925 (2015).
Berges et al., Mucosal transmission of R5 and X4 tropic HIV-1 via vaginal and rectal routes in humanized Rag2-/-gammac -/- (RAG-hu) mice, Virology, 373(2):342-351 (2008).
Berman et al., Bioengineering the Endocrine Pancreas: Intraomental Islet Transplantation Within a Biologic Resorbable Scaffold, Diabetes, 65(5):1350-1361 (2016).
Borrello et al., Granulocyte-macrophage colony-stimulating factor (GM-CSF)-secreting cellular immunotherapy in combination with autologous stem cell transplantation (ASCT) as postremission therapy for acute myeloid leukemia (AML), Blood 114(9):1736-45 (2009).

Borriello et al., p57(Kip2) and cancer: time for a critical appraisal, Molecular Cancer Research, 9(10):1269-1284 (2011).
Bottino et al., Gene- and cell-based therapeutics for type I diabetes mellitus, Gene Ther., 10(10):875-889 (2003).
Brainard et al., Induction of robust cellular and humoral virus-specific adaptive immune responses in human immunodeficiency virus-infected humanized BLT mice, Virol., 83(14):7305-7321 (2009).
Brehm et al., Advancing animal models of human type 1 diabetes by engraftment of functional human tissues in immunodeficient mice, Cold Spring Harbor Perspectives in Medicine, 2(5):a007757 (2012).
Brehm et al., Parameters for establishing humanized mouse models to study human immunity: analysis of human hematopoietic stem cell engraftment in three immunodeficient strains of mice bearing the IL2rgamma(null) mutation, Clin. Immunol., 135(1):84-98 (2010).
Bruno, Predicting the Uncertain Future of Aptamer-Based Diagnostics and Therapeutics, Molecules, 20(4):6866-6887 (2015).
Butler et al., Modestly increased beta cell apoptosis but no increased beta cell replication in recent-onset type 1 diabetic patients who died of diabetic ketoacidosis, Diabetologia., 50(11):2323-2331 (2007).
Camorani et al., Oligonucleotide aptamers for glioma targeting: an update, Central nervous system agents in medicinal chemistry, 15(2):126-137 (2015).
Cao et al., Reversible cell-specific drug delivery with aptamer-functionalized liposomes, Angew. Chem. Int. Ed. Engl., 48(35):6494-6498 (2009).
Caroli et al., APTANI: a computational tool to select aptamers through sequence-structure motif analysis of HT-SELEX data, Bioinformatics, 32(2):161-164 (2016).
Chen et al., Antitumor effect of dsRNA-induced p21(WAF1/CIP1) gene activation in human bladder cancer cells, Mol. Cancer Ther., 7(3):698-703 (2008).
Chen et al., Up-regulation of VEGF by small activator RNA in human corpus cavernosum smooth muscle cells, The journal of sexual medicine, 8(10):2773-2780 (2011).
Chu et al., Aptamer mediated siRNA delivery, Nucleic Acids Res., 34(10):e73 (2006).
Chu et al., Involvement of argonaute proteins in gene silencing and activation by RNAs complementary to a non-coding transcript at the progesterone receptor promoter, Nucleic Acids Res., 38(21):7736-7748 (2010).
Dassie et al., Systemic administration of optimized aptamer-siRNA chimeras promotes regression of PSMA-expressing tumors, Nat. Biotechnol., 27(9):839-849 (2009).
Deng et al., NK cells, macrophages, and humoral immune responses are dominant in primary nonfunction of islet grafts in the dog-to-rat xenotransplant model, Transplant Proc., 29(4):2062-2063 (1997).
Dhar et al., Targeted delivery of cisplatin to prostate cancer cells by aptamer functionalized Pt(IV) prodrug-PLGA-PEG nanoparticles, Proc. Natl. Acad. Sci. USA, 105(45):17356-17361 (2008).
Diiorio et al., Hyperglycemia-induced proliferation of adult human beta cells engrafted into spontaneously diabetic immunodeficient NOD-Rag1null IL2r?null Ins2Akita mice, Pancreas, 40(7):1147-1149 (2011).
Donath et al., Mechanisms of beta-cell death in type 2 diabetes, Diabetes, 54 Suppl 2:S108-13 (2005).
Dong et al., Small double-stranded RNA mediates the anti-cancer effects of p21WAF1/CIP1 transcriptional activation in a human glioma cell line, Yonsei. Med. J., 55(2):324-330 (2014).
Emamaullee et al., XIAP overexpression in human islets prevents early posttransplant apoptosis and reduces the islet mass needed to treat diabetes, Diabetes, 54(9):2541-2548 (2005).
Emamaullee et al., XIAP overexpression in islet beta-cells enhances engraftment and minimizes hypoxia-reperfusion injury, Am. J. Transplant., 5(6):1297-1305 (2005).
Farokhzad et al., Nanoparticle-aptamer bioconjugates: a new approach for targeting prostate cancer cells, Cancer Research, 64(21):7668-7672 (2004).
Farokhzad et al., Targeted nanoparticle-aptamer bioconjugates for cancer chemotherapy in vivo, Proc. Natl. Acad. Sci. USA, 103(16):6315-6320 (2006).
Flotte et al., Efficient ex vivo transduction of pancreatic islet cells with recombinant adeno-associated virus vectors, Diabetes, 50(3):515-520 (2001).

(56) References Cited

OTHER PUBLICATIONS

Francisco et al., The PD-1 pathway in tolerance and autoimmunity, Immunological reviews, 236:219-242 (2010).
Giannelli et al., A six-color flow cytometric assay for the analysis of peripheral blood dendritic cells, Cytometry B. Clin. Cytom., 74(6):349-355 (2008).
Giannoukakis et al., Gene therapy for type 1 diabetes, American journal of therapeutics, 12(6):512-528 (2005).
Gilboa-Geffen et al., Gene Knockdown by EpCAM Aptamer-siRNA Chimeras Suppresses Epithelial Breast Cancers and Their Tumor-Initiating Cells, Mol. Cancer Ther., 14(10):2279-2291 (2015).
Goldman et al., Enhanced human cell engraftment in mice deficient in RAG2 and the common cytokine receptor gamma chain, Br. J. Haematol., 103(2):335-342 (1998).
Gonzalez et al., Humanized mice: novel model for studying mechanisms of human immune-based therapies, Immunol. Res., 57(1-3):326-334 (2013).
Gorantla et al., CD8+ cell depletion accelerates HIV-1 immunopathology in humanized mice, J. Immunol., 184(12):7082-7091 (2010).
Gorantla et al., Human dendritic cells transduced with herpes simplex virus amplicons encoding human immunodeficiency virus type 1 (HIV-1) gp120 elicit adaptive immune responses from human cells engrafted into NOD/SCID mice and confer partial protection against HIV-1 challenge, J. Virol., 79(4):2124-2132 (2005).

\* cited by examiner

8 Cycle In Mouse +
1 Cycle In Human

9 Cycle In Mouse

Irrelevant Aptamer screening of 15 monoclonal antibodies identifies 10 monoclonal aptamer that preferentially recognize human islets human tissues array using aptamer 1-717 as probe

| adrenal | bone marrow | breast | brain cerebellum | brain cortex |
| brain pituary | colon | endothelium arthery | esophagus | fallopian Tube |
| heart left ventricule | kidney | liver | lung | lymph node |
| ovary | pancreas | placenta | prostate | skin |
| spinal cord | speen | striated muscle | stomach | testis |
| thymus | thyroid | Ureter | Uterus | cervix |

FIG. 5A human tissues array using aptamer m12-3773 as probe

FIG. 5B

Table 1: Microarray tissues staining with selected aptamers

| Organ\clone | CTRL | 166-279 | 173-2273 | 107-901 | 1-717 | m1-2623 | n6-3239 | m12-3773 |
|---|---|---|---|---|---|---|---|---|
| Adrenal | + | - | ++ | +++ | - | - | +++ | + |
| Bone marrow | - | - | + | ++ | - | - | ++ | - |
| Breast | - | - | - | + | - | - | + | - |
| Brain cerebrum | - | - | + | ++ | - | - | ++ | - |
| Brain Cerebral cortex | + | + | + | +++ | - | ++ | +++ | - |
| Brain pituary | + | + | + | +++ | - | ++ | +++ | - |
| Colon | + | - | - | + | - | - | + | - |
| Endothelium/artery | ++ | + | + | +++ | - | +++ | +++ | + |
| Esophagus | - | - | - | ++ | - | - | ++ | - |
| Fallopian Tube | ++ | - | ++ | ++ | - | - | ++ | - |
| Heart/left ventricule | ++ | - | + | +++ | - | +++ | +++ | - |
| Kidney | - | - | - | +++ | - | - | +++ | - |
| Liver | - | + | - | +++ | - | ++ | +++ | - |
| Lung | + | - | - | +++ | - | - | +++ | - |
| Lymph node | - | - | - | + | - | - | + | - |
| Ovary | - | - | - | + | - | - | + | - |
| Placenta | + | ++ | ++ | + | - | ++ | ++ | + |
| Prostate | - | + | ++ | ++ | - | + | + | - |
| Skin | - | - | - | - | - | - | - | +/- |
| Spinal cord | - | ++ | ++ | + | - | + | + | - |
| Spleen | - | ++ | ++ | + | - | - | + | - |
| Striated muscle | - | ++ | ++ | + | - | + | + | - |
| Stomach | - | ++ | - | - | - | - | - | - |
| Testis | +/- | ++ | ++ | ++ | +/- | ++ | ++ | + |
| Thymus | - | - | + | ++ | - | ++ | - | - |
| Thyroid | - | - | - | + | - | ++ | - | - |
| Ureter | - | - | - | ++ | - | - | - | - |
| Uterus | - | - | - | - | - | - | - | - |
| Cervix | - | ++ | - | - | - | - | - | - |
| Pancreas | - | ++ | ++ | ++ | ++ | ++ | ++ | ++ |
| Islets of Langerhans* | - | +++ | ++ | +++ | +++ | - | +++ | +++ |
| Exocrine Glandular cells* | - | - | - | - | +/- | - | - | +/- |

Note: +/- low positivity, ++ positive staining, +++ high staining, ++++ bright staining. In green are the staining over the control are highlighted

FIG. 5C mouse tissues arrays using aptamer

Aptamer 1-717

| Liver | Heart | Stomach | Spleen |
|---|---|---|---|
| Kidney | Skeletal Muscle | Jejunum | Lung |
| Pancreas | Pancreas (Non Islet section) | Testis | Ovary |

Aptamer m12-3773

| Liver | Heart | Stomach | Spleen |
|---|---|---|---|
| Kidney | Skeletal Muscle | Jejunum | Lung |
| Pancreas | Testis | Ovary | |

FIG. 6 aptamer recognize preferentially beta cells

Aptamer M12-3773

Aptamer 1-717

Target Clusterin Mascot score: 265 coverage: 39% isoform 3 (23% isoform 1)

```
>clusterin (P10909)(isoform3 in bold)MQVCS QPQRG
CVREQ SAINT APPSA HNAAS PGGAR GHRVP LTEAC KDSRI
GGMMK TLLLF VGLLL TWESG QVLGD QTVSD NELQE MSNQG
SKYVN KEIQN AVNGV KQIKT LIEKT NEERK TLLSN LEEAK
KKKED ALNET RESET KLKEL PGVCN ETMMA LWEEC KPCLK
QTCMK FYARV CRSGS GLVGR QLEEF LNQSS PFYFW MNGDR
IDSLL ENDRQ QTHML DVMQD HFSRA SSIID ELFQD RFFTR
EPQDT YHILP FSLPH RRPHF FFPKS RIVRS LMPFS PYEPL
NFHAM FQPFL EMIHE AQQAM DIHFH SPAFQ HPPTE FIREG
DDDRT VCREI RHNST GCLRM KDQCD KCREI LSVDC STNNP
SQAKL RRELD ESLQV AERLT RKYNE LLKSY QWKML NTSSL
LEQLN EQFNW VSRLA NLTQG EDQYY LRVTT VASHT SDSDV
PSGVT EVVVK LFDSD PITVT VPVEV SRKNP KFMET VAEKA
LQEYR KKHRE E
```

FIG. 8B

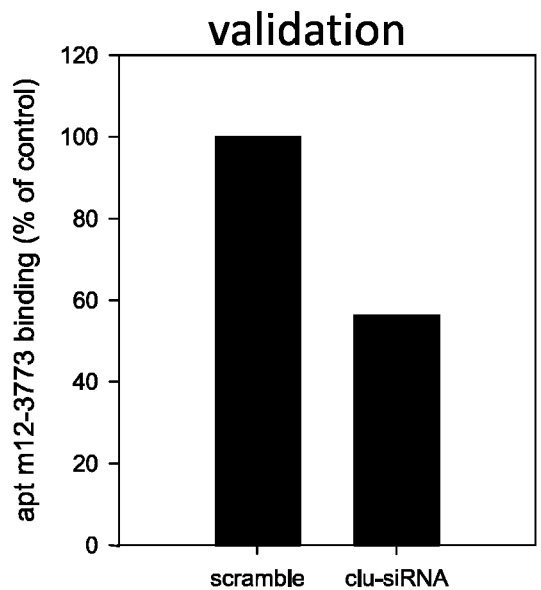

FIG. 8C

| GeneID | RefSeq | Block | Row | Column | Expression Over Control | p-Value | |
|---|---|---|---|---|---|---|---|
| | | | | | | t-Test | FDR |
| TMED6 | NM_144676.1 | 29 | 1 | 17 | 4.00 | 1.84E-02 | 4.05E-01 |
| PRPS1 | NM_002764.2 | 34 | 1 | 1 | 3.92 | 2.02E-02 | 4.05E-01 |
| ACVR1C | NM_145259.1 | 34 | 1 | 3 | 3.67 | 3.63E-02 | 4.21E-01 |
| TBPL1 | NM_004865.2 | 34 | 2 | 17 | 2.36 | 2.62E-02 | 4.05E-01 |
| C11orf74 | BC009561.1 | 32 | 2 | 25 | 1.99 | 4.82E-03 | 3.31E-01 |
| SCAMP1 | NM_004866.4 | 32 | 2 | 3 | 1.95 | 1.35E-02 | 3.86E-01 |
| SERINC1 | BC028607.1 | 24 | 3 | 9 | 1.80 | 1.27E-02 | 3.86E-01 |
| MRPL44 | NM_022915.2 | 8 | 2 | 1 | 1.68 | 6.19E-04 | 3.14E-01 |

FIG. 9B aptamer chimera allow the silencing on genes on non-dissociated islets

In vivo administration of P57kip2siRNA-aptamer chimera induce the proliferation on human beta cells In vivo experiment identification of Xiap-saRNA identification of PDL1-saRNA Bio-informatics analysis of PDL1 promoter PDL1-saRNA/aptamer chimera upregulate PDL1 in vivo
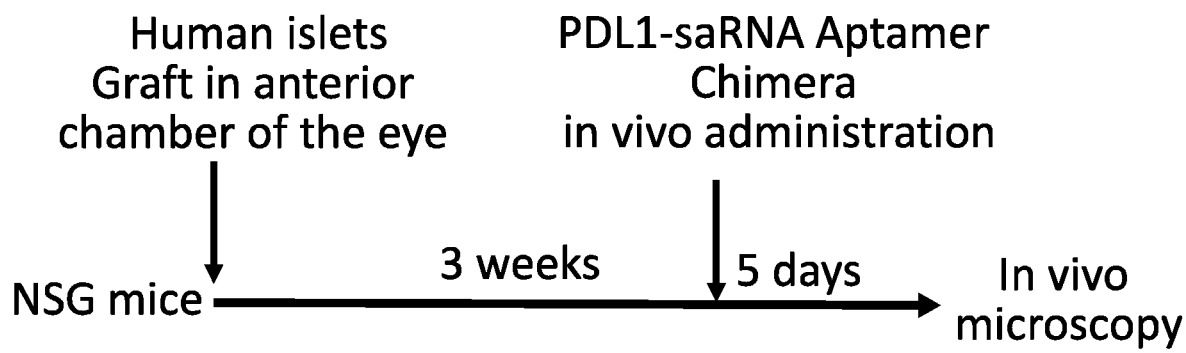
FIG. 20A
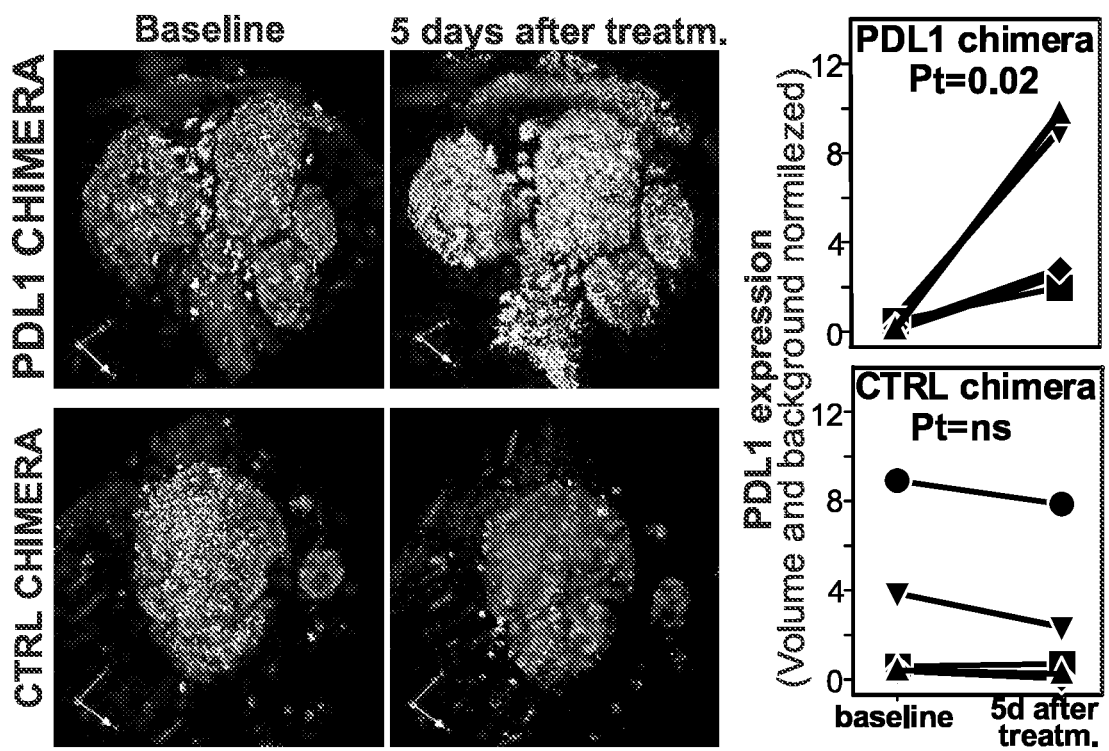
FIG. 20B
FIG. 20C

MATERIALS AND METHODS FOR THE DELIVERY OF THERAPEUTIC NUCLEIC ACIDS TO TISSUES

CROSS-REFERENCE TO RELATED APPLICATIONS

The present application claims the benefit of priority to U.S. Provisional Application No. 62/668,463 filed May 8, 2018, the disclosure of which is incorporated herein by reference in its entirety.

STATEMENT OF GOVERNMENT SUPPORT

This invention was made with government support under grant number DK116241 awarded by the National Institutes of Health. The government has certain rights in the invention.

FIELD OF THE INVENTION

The present disclosure provides materials and methods for the delivery of therapeutic nucleic cells (and imaging agents) to tissues.

INCORPORATION BY REFERENCE OF MATERIALS SUBMITTED ELECTRONICALLY

This application contains, as a separate part of the disclosure, a Sequence Listing in computer readable form (Filename: 53048A_Seqlisting.txt; Size: 116,998 bytes; Created: May 8, 2019), which is incorporated by reference in its entirety.

BACKGROUND

Diabetes is a group of metabolic disorders in which there are high blood sugar levels over a prolonged period caused by the insufficiency of the hormone insulin produced by the pancreatic beta cells. In particular, type 1 diabetes is caused by the progressive autoimmune destruction of beta cells whereas in type 2 diabetes insulin is not produced in quantities sufficient for the body needs. Although for many years the contribution of beta cell loss to type 2 diabetes was debated, in the last decade it became clear that a loss of beta cells is involved also in the pathophysiology of type 2 diabetes (Rojas et al., Journal of Diabetes Research, vol. 2018, Article ID 9601801, 19 pages, 2018; Donath et al., Diabetes. 2005 December; 54 Suppl 2:S108-13). Despite this knowledge to date there are no available methods to directly measure the number of beta cell (beta cell mass) in vivo or to deliver therapeutics specifically to these important cells. Indeed, methods to determine diabetes progression rely mostly on the indirect measurement (i.e the determination of glucose or c-peptide concentration in the blood) and cannot discriminate whether many cells produce little insulin or few cells produce large quantities of this hormone. Thus, these methods cannot measure the progressive beta cell loss in patients with diabetes. The lack of adequate marker specific for beta cell make also impossible to deliver therapeutics specifically to beta cells to halt or reverse beta cell loss.

RNA aptamers have emerged as effective delivery vehicles for siRNAs in the treatment of many human diseases because they actively enhance the intracellular accumulation of therapeutic cargo by receptor-mediated internalization or by clathrin-mediated endocytosis (35-39, 43-74). The use of aptamers to deliver the therapeutic RNA of interest to the β cells offers advantage over the use of viral vectors such for example the transient modulation of the gene of interest, the lack of immunogenicity, and a great safety profile. To date, adenoviral vectors have been mostly used for efficient delivery of genes and siRNA to primary pancreatic islets in vitro (79-84). In vivo, however, beside the technical difficulties in using of viral vectors, their inherent immunogenicity and possible recombination with wild type virus raises serious safety concerns. Indeed, viral vectors can induce strong immune responses with secondary complications that may include multi-organs failure and even death (85). The advent of lentiviral vectors alleviated some of the immunogenicity concerns, but lentiviruses are not as efficient as adenoviruses in transducing intact human islets (86,87); although current in vitro protocols are being optimized88. Nevertheless, lentiviral integration in the genome still raises safety concerns, risks of insertional mutagenesis and recombination with wild type viruses.

SUMMARY

In one aspect, the disclosure provides a method of delivering one or more agents to a tissue comprising contacting the tissue with a construct comprising an aptamer that is specific for the tissue conjugated to the agent. In some embodiments, the tissue is from an organ selected from the group consisting of pancreas, heart, lung, kidney, stomach, skin and brain. In some embodiments, the tissue is pancreatic islets. In some embodiments, the agent is a therapeutic nucleic acid. In some embodiments, the therapeutic nucleic acid is a therapeutic RNA. In some embodiments, the therapeutic RNA is selected from the group consisting of siRNA and saRNA. In some embodiments, the agent is an imaging reagent. Exemplary imaging reagents include, but are not limited to, fluorochromes, Positron emission tomography tracer such as Fluorine-18, oxygen-15, gallium 68, magnetic resonance imaging contrast agents such as gadolinium, iron oxide, iron platinum and manganese. The contacting step can occur in vitro or in vivo.

In another aspect, the disclosure provides a construct comprising an aptamer conjugated to a small activating RNA (saRNA). In some embodiments, the aptamer is specific for human pancreatic islets. In some embodiments, the aptamer is selected from the group consisting of M12-3773 and 1-717.

In some embodiments, the aptamer is specific for clusterin (CLU, gene id 1191). In some embodiments, the aptamer is specific for "Transmembrane emp24 domain-containing protein 6" (TMED6, gene id 146456).

In some embodiments, the tissue is adrenal tissue or bone marrow and the aptamer is 173-2273, 107-901 or m6-3239. In some embodiments, the tissue is breast tissue, lung tissue or lymph node tissue and the aptamer is 107-901 and m6-3239. In some embodiments, the tissue is brain cerebellum and the aptamer is 173-2273, 107-901, m1-2623 or m6-3239. In some embodiments, the tissue is brain cerebral cortex tissue, pituitary tissue, colon tissue, endothelium tissue, esophagus tissue, heart tissue or kidney tissue and the aptamer is 107-901, m1-2623 or m6-3239. In some embodiments, the tissue is fallopian tube tissue and the aptamer is m6-3239. In some embodiments, the tissue is liver tissue and the aptamer is 166-279, 107-901, m1-2623 or m6-3239. In some embodiments, the tissue is ovarian tissue and the aptamer is 107-901. In some embodiments, the tissue is placenta tissue and the aptamer is 166-270, 173-2273, 107-901, m1-2623 or m6-3239. In some embodiments, the tissue is prostate tissue and the aptamer is 173-2273 or 107-901. In some embodiments, the tissue is spinal cord tissue and the aptamer is 166-279 or 173-2273. In some embodiments, the tissue is testis tissue and the aptamer is 166-279, 173-2273, 107-901, m1-2623, m6-3239 and m12-3773. In some embodiments, the tissue is thymus tissue and the aptamer is 173-2273, 107-901 or mf-2623. In some embodiments, the tissue is thyroid tissue and the aptamer is m1-2623. In some embodiments, the tissue is ureter tissue and the aptamer is 107-901. In some embodiments, tissue is cervical tissue and the aptamer is 166-279. In some embodiments, the tissue is islets of Langerhans or pancreatic tissue and the aptamer is 166-279, 173-2273, 107-901, 1-717, m1-2623, m6-3239 or m12-3773.

In another aspect, the disclosure provides a method of delivering one or more agents to pancreatic islets comprising contacting the islets with a construct comprising an aptamer that is specific for islets conjugated to the agent. In some embodiments, the agent is a therapeutic nucleic acid. In some embodiments, the therapeutic nucleic acid is a therapeutic RNA. In some embodiments, the therapeutic RNA is selected from the group consisting of siRNA and saRNA. In some embodiments, the agent is an imaging reagent. Exemplary imaging reagents include, but are not limited to, fluorochromes, Positron emission tomography tracer such as Fluorine-18, oxygen-15, gallium 68, magnetic resonance imaging contrast agents such as gadolinium, iron oxide, iron platinum and manganese. The contacting step can occur in vitro or in vivo.

In some embodiments, the aptamer is selected from the group consisting of M12-3773 and 1-717. In some embodiments, the aptamer is specific for clusterin (CLU, gene id 1191). In some embodiments, the aptamer is specific for "Transmembrane emp24 domain-containing protein 6" (TMED6, gene id 146456).

In another aspect, the disclosure provides a method of measuring beta cell mass comprising contacting the beta cell with a construct comprising an aptamer conjugated to an imaging reagent in an amount effective to measure the mass of the beta cell. In some embodiments, the aptamer is selected from the group consisting of M12-3773 and 1-717. In some embodiments, the imaging reagent is a fluorochrome. In some embodiments, the imaging reagent is a PET tracer. In some embodiments, the imaging reagent is a MRI contrast reagent. In some embodiments, the imaging reagent can be conjugated to the aptamer via chelators.

In another aspect, the disclosure provides a method of modulating proliferation of beta cell comprising contacting the beta cell with a construct comprising an aptamer conjugated to a therapeutic nucleic acid in an amount effective to modulate proliferation of the beta cell. In some embodiments, the aptamer is selected from the group consisting of M12-3773 and 1-717. In some embodiments, the therapeutic nucleic acid is a therapeutic RNA. In some embodiments, the therapeutic RNA is selected from the group consisting of siRNA and saRNA. The contacting step can occur in vitro or in vivo.

In another aspect, the disclosure provides a method for inhibiting beta cell apoptosis comprising contacting the beta cell with a construct comprising an aptamer conjugated to a therapeutic nucleic acid in an amount effective to inhibit apoptosis of the beta cell. In some embodiments, the aptamer is selected from the group consisting of M12-3773 and 1-717. In some embodiments, the therapeutic nucleic acid is a therapeutic RNA. In some embodiments, the therapeutic RNA is selected from the group consisting of siRNA and saRNA. In some embodiments the therapeutic RNA upregulate the protein XIAP (X-linked inhibitor of apoptosis gene id 331). The contacting step can occur in vitro or in vivo.

In another aspect, the disclosure provides a method for inhibiting tissue graft apoptosis in a subject in need thereof comprising contacting the tissue graft with a construct comprising an aptamer conjugated to a therapeutic nucleic acid in an amount effective to inhibit apoptosis of the tissue graft. In some embodiments, the therapeutic nucleic acid is a therapeutic RNA. In some embodiments, the therapeutic RNA is selected from the group consisting of siRNA and saRNA. In some embodiments, the therapeutic RNA upregulates the protein XIAP (X-linked inhibitor of apoptosis gene id 331). The contacting step can occur in vitro or in vivo. In some embodiments, the tissue graft is from an organ selected from the group consisting of pancreas, heart, lung, kidney, stomach and skin. In some embodiments, the aptamer is a muscle specific aptamer and the tissue is heart tissue.

In some embodiments, the tissue is contacted with the therapeutic RNA that upregulates the protein XIAP in the absence of an aptamer. For example, in another aspect, the disclosure provides a method for inhibiting tissue graft apoptosis in a subject in need thereof comprising contacting the tissue graft with a therapeutic RNA that upregulates the protein XIAP (X-linked inhibitor of apoptosis gene id 331) in an amount effective to inhibit apoptosis of the tissue graft. The contacting step can occur in vitro or in vivo. In some embodiments, the tissue graft is from an organ selected from the group consisting of pancreas, heart, lung, kidney, stomach and skin.

In another aspect, the disclosure provides a method for protecting a beta cell from T-cell mediated cytotoxicity of the beta cell comprising contacting the beta cell with a construct comprising an aptamer conjugated to a therapeutic nucleic acid in an amount effective to inhibit T cell mediated cytotoxicity of the beta cell. In some embodiments, the aptamer is selected from the group consisting of M12-3773 and 1-717. In some embodiments, the therapeutic nucleic acid is able to increase immune checkpoint. In some embodiments, the therapeutic nucleic acid is a therapeutic RNA. In some embodiments, the therapeutic RNA is selected from the group consisting of siRNA and saRNA. In some embodiments the therapeutic RNA upregulate the protein CD274 (Programmed death-ligand 1, PDL1, gene id 29126). The contacting step can occur in vitro or in vivo.

In another aspect, the disclosure provides a method of treating diabetes in a subject in need thereof comprising administering to the subject a construct comprising an aptamer conjugated to a small activating RNA (saRNA) in an amount effective to treat diabetes in the subject. In some embodiments, the aptamer is selected from the group consisting of M12-3773 and 1-717.

In another aspect, one or more aptamers specific for the beta cells can be used in combination to increase delivery of the therapeutic agent or imaging reagents. In some embodiments, the aptamers are selected from the group consisting of M12-3773 and 1-717.

An aptamer comprising a nucleotide sequence set forth in SEQ ID NO: 264 or 259 is also contemplated. In some embodiments, the aptamer is conjugated to an saRNA. In some embodiments, the saRNA upregulates the protein XIAP (X-linked inhibitor of apoptosis gene id 331). In some embodiments, saRNA upregulates the protein CD274 (Programmed death-ligand 1, PDL1, gene id 29126,

BRIEF DESCRIPTION OF THE FIGURES

FIGS. 5A and 5B show that aptamers 1-717 (FIG. 5A) and M12-3772 (FIG. 5B) show an extraordinary specificity for human islets. FIG. 5C is a table showing the results of various tissue staining with various selected aptamers.

FIG. 6 shows that aptamers 1-717 and M12-3772 recognize mouse islets and other mouse tissues.

FIG. 11 shows that Aptamer 1-717 and M12-3773 allow the measurement of human beta cell mass in vivo. FIG. 11D: Syngeneic (Balb/c) or allogeneic (C57B1/6) ilsets were transplanted subcutaneously (in the right and left flank respectively) of immunocompetent Balb/c mice. Rejection was longitudinally monitored by injecting AF750-conjugated aptamer intravenously and by performing IVIS 5 hours later. Data show that rejection of the allogeneic C57B16 islet graft can be measured over time as seen by the loss of signal on the left flank. Instead signal (right) of the syngeneic islet graft is maintained over time indicating graft survival.

FIG. 20. PDL1-saRNA/aptamer chimera upregulate PDL1 in vivo.

DETAILED DESCRIPTION

Figure 1:
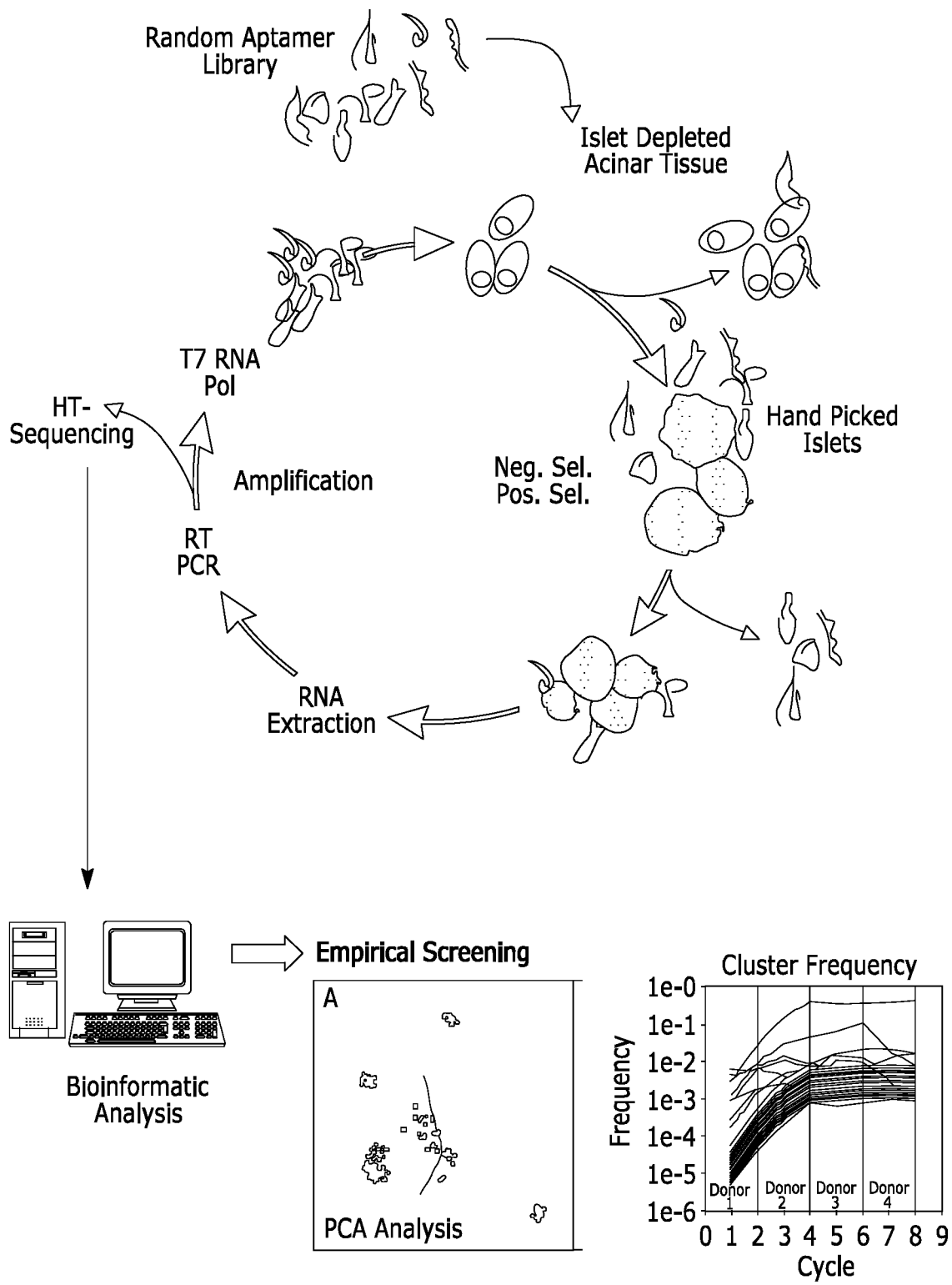
FIG. 1 is a flow chart showing HT-cluster SELEX as an unsupervised strategy for the isolation of aptamers specific for human islets using human islets and acinar tissue.

As described in the Examples, therapeutic RNA/aptamer chimeras were generated to modulate gene expression in human β cells in vivo to induce their transient proliferation and improve their resistance to auto/alloimmunity. In particular, we have optimized and validate the use of islet-specific aptamers to deliver: A) siRNA against p57kip2 to induce β cell proliferation, B) saRNA promoting Xiap expression to protect islets from apoptosis, and C) saRNA promoting PDL1 expression to protect β from T cell cytotoxicity. Because of the absence of reliable humanized mouse model of autoimmune T1D, our approach is based on the use of NSG or humanized NSG mice transplanted with human islets before aptamer treatment. The use of human islets is dictated by species specific difference in p57kip2 biology (14) and by the specificity of PDL1 and Xiap saRNAs for the human genes. Ex vivo and innovative in vivo techniques are employed to quantify the response to in vivo treatment through imaging of β cell proliferation, apoptosis, and interaction with the immune system. We envision the use of these aptamers as mono or multimodal approach where difference genes can be modulated simultaneously.

The in vivo use of RNA aptamers is particularly appealing because this class of molecules has low immunogenicity, high capacity to penetrate deep into the tissues, and ability to recognize the cognate target with high affinity and specificity. The fluorinated backbone of the aptamers make them resistant to RNAse degradation and incapable to trigger TLR signaling (41,42). RNA aptamers have emerged as effective delivery vehicles for siRNAs and other drugs to specific cell subsets or tissues for the treatment of many human diseases (60, 62-75). Indeed, through the interactions between the aptamer and its cellular membrane target, aptamers actively enhance the intracellular accumulation of therapeutic agents (37-39, 43-61). Some aptamer drugs are FDA-approved and more than 30 are being tested in clinical trials (16-24). When administered in vivo, aptamers that do not find a specific target are rapidly eliminated via the kidney; those that find their target in tissues or cells remain detectable for up two weeks. Their bioavailability, plasma half-life, and pharmacokinetic properties can be easily engineered by increasing their size by the addition of Polyethylene glycol (PEG) during synthesis, or by conjugation with nanoparticles (60, 62-74). Aptamers can be conjugated to siRNA, miRNA or saRNA to deliver the desirable therapeutic effect in specific targets. The ability to directly engineer aptamers with high specificity and defined functions is a distinct advantage over antibodies and other small molecules.

EXAMPLES

Example 1—Isolation of Monoclonal RNA Aptamer Specific for Human Islets

Unsupervised toggled-SELEX was performed starting with a polyclonal aptamer library against mouse islets and using islet depleted human acinar cells and handpicked human islets from 4 different cadaveric donors as negative and positive selectors, respectively. This allowed for the depletion of non-specific (acinar tissue binding) RNA aptamers and enrich the library for those aptamers specific for mouse and human islets.

As shown in FIG. 1, HT-cluster SELEX was used as an unsupervised strategy for the isolation of aptamers specific for human islets using human islets and acinar tissue. A random aptamer library was generated by PCR and Durascribe T7 RNA transcription from a cDNA random library (TCT CGG ATC CTC AGC GAG TCG TC TG (N40) CCG CAT CGT CCT CCC TA (SEQ ID NO: 413), comprising a 40-nt variable region flanked by two constant region. 5 ug (~8.3×10$^{13}$ aptamers) of this random library were depleted for aptamers binding the acinar tissue using islets depleted pancreata (negative selector) from cadaveric donors. Unbound aptamers were then incubated with hand-picked islets (100-300 IEQ as positive selector) from cadaveric donors. Islets were washed with PBS and islets-bound aptamers were recovered by RNA extraction and re-amplified by RT-PCR and T7-RNA polymerase using 2'-Fluorine-dCTP (2'-F-dCTP) and 2'-Fluorine-dUTP (2'-F-dUTP), ATP, and GTP for improved RNAse resistance. The resulting RNA aptamer library (Table 1), enriched for islets specific aptamers, was used for new selection cycle. A total of 8 selection cycles was performed using islets and acinar tissue from 4 unrelated cadaveric donors. Library from each cycles were HT sequenced and subject to bio-informatic analysis to perform frequency and cluster analysis and identify those monoclonal aptamer and family of aptamers enriched during the selection process. The most frequent monoclonal aptamers among the most frequent families present on the library from cycle 8 were chosen for empirical testing.

Table 2. Putative human islet specific aptamers isolated via cluster SELEX (from FIG. 1)

TABLE 2

| \multicolumn{3}{c}{Putative human islet specific aptamers isolated via cluster SELEX (from FIG. 1)} |
|---|---|---|
| aptamer name | SEQ ID NO. | sequence |
| 279 | 1 | GGAGGAGCUACGAUGCGGCCGAUUUCGUCAUCCUCCAUA CCAUCGCCUUACCGUUCCGCGUCAGACGACUCGCUGAGGAUCCG ACA |
| 2529 | 2 | GGAGGAGCUACGAUGCGGCCGUCUCGCUCUCAUCCCAUGCA CGAAACCUCUCUCACUGCACAGACGACUCGCUGAGGAUCCGACA |
| 2031 | 3 | GGAGGAGCUACGAUGCGGUGAAUUCUUCCGGCACUUUGUCA UCUUCACCCCCAUGCUGCACAGACGACUCGCUGAGGAUCCGACA |
| 1134 | 4 | GGAGGAGCUACGAUGCGGCCGAUUUCGUCAUCCUCCAUACCA UCGCCUCACCGUUCCGCGUCAGACGACUCGCUGAGGAUCCGACA |
| 664 | 5 | GGAGGAGCUACGAUGCGGCCGAUUUCGUCAUCCUCCACACCAUC G CCUUACCGUUCCGCGUCAGACGACUCGCUGAGGAUCCGACA |
| 877 | 6 | GGAGGAGCUACGAUGCGGCCGAUUUCGUCAUCCUCCGUACCAUC GC CUUACCGUUCCGCGUCAGACGACUCGCUGAGGAUCCGACA |
| 2437 | 7 | GGAGGAGCUACGAUGCGGCCCAUCACUCCCGCGUAUUGCGAACG CAU CGUUAUUUAGCCGUCAGACGACUCGCUGAGGAUCCGACA |
| 1131 | 8 | GGAGGAGCUACGAUGCGGUCGAUUUCGUCAUCCUCCAUACCAUC GCC UUACCGUUCCGCGUCAGACGACUCGCUGAGGAUCCGACA |
| 436 | 9 | GGAGGAGCUACGAUGCGGCCGAUUUCGUCAUCCUCCAUACCAUC GUC UUACCGUUCCGCGUCAGACGACUCGCUGAGGAUCCGACA |
| 19 | 10 | GGAGGAGCUACGAUGCGGCCGAUUUCGUCAUCCUCCAUACCAUC GC CUUACCGCUCCGCGUCAGACGACUCGCUGAGGAUCCGACA |
| 665 | 11 | GGAGGAGCUACGAUGCGGCCGAUUUCGUCAUCCUCCAUGCCAUC GCC UUACCGUUCCGCGUCAGACGACUCGCUGAGGAUCCGACA |
| 280 | 12 | GGAGGAGCUACGAUGCGGCCGAUUUCGUCAUCCUCCAUACCAUC GCCCUACCGUUCCGCGUCAGACGACUCGCUGAGGAUCCGACA |
| 79 | 13 | GGAGGAGCUACGAUGCGGCCGAUUUCGUCAUCCUCCAUACCAUC GCCUUGCCGUUCCGCGUCAGACGACUCGCUGAGGAUCCGACA |
| 278 | 14 | GGAGGAGCUACGAUGCGGCCGAUUUCGUCAUCCUCCAUACCAUC GCCUUACCAUUCCGCGUCAGACGACUCGCUGAGGAUCCGACA |
| 658 | 15 | GGAGGAGCUACGAUGCGGCCGAUUUCGUCAUCCCCCAUACCAUC GCCUUACCGUUCCGCGUCAGACGACUCGCUGAGGAUCCGACA |

TABLE 2-continued

Putative human islet specific aptamers isolated via cluster SELEX (from FIG. 1)

| aptamer name | SEQ ID NO. | sequence |
| --- | --- | --- |
| 37 | 16 | GGAGGAGCUACGAUGCGGCCGAUAUCGUCAUCCUCCAUACCAUC<br>GCCUUACCGUUCCGCGUCAGACGACUCGCUGAGGAUCCGACA |
| 485 | 17 | GGAGGAGCUACGAUGCGGCCGAUUUCGUCAUCCUCCAUACCAUC<br>GCCUACCGUUCCGCGUCAGACGACUCGCUGAGGAUCCGACA |
| 2617 | 18 | GGAGGAGCUACGAUGCGGUGUACACUGAUUGCCUUUGUGUUAUG<br>AGCGACAGAUCUGCCAGACAGACGACUCGCUGAGGAUCCGACA |
| 2273 | 19 | GGAGGAGCUACGAUGCGGACCUUGUUUUCCUCUGUACCCCACUU<br>CCCCAUUUCUCCCUGCUCAGACGACUCGCUGAGGAUCCGACA |
| 146 | 20 | GGAGGAGCUACGAUGCGGCCGAUCUCGUCAUCCUCCAUACCAUC<br>GCCUUACCGUUCCGCGUCAGACGACUCGCUGAGGAUCCGACA |
| 657 | 21 | GGAGGAGCUACGAUGCGGCCGAUUUCGUCAUCCUCCAUACCAUC<br>GCCUUACCGUCCCGCGUCAGACGACUCGCUGAGGAUCCGACA |
| 141 | 22 | GGAGGAGCUACGAUGCGGCCGAUUUCGUCAUCCUCCAUACCGUC<br>GCCUUACCGUUCCGCGUCAGACGACUCGCUGAGGAUCCGACA |
| 2048 | 23 | GGAGGAGCUACGAUGCGGCCGAUUUCGUCGUCCUCCAUACCAUC<br>GCCUUACCGUUCCGCGUCAGACGACUCGCUGAGGAUCCGACA |
| 901 | 24 | GGAGGAGCUACGAUGCGGGGAAGCAACACUUAGUCGCGAUUGAU<br>ACGUGCGCAGUCAUCAGACAGACGACUCGCUGAGGAUCCGACA |
| 268 | 25 | GGAGGAGCUACGAUGCGGCCGAUUUCGCCAUCCUCCAUACCAUC<br>GCCUUACCGUUCCGCGUCAGACGACUCGCUGAGGAUCCGACA |
| 683 | 26 | GGAGGAGCUACGAUGCGGCCGAUUUCGUCAUCCUCCAUACCAUC<br>GCCUUCCGUUCCGCGUCAGACGACUCGCUGAGGAUCCGACA |
| 655 | 27 | GGAGGAGCUACGAUGCGGCCGAUUUCGUCAUCCUCCAUAUCAUC<br>GCCUUACCGUUCCGCGUCAGACGACUCGCUGAGGAUCCGACA |
| 1427 | 28 | GGAGGAGCUACGAUGCGGCCGAUUUCGUCACCCUCCAUACCAUC<br>GCCUUACCGUUCCGCGUCAGACGACUCGCUGAGGAUCCGACA |
| 457 | 29 | GGAGGAGCUACGAUGCGGCCGACUUCGUCAUCCUCCAUACCAUC<br>GCCUUACCGUUCCGCGUCAGACGACUCGCUGAGGAUCCGACA |
| 1141 | 30 | GGAGGAGCUACGAUGCGGCCGAUUUCGUCAUCCUCCAUACCAUC<br>GCCUUACCUUCCGCGUCAGACGACUCGCUGAGGAUCCGACA |
| 149 | 31 | GGAGGAGCUACGAUGCGGCCGAUUUCGUCAUCCUCCAUACCAUC<br>GCCUUACCGUUCCGCAGUCAGACGACUCGCUGAGGAUCCGACA |
| 1759 | 32 | GGAGGAGCUACGAUGCGGCCGAUUUCGUCAUCCUCCUUACCAUC<br>GCCUUACCGUUCCGCGUCAGACGACUCGCUGAGGAUCCGACA |
| 264 | 33 | GGAGGAGCUACGAUGCGGCCGAUUUCGUCAUCCUUCAUACCAUC<br>GCCUUACCGUUCCGCGUCAGACGACUCGCUGAGGAUCCGACA |
| 259 | 34 | GGAGGAGCUACGAUGCGGCCGAUUUCGUCAUCCUCCAUACUAUC<br>GCCUUACCGUUCCGCGUCAGACGACUCGCUGAGGAUCCGACA |
| 1130 | 35 | GGAGGAGCUACGAUGCGGCCGAUUUCAUCAUCCUCCAUACCAUC<br>GCCUUACCGUUCCGCGUCAGACGACUCGCUGAGGAUCCGACA |
| 453 | 36 | GGAGGAGCUACGAUGCGGCCGAUUUCGUCAUCCUCCAUACCAUC<br>GCCUUACCUUUCCGCGUCAGACGACUCGCUGAGGAUCCGACA |
| 1133 | 37 | GGAGGAGCUACGAUGCGGCCGAUUUCGUCAUCCUCUAUACCAUC<br>GCCUUACCGUUCCGCGUCAGACGACUCGCUGAGGAUCCGACA |
| 883 | 38 | GGAGGAGCUACGAUGCGGCCGAUUUCGUCAUCCUCCAAACCAUC<br>GCCUUACCGUUCCGCGUCAGACGACUCGCUGAGGAUCCGACA |
| 155 | 39 | GGAGGAGCUACGAUGCGGCCGAUUUCGUCAUCCUCCAUACCAUC<br>GCCUUAUCGUUCCGCGUCAGACGACUCGCUGAGGAUCCGACA |

TABLE 2-continued

Putative human islet specific aptamers isolated via cluster SELEX (from FIG. 1)

| aptamer name | SEQ ID NO. | sequence |
|---|---|---|
| 75 | 40 | GGAGGAGCUACGAUGCGGCCGAUUCCGUCAUCCUCCAUACCAUC<br>GCCUUACCGUUCCGCGUCAGACGACUCGCUGAGGAUCCGACA |
| 2049 | 41 | GGAGGAGCUACGAUGCGGCUGAUUUCGUCAUCCUCCAUACCAUC<br>GCCUUACCGUUCCGCGUCAGACGACUCGCUGAGGAUCCGACA |
| 1103 | 42 | GGAGGAGCUACGAUGCGGCCGAUUUUCGUCAUCCUCCAUACCAU<br>CGCCUUACCGUUCCGCGUCAGACGACUCGCUGAGGAUCCGACA |
| 885 | 43 | GGAGGAGCUACGAUGCGGCCGAUUUCGUCAUCCUCAAUACCAUC<br>GCCUUACCGUUCCGCGUCAGACGACUCGCUGAGGAUCCGACA |
| 281 | 44 | GGAGGAGCUACGAUGCGGCCGAUUUCGUCAUCCUCCAUACCAUC<br>GCCUUCCCGUUCCGCGUCAGACGACUCGCUGAGGAUCCGACA |
| 2381 | 45 | GGAGGAGCUACGAUGCGGAUUACCAACUUGAACGCCGAGAGUGU<br>GGUCACGUGUUCUGCAGACAGACGACUCGCUGAGGAUCCGACA |
| 879 | 46 | GGAGGAGCUACGAUGCGGCCGAUUUCGUCAUCCUCCAUACCAUC<br>GCCUUACCGUUUCGCGUCAGACGACUCGCUGAGGAUCCGACA |
| 292 | 47 | GGAGGAGCUACGAUGCGGCCGAUUUCGUAUCCUCCAUACCAUCG<br>CCUUACCGUUCCGCGUCAGACGACUCGCUGAGGAUCCGACA |
| 1511 | 48 | GGAGGAGCUACGAUGCGGUUAUGCGUUUAAGUCAUUGACGCGUU<br>ACACUGGAGGGGCCAGACAGACGACUCGCUGAGGAUCCGACA |
| 148 | 49 | GGAGGAGCUACGAUGCGGCCGAUUUCGUCAUCCUCCAUACCAUC<br>GCCUUACCGUUCCGCAUCAGACGACUCGCUGAGGAUCCGACA |
| 878 | 50 | GGAGGAGCUACGAUGCGGCCGAUUUCGUCAUCCUCCAUAACAUC<br>GCCUUACCGUUCCGCGUCAGACGACUCGCUGAGGAUCCGACA |
| 156 | 51 | GGAGGAGCUACGAUGCGGCCGAUUUCGUCAUCCUCCUACCAUCG<br>CCUUACCGUUCCGCGUCAGACGACUCGCUGAGGAUCCGACA |
| 266 | 52 | GGAGGAGCUACGAUGCGGCCGAUUUCGUUAUCCUCCAUACCAUC<br>GCCUUACCGUUCCGCGUCAGACGACUCGCUGAGGAUCCGACA |
| 459 | 53 | GGAGGAGCUACGAUGCGGCCGAUUUCGUCAUCCUCCAUACCAUC<br>GCCAUACCGUUCCGCGUCAGACGACUCGCUGAGGAUCCGACA |
| 668 | 54 | GGAGGAGCUACGAUGCGGCCGAUUUCGUCAUCCUCCAUACCAUC<br>GCCUAACCGUUCCGCGUCAGACGACUCGCUGAGGAUCCGACA |
| 1760 | 55 | GGAGGAGCUACGAUGCGGCCGAUUUCGUCAUCCUCCAUACCAUC<br>GCUUUACCGUUCCGCGUCAGACGACUCGCUGAGGAUCCGACA |
| 661 | 56 | GGAGGAGCUACGAUGCGGCCGAUUUCGUCAUCCUCCAUACCAUU<br>GCCUUACCGUUCCGCGUCAGACGACUCGCUGAGGAUCCGACA |
| 1129 | 57 | GGAGGAGCUACGAUGCGGCCGAUUUCGUCAUACUCCAUACCAUC<br>GCCUUACCGUUCCGCGUCAGACGACUCGCUGAGGAUCCGACA |
| 438 | 58 | GGAGGAGCUACGAUGCGGCCGAUUUCGUCAUCCUCCAUAGCAUC<br>GCCUUACCGUUCCGCGUCAGACGACUCGCUGAGGAUCCGACA |
| 277 | 59 | GGAGGAGCUACGAUGCGGCCGAUUUCGUCAUCCUCCAUACCAUC<br>GCCUUACCCUUCCGCGUCAGACGACUCGCUGAGGAUCCGACA |
| 18 | 60 | GGAGGAGCUACGAUGCGGCCGAUUUCGUAAUCCUCCAUACCAUC<br>GCCUUACCGUUCCGCGUCAGACGACUCGCUGAGGAUCCGACA |
| 152 | 61 | GGAGGAGCUACGAUGCGGCCGAUUUCGUCAUCCUCCAUACCAUC<br>ACCUUACCGUUCCGCGUCAGACGACUCGCUGAGGAUCCGACA |
| 460 | 62 | GGAGGAGCUACGAUGCGGCCGAUUUCGUCAUCCUCCAUACCAUC<br>GCCUUUCCGUUCCGCGUCAGACGACUCGCUGAGGAUCCGACA |
| 1370 | 63 | GGAGGAGCUACGAUGCGGCCCAUCCCUCCCGCGUAUUGCGAACG<br>CAUCGUUAUUUAGCCGUCAGACGACUCGCUGAGGAUCCGACA |

TABLE 2-continued

Putative human islet specific aptamers isolated via cluster SELEX (from FIG. 1)

| aptamer name | SEQ ID NO. | sequence |
|---|---|---|
| 717 | 64 | GGAGGAGCUACGAUGCGGUAAUUCUCAGGAGGUGCGGAACGGGA<br>UAUGGAUUGUUCGCCAGACAGACGACUCGCUGAGGAUCCGACA |
| 456 | 65 | GGAGGAGCUACGAUGCGGCCGAUUUCGUCAUCCUCCAUCCCAUC<br>GCCUUACCGUUCCGCGUCAGACGACUCGCUGAGGAUCCGACA |
| 876 | 66 | GGAGGAGCUACGAUGCGGCCGAUUUCGUCAUCAUCCAUACCAUC<br>GCCUUACCGUUCCGCGUCAGACGACUCGCUGAGGAUCCGACA |
| 391 | 67 | GGAGGAGCUACGAUGCGGUGAAUUCUUCCGGCACUUUGUCAUCU<br>UCACUCCCAUGCUGCACAGACGACUCGCUGAGGAUCCGACA |
| 659 | 68 | GGAGGAGCUACGAUGCGGCCGAUUUCGUCAUCCUACAUACCAUC<br>GCCUUACCGUUCCGCGUCAGACGACUCGCUGAGGAUCCGACA |
| 437 | 69 | GGAGGAGCUACGAUGCGGCCGAUUUCGUCAUCCUCCAUACCAUC<br>CCCUUACCGUUCCGCGUCAGACGACUCGCUGAGGAUCCGACA |
| 143 | 70 | GGAGGAGCUACGAUGCGGCCGAUUUCGUCAUCCACCAUACCAUC<br>GCCUUACCGUUCCGCGUCAGACGACUCGCUGAGGAUCCGACA |
| 802 | 71 | GGAGGAGCUACGAUGCGGCCGUCUCGCUCUCAUCCCGUGCACGA<br>AACCUCUCUCACUGCACAGACGACUCGCUGAGGAUCCGACA |
| 2192 | 72 | GGAGGAGCUACGAUGCGGCAACAAACUAAUCAGACACGAGACAGA<br>GAGAUAGAUCUGCCAGACAGACGACUCGCUGAGGAUCCGACA |
| 1736 | 73 | GGAGGAGCUACGAUGCGGUGAAUUCUUCCGGCACUUUGUCAUCU<br>UCACCCCCUGCUGCACAGACGACUCGCUGAGGAUCCGACA |
| 462 | 74 | GGAGGAGCUACGAUGCGGCCGAUUUCGUCAUCCUCCAUACCAUC<br>GCCUUAGCGUUCCGCGUCAGACGACUCGCUGAGGAUCCGACA |
| 882 | 75 | GGAGGAGCUACGAUGCGGCCGAUUUCGUCAUCCUCCAUACCAUA<br>GCCUUACCGUUCCGCGUCAGACGACUCGCUGAGGAUCCGACA |
| 140 | 76 | GGAGGAGCUACGAUGCGGCCGAUUUCGUCAUCCUCCAUACAAUC<br>GCCUUACCGUUCCGCGUCAGACGACUCGCUGAGGAUCCGACA |
| 363 | 77 | GGAGGAGCUACGAUGCGGCCCAUCACUCCCGCGUACUGCGAACG<br>CAUCGUUAUUUAGCCGUCAGACGACUCGCUGAGGAUCCGACA |
| 275 | 78 | GGAGGAGCUACGAUGCGGCCGAUUUCGUCAUCCUCCAUACCAUC<br>GCCUUACCGAUCCGCGUCAGACGACUCGCUGAGGAUCCGACA |
| 667 | 79 | GGAGGAGCUACGAUGCGGCCGAAUUCGUCAUCCUCCAUACCAUC<br>GCCUUACCGUUCCGCGUCAGACGACUCGCUGAGGAUCCGACA |
| 36 | 80 | GGAGGAGCUACGAUGCGGCCGAUUUCGUCAUCCUCCAUACCAUC<br>GACUUACCGUUCCGCGUCAGACGACUCGCUGAGGAUCCGACA |
| 441 | 81 | GGAGGAGCUACGAUGCGGCCGAUUUCGUCAUCCUGCAUACCAUC<br>GCCUUACCGUUCCGCGUCAGACGACUCGCUGAGGAUCCGACA |
| 1383 | 82 | GGAGGAGCUACGAUGCGGUCCUUGUUUUCCUCUGUACCCCACUU<br>CCCCAUUUCUCCCUGCUCAGACGACUCGCUGAGGAUCCGACA |
| 1429 | 83 | GGAGGAGCUACGAUGCGGCCGAUUUCUUCAUCCUCCAUACCAUC<br>GCCUUACCGUUCCGCGUCAGACGACUCGCUGAGGAUCCGACA |
| 262 | 84 | GGAGGAGCUACGAUGCGGCCGAUUUCGUCAUCCUCCAUACCAUC<br>UCCUUACCGUUCCGCGUCAGACGACUCGCUGAGGAUCCGACA |
| 451 | 85 | GGAGGAGCUACGAUGCGGCCGAUUUCGUCAUCCUCCAUACCAUG<br>GCCUUACCGUUCCGCGUCAGACGACUCGCUGAGGAUCCGACA |
| 446 | 86 | GGAGGAGCUACGAUGCGGCCGAUUUCGGCAUCCUCCAUACCAUC<br>GCCUUACCGUUCCGCGUCAGACGACUCGCUGAGGAUCCGACA |
| 265 | 87 | GGAGGAGCUACGAUGCGGCCGAUUUCGUGAUCCUCCAUACCAUC<br>GCCUUACCGUUCCGCGUCAGACGACUCGCUGAGGAUCCGACA |

TABLE 2-continued

Putative human islet specific aptamers isolated via cluster SELEX (from FIG. 1)

| aptamer name | SEQ ID NO. | sequence |
|---|---|---|
| 880 | 88 | GGAGGAGCUACGAUGCGGCCGAUUUCGUCAUCCUCCAUACCAUC<br>GCCUUACCGUACCGCGUCAGACGACUCGCUGAGGAUCCGACA |
| 323 | 89 | GGAGGAGCUACGAUGCGGACGGAGGAUAGUUGCUAAUCGAGCCC<br>UGCCGACGCUUCAGACAGACGACUCGCUGAGGAUCCGACA |
| 458 | 90 | GGAGGAGCUACGAUGCGGCCGAUUUCGUCAUCCUCCGUACCAUC<br>GCCUCACCGUUCCGCGUCAGACGACUCGCUGAGGAUCCGACA |
| 662 | 91 | GGAGGAGCUACGAUGCGGCCGAUUUCGUCAUCCUCCAUACCAUC<br>GCCUUACAGUUCCGCGUCAGACGACUCGCUGAGGAUCCGACA |
| 682 | 92 | GGAGGAGCUACGAUGCGGCCGAUUUCGUCAUCCUCCAUACCAUC<br>CCUUACCGUUCCGCGUCAGACGACUCGCUGAGGAUCCGACA |
| 154 | 93 | GGAGGAGCUACGAUGCGGCCGAUUUCGUCAUCCUCCAUACCAUC<br>GCCUGACCGUUCCGCGUCAGACGACUCGCUGAGGAUCCGACA |
| 282 | 94 | GGAGGAGCUACGAUGCGGCCGAUUUCGUCAUCCUCCAUACCAUC<br>GCCUUAACGUUCCGCGUCAGACGACUCGCUGAGGAUCCGACA |
| 449 | 95 | GGAGGAGCUACGAUGCGGCCGAUUUCGUCAUCCUCCAUACCAUC<br>GCCUUACCGGUCCGCGUCAGACGACUCGCUGAGGAUCCGACA |
| 16 | 96 | GGAGGAGCUACGAUGCGGCCGAUUCGUCAUCCUCCAUACCAUCG<br>CCUUACCGUUCCGCGUCAGACGACUCGCUGAGGAUCCGACA |
| 900 | 97 | GGAGGAGCUACGAUGCGGCCGAUUUCGUCAUCCUCCAUACCAUC<br>GCCUUACCGUCCGCGUCAGACGACUCGCUGAGGAUCCGACA |
| 2032 | 98 | GGAGGAGCUACGAUGCGGUGAAUUCUUCCGGCACUUUGUCAUCU<br>UCACCCCCAUGCUGCGCAGACGACUCGCUGAGGAUCCGACA |
| 267 | 99 | GGAGGAGCUACGAUGCGGCCGAUUUCGUCAUCCUCCAUACCAAC<br>GCCUUACCGUUCCGCGUCAGACGACUCGCUGAGGAUCCGACA |
| 72 | 100 | GGAGGAGCUACGAUGCGGCCGAUUUCGUCAUCCUCCAUACCCUC<br>GCCUUACCGUUCCGCGUCAGACGACUCGCUGAGGAUCCGACA |
| 1075 | 101 | GGAGGAGCUACGAUGCGGUGAAUUCUUCCGGCACUUUGUCAUCU<br>UCACCUCCAUGCUGCACAGACGACUCGCUGAGGAUCCGACA |
| 261 | 102 | GGAGGAGCUACGAUGCGGCCGAUUUCGUCAUCCUCCAUACCAUC<br>GGCUUACCGUUCCGCGUCAGACGACUCGCUGAGGAUCCGACA |
| 801 | 103 | GGAGGAGCUACGAUGCGGCCGUCUCGCUCUCAUCCCAUGCACGA<br>AACCUCUCUCGCUGCACAGACGACUCGCUGAGGAUCCGACA |
| 291 | 104 | GGAGGAGCUACGAUGCGGCCGAUUUGUCAUCCUCCAUACCAUCG<br>CCUUACCGUUCCGCGUCAGACGACUCGCUGAGGAUCCGACA |
| 599 | 105 | GGAGGAGCUACGAUGCGGUGAAUUCUUCCGGCACUUUGUCAUCU<br>UCACCCCCACGCUGCACAGACGACUCGCUGAGGAUCCGACA |
| 272 | 106 | GGAGGAGCUACGAUGCGGCCGAUUACGUCAUCCUCCAUACCAUC<br>GCCUUACCGUUCCGCGUCAGACGACUCGCUGAGGAUCCGACA |
| 447 | 107 | GGAGGAGCUACGAUGCGGCCGAUUUCGCCAUCCUCCAUACCAUC<br>GCCUCACCGUUCCGCGUCAGACGACUCGCUGAGGAUCCGACA |
| 74 | 108 | GGAGGAGCUACGAUGCGGCCGAUUUCGACAUCCUCCAUACCAUC<br>GCCUUACCGUUCCGCGUCAGACGACUCGCUGAGGAUCCGACA |
| 674 | 109 | GGAGGAGCUACGAUGCGGCCGAUUUCGUCAUCCUCCAUACAUCG<br>CCUUACCGUUCCGCGUCAGACGACUCGCUGAGGAUCCGACA |
| 4 | 110 | GGAGGAGCUACGAUGCGGCCGAUUUCGUCAUCCUCCAUACGAUC<br>GCCUUACCGUUCCGCGUCAGACGACUCGCUGAGGAUCCGACA |
| 455 | 111 | GGAGGAGCUACGAUGCGGCCGAUUUCGUCAUCCUCCGUACCAUC<br>GCCUUACCAUUCCGCGUCAGACGACUCGCUGAGGAUCCGACA |

TABLE 2-continued

Putative human islet specific aptamers isolated via cluster SELEX (from FIG. 1)

| aptamer name | SEQ ID NO. | sequence |
|---|---|---|
| 890 | 112 | GGAGGAGCUACGAUGCGGCCGAUUUCGUCAUCCCCAUACCAUCG CCUUACCGUUCCGCGUCAGACGACUCGCUGAGGAUCCGACA |
| 260 | 113 | GGAGGAGCUACGAUGCGGCCGAUUUCGUCAUCCUCCAUACCUUC GCCUUACCGUUCCGCGUCAGACGACUCGCUGAGGAUCCGACA |
| 39 | 114 | GGAGGAGCUACGAUGCGGCCGAUUUCGUCAUGCUCCAUACCAUC GCCUUACCGUUCCGCGUCAGACGACUCGCUGAGGAUCCGACA |
| 57 | 115 | GGAGGAGCUACGAUGCGGCCCAUCACUCCCGCGCAUUGCGAACG CAUCGUUAUUUAGCCGUCAGACGACUCGCUGAGGAUCCGACA |
| 889 | 116 | GGAGGAGCUACGAUGCGGCCGAUUUCGUCAUCUCCAUACCAUCG CCUUACCGUUCCGCGUCAGACGACUCGCUGAGGAUCCGACA |
| 828 | 117 | GGAGGAGCUACGAUGCGGUGAAUUCUUCCGGCACUUUGUCAUCU UCACCCCAUGCCGCACAGACGACUCGCUGAGGAUCCGACA |
| 2016 | 118 | GGAGGAGCUACGAUGCGGCCCAUCACUCCCGCGUAUUGCGAACG CCUCGUUAUUUAGCCGUCAGACGACUCGCUGAGGAUCCGACA |
| 666 | 119 | GGAGGAGCUACGAUGCGGUCGAUUUCGUCAUCCUCCGUACCAUC GCCUUACCGUUCCGCGUCAGACGACUCGCUGAGGAUCCGACA |
| 1738 | 120 | GGAGGAGCUACGAUGCGGUGAAUUCUUCCGGCACUUUGUCAUCU UCAUCCCCAUGCUGCACAGACGACUCGCUGAGGAUCCGACA |
| 656 | 121 | GGAGGAGCUACGAUGCGGCCGAUUUCGUCAUCCUCCAUACCAUC GCCUUACCGUUACGCGUCAGACGACUCGCUGAGGAUCCGACA |
| 654 | 122 | GGAGGAGCUACGAUGCGGCCGAUUUCGUCAACCUCCAUACCAUC GCCUUACCGUUCCGCGUCAGACGACUCGCUGAGGAUCCGACA |
| 440 | 123 | GGAGGAGCUACGAUGCGGCCGAUUUCGUCAUCCGCCAUACCAUC GCCUUACCGUUCCGCGUCAGACGACUCGCUGAGGAUCCGACA |
| 370 | 124 | GGAGGAGCUACGAUGCGGCCGUCUCGCUCUAUCCCAUGCACGA AACCUCUCUCCCUGCACAGACGACUCGCUGAGGAUCCGACA |
| 881 | 125 | GGAGGAGCUACGAUGCGGCCGAUUUCGUCAUCCUCCACACCAUC GCCUUACCGCUCCGCGUCAGACGACUCGCUGAGGAUCCGACA |
| 150 | 126 | GGAGGAGCUACGAUGCGGCCGAUUUCGUCAUCCUCCAUACCAUC GCCUUACCGUUCCGCUUCAGACGACUCGCUGAGGAUCCGACA |
| 73 | 127 | GGAGGAGCUACGAUGCGGCCGAUUUCGUCAUCGUCCAUACCAUC GCCUUACCGUUCCGCGUCAGACGACUCGCUGAGGAUCCGACA |
| 670 | 128 | GGAGGAGCUACGAUGCGGCCGAUUUCGUCAUCCUCCAUACCAUC GCCGUACCGUUCCGCGUCAGACGACUCGCUGAGGAUCCGACA |
| 263 | 129 | GGAGGAGCUACGAUGCGGCCGAUUUCGUCAUCCUCCAUACCAUC GCCUUACCGUUGCGCGUCAGACGACUCGCUGAGGAUCCGACA |
| 270 | 130 | GGAGGAGCUACGAUGCGGCCGAUGUCGUCAUCCUCCAUACCAUC GCCUUACCGUUCCGCGUCAGACGACUCGCUGAGGAUCCGACA |
| 1137 | 131 | GGAGGAGCUACGAUGCGGCCGAUAUCGUCAUCCUCCAUACCAUC GCCUUCCGUUCCGCGUCAGACGACUCGCUGAGGAUCCGACA |
| 238 | 132 | GGAGGAGCUACGAUGCGGCCGAUUUCGUCAUCCUCCAUACCAUC GCCUUACCGUUCGCGUCAGACGACUCGCUGAGGAUCCGACA |
| 603 | 133 | GGAGGAGCUACGAUGCGGUGAAUUCUUCCGGCACUUUGUCAUCU UCACCCCAUGCUGCACAGACGACUCGCUGAGGAUCCGACA |
| 827 | 134 | GGAGGAGCUACGAUGCGGUGAAUUCUUCCGGCACUUUGUCAUCU UCGCCCCAUGCUGCACAGACGACUCGCUGAGGAUCCGACA |
| 1192 | 135 | GGAGGAGCUACGAUGCGGCAGGUGCGGGAUCUAAUGCGUAGACA GCCAUAUACUGACACAGACAGACGACUCGCUGAGGAUCCGACA |

TABLE 2-continued

Putative human islet specific aptamers isolated via cluster SELEX (from FIG. 1)

| aptamer name | SEQ ID NO. | sequence |
|---|---|---|
| 117 | 136 | GGAGGAGCUACGAUGCGGCCGUCUCGCUCUCAUCCCAUGCACGA ACCCUCUCUCACUGCACAGACGACUCGCUGAGGAUCCGACA |
| 448 | 137 | GGAGGAGCUACGAUGCGGCCGAUUGCGUCAUCCUCCAUACCAUC GCCUUACCGUUCCGCGUCAGACGACUCGCUGAGGAUCCGACA |
| 1739 | 138 | GGAGGAGCUACGAUGCGGUGAAUUCUUCCGGCACUUUGUCAUCU UCACCCCCAUGCUGCUCAGACGACUCGCUGAGGAUCCGACA |
| 576 | 139 | GGAGGAGCUACGAUGCGGCCGUCUCGCUCUCAUCCCAUGCACGA AACCUCUCUCACUGCGCAGACGACUCGCUGAGGAUCCGACA |
| 185 | 140 | GGAGGAGCUACGAUGCGGACGGAAGGAUAGUUGCUAAUCGAGCC CUGCCGACGCUUCAGACAGACGACUCGCUGAGGAUCCGACA |
| 2131 | 141 | GGAGGAGCUACGAUGCGGCAAAAACUGAUAAACACAGGUCCGGCA UUUGAGCGUACACCCAGACAGACGACUCGCUGAGGAUCCGACA |
| 823 | 142 | GGAGGAGCUACGAUGCGGUGAAUUCUUCCGGCACUUUGUCAUCU UCACCCCCGUGCUGCACAGACGACUCGCUGAGGAUCCGACA |
| 40 | 143 | GGAGGAGCUACGAUGCGGCCGAUUUCGUCAUCCUCCAUACCUCG CCUUACCGUUCCGCGUCAGACGACUCGCUGAGGAUCCGACA |
| 38 | 144 | GGAGGAGCUACGAUGCGGCCGAUUUCGUCAUCCUCCAUACCAUC GCCUUACCGUUCCGCCUCAGACGACUCGCUGAGGAUCCGACA |
| 560 | 145 | GGAGGAGCUACGAUGCGGCCCAUCACUCCCGCGUGUUGCGAACG CAUCGUUAUUUAGCCGUCAGACGACUCGCUGAGGAUCCGACA |
| 1183 | 146 | GGAGGAGCUACGAUGCGGCUUCCCUAUUCCAAAGGAGGUGCGGU ACGUUUUGUUACGCCAGACAGACGACUCGCUGAGGAUCCGACA |
| 435 | 147 | GGAGGAGCUACGAUGCGGCCGAUUUCGUCAUCCUCCAUACUAUC GCCCUACCGUUCCGCGUCAGACGACUCGCUGAGGAUCCGACA |
| 273 | 148 | GGAGGAGCUACGAUGCGGCCGAUUUCGUCAUCCUCCACACCAUC GCCUUACCGUUCCGCAUCAGACGACUCGCUGAGGAUCCGACA |
| 439 | 149 | GGAGGAGCUACGAUGCGGCCGAUUUCGUCAUCCUCCAUACCAUC GCCUUACCGUGCCGCGUCAGACGACUCGCUGAGGAUCCGACA |
| 1082 | 150 | GGAGGAGCUACGAUGCGGUGAAUUCUUCCGGCACCUUGUCAUCU UCACCCCCAUGCUGCACAGACGACUCGCUGAGGAUCCGACA |
| 321 | 151 | GGAGGAGCUACGAUGCGGUGUACCCUGAUUGCCUUUGUGUUAUG AGCGACAGAUCUGCCAGACAGACGACUCGCUGAGGAUCCGACA |
| 562 | 152 | GGAGGAGCUACGAUGCGGCCCACCACUCCCGCGUAUUGCGAACG CAUCGUUAUUUAGCCGUCAGACGACUCGCUGAGGAUCCGACA |
| 1735 | 153 | GGAGGAGCUACGAUGCGGUGAAUUCUUCCGGCACUUUGUCGUCU UCACCCCCAUGCUGCACAGACGACUCGCUGAGGAUCCGACA |
| 106 | 154 | GGAGGAGCUACGAUGCGGUACACUCAGUCACGUAGCACCGCAGU GACCCUUUGUACCGCAGACAGACGACUCGCUGAGGAUCCGACA |
| 1487 | 155 | GGAGGAGCUACGAUGCGGCCAGCCACACUUUGACCGAAUUGGCA AGCGCGGGCAAAUCGAACAGACGACUCGCUGAGGAUCCGACA |
| 581 | 156 | GGAGGAGCUACGAUGCGGCCGUCUCGCUCUCAUCCCAUGCACGA CACCUCUCUCACUGCACAGACGACUCGCUGAGGAUCCGACA |
| 1063 | 157 | GGAGGAGCUACGAUGCGGUCGUCUCGCUCUCAUCCCAUGCACGA AACCUCUCUCACUGCACAGACGACUCGCUGAGGAUCCGACA |
| 480 | 158 | GGAGGAGCUACGAUGCGGCCGAUUUCGUCAUCCUCCAUACCAUG CCUUACCGUUCCGCGUCAGACGACUCGCUGAGGAUCCGACA |
| 1061 | 159 | GGAGGAGCUACGAUGCGGCCGUCUCGCUCUCCUCCCAUGCACGA AACCUCUCUCACUGCACAGACGACUCGCUGAGGAUCCGACA |

TABLE 2-continued

Putative human islet specific aptamers isolated via cluster SELEX (from FIG. 1)

| aptamer name | SEQ ID NO. | sequence |
|---|---|---|
| 1479 | 160 | GGAGGAGCUACGAUGCGGGCUGUGCCGGCCCUGCUCUGGUCGC CAUUGUCAGUCUGUGCAGACAGACGACUCGCUGAGGAUCCGACA |
| 1392 | 161 | GGAGGAGCUACGAUGCGGUGAAUUCUCCCGGCACUUUGUCAUCU UCACCCCCAUGCUGCACAGACGACUCGCUGAGGAUCCGACA |
| 225 | 162 | GGAGGAGCUACGAUGCGGACCUUGUUUUUCCUCUGUACCCCACU UCCCCAUUUCUCCCUGCUCAGACGACUCGCUGAGGAUCCGACA |
| 1856 | 163 | GGAGGAGCUACGAUGCGGAUUAUUGUUUGACGUAUUCCAAGUGA GAUUACGCACGCACCAGACAGACGACUCGCUGAGGAUCCGACA |
| 269 | 164 | GGAGGAGCUACGAUGCGGCCGAUAUCGUCAUCCUCCAUACCAUC GCCUUACCGUCCCGCGUCAGACGACUCGCUGAGGAUCCGACA |
| 829 | 165 | GGAGGAGCUACGAUGCGGUGAAUUCUUCCGGCACUUUGUCAUCU UCCCCCCAUGCUGCACAGACGACUCGCUGAGGAUCCGACA |
| 800 | 166 | GGAGGAGCUACGAUGCGGCCGUCUCGCUCUUAUCCCAUGCACGA AACCUCUCUCACUGCACAGACGACUCGCUGAGGAUCCGACA |
| 389 | 167 | GGAGGAGCUACGAUGCGGUGAAUUCUUCCGGCACUUUGUCAUCU UCACCCUCAUGCUGCACAGACGACUCGCUGAGGAUCCGACA |
| 28 | 168 | GGAGGAGCUACGAUGCGGCCCAUCACUCCCGCGUAUUGCGAACG CAUCGUUGUUUAGCCGUCAGACGACUCGCUGAGGAUCCGACA |
| 1737 | 169 | GGAGGAGCUACGAUGCGGUGAAUUCUUCCGGCACUUUGUCAUCC UCACCCCCAUGCUGCACAGACGACUCGCUGAGGAUCCGACA |
| 1052 | 170 | GGAGGAGCUACGAUGCGGCCCAUCACUCCCACGUAUUGCGAACG CAUCGUUAUUUAGCCGUCAGACGACUCGCUGAGGAUCCGACA |
| 405 | 171 | GGAGGAGCUACGAUGCGGCCGAUUUCGUCAUCCUCCAUACCAUC GCCUUACCGUUCCGCGUCAGACGACUCGCUGAGGAUCCGACA |
| 317 | 172 | GGAGGAGCUACGAUGCGGGGAAGCAACACUUAGUCGGGAUUGAU ACGUGCCCAGUCAGCAGUCAGACGACUCGCUGAGGAUCCGACA |
| 1716 | 173 | GGAGGAGCUACGAUGCGGCCGAUCACUCCCGCGUAUUGCGAACG CAUCGUUAUUUAGCCGUCAGACGACUCGCUGAGGAUCCGACA |
| 623 | 174 | GGAGGAGCUACGAUGCGGCCGAAUUUCGUCAUCCUCCAUACCAU CGCCUUACCGUUCCGCGUCAGACGACUCGCUGAGGAUCCGACA |
| 305 | 175 | GGAGGAGCUACGAUGCGGCCGAUUUCGUCAUCCUCCAUACCAUC GCUUACCGUUCCGCGUCAGACGACUCGCUGAGGAUCCGACA |
| 686 | 176 | GGAGGAGCUACGAUGCGGCCGAUUUCGUCAUCCUCCAUACCAUC GCCCACCGUUCCGCGUCAGACGACUCGCUGAGGAUCCGACA |
| 151 | 177 | GGAGGAGCUACGAUGCGGCCGAUUUCGUCAUCCUCCAUACCAUC GCCUUACCGUUCCGUCAGACGACUCGCUGAGGAUCCGACA |
| 178 | 178 | GGAGGAGCUACGAUGCGGGGAAGCACCACUUAGUCGCGAUUGAU ACGUGCGCAGUCAUCAGACAGACGACUCGCUGAGGAUCCGACA |
| 1085 | 179 | GGAGGAGCUACGAUGCGGUGAAUUCUUCCGGCACUUUGUCAUCU UCACGCCCAUGCUGCACAGACGACUCGCUGAGGAUCCGACA |
| 1428 | 180 | GGAGGAGCUACGAUGCGGCCGAUUUCGUCAUCCUCCAAGCCAUC GCCUUACCGUUCCGCGUCAGACGACUCGCUGAGGAUCCGACA |
| 1401 | 181 | GGAGGAGCUACGAUGCGGUGAAUUCUUCCGACACUUUGUCAUCU UCACCCCCAUGCUGCACAGACGACUCGCUGAGGAUCCGACA |
| 1 | 182 | GGAGGAGCUACGAUGCGGGGAAGCCACACUUAGUCGCGAUUGAU ACGUGCGCAGUCAUCAGACAGACGACUCGCUGAGGAUCCGACA |
| 799 | 183 | GGAGGAGCUACGAUGCGGCCGUCUCGUUCUCAUCCCAUGCACGA AACCUCUCUCACUGCACAGACGACUCGCUGAGGAUCCGACA |

TABLE 2-continued

Putative human islet specific aptamers isolated via cluster SELEX (from FIG. 1)

| aptamer name | SEQ ID NO. | sequence |
|---|---|---|
| 98 | 184 | GGAGGAGCUACGAUGCGGACGGAGGAUAGUUGCUAAUCGAGCCCUGCCGACGCUUCAGUCAGACGACUCGCUGAGGAUCCGACA |
| 550 | 185 | GGAGGAGCUACGAUGCGGACGGUUUCACCUCUAGGAGCACUGAAAGCCAACCUUCGCGCACAGACGACUCGCUGAGGAUCCGACA |
| 2279 | 186 | GGAGGAGCUACGAUGCGGUGAAUUCCUCCGGCACUUUGUCAUCUUCACCCCCAUGCUGCACAGACGACUCGCUGAGGAUCCGACA |
| 2047 | 187 | GGAGGAGCUACGAUGCGGCCGAUUUCGUCAUCCUCCACAUCAUCGCCUUACCGUUCCGCGUCAGACGACUCGCUGAGGAUCCGACA |
| 490 | 188 | GGAGGAGCUACGAUGCGGCCGAUUUCGUCAUCCCCCAUACCAUCGCCUUACCUUCCGCGUCAGACGACUCGCUGAGGAUCCGACA |
| 606 | 189 | GGAGGAGCUACGAUGCGGUGAAUUCUUCCGGCACUUGUCAUCUUCACCCCCAUGCUGCACAGACGACUCGCUGAGGAUCCGACA |
| 2019 | 190 | GGAGGAGCUACGAUGCGGCCGUCUCGCUCUCAUCCCAUGCGCGAAACCUCUCUCACUGCACAGACGACUCGCUGAGGAUCCGACA |
| 1393 | 191 | GGAGGAGCUACGAUGCGGUGAAUUCUUCCGGCACUUUGUCAUCUUCACCCCUAUGCUGCACAGACGACUCGCUGAGGAUCCGACA |
| 678 | 192 | GGAGGAGCUACGAUGCGGCCGAUUUUCGUCAUCCUCCAUACCAUCGCCCUACCGUUCCGCGUCAGACGACUCGCUGAGGAUCCGACA |
| 1051 | 193 | GGAGGAGCUACGAUGCGGCCCAUCACUCCCGCGUAUUGCGAACGCAUCGUUAUUUAGCUGUCAGACGACUCGCUGAGGAUCCGACA |
| 109 | 194 | GGAGGAGCUACGAUGCGGCCCAUCGCUCCCGCGUAUUGCGAACGCAUCGUUAUUUAGCCGUCAGACGACUCGCUGAGGAUCCGACA |
| 145 | 195 | GGAGGAGCUACGAUGCGGCCGAUUUCGGCAUCCUCCACACCAUCGCCUUACCGUUCCGCGUCAGACGACUCGCUGAGGAUCCGACA |
| 469 | 196 | GGAGGAGCUACGAUGCGGCCGAUUUCGUCAUCCUCCAUCAUCGCCUUACCGUUCCGCGUCAGACGACUCGCUGAGGAUCCGACA |
| 1076 | 197 | GGAGGAGCUACGAUGCGGUGAACUCUUCCGGCACUUUGUCAUCUUCACCCCCAUGCUGCACAGACGACUCGCUGAGGAUCCGACA |
| 1373 | 198 | GGAGGAGCUACGAUGCGGCCCAUCACUCCCGCGUAUUGCGAACGCAUCGUUAUUCAGCCGUCAGACGACUCGCUGAGGAUCCGACA |
| 2272 | 199 | GGAGGAGCUACGAUGCGGCCGUCUCGCUCUCAUCCCAUGCACAAAACCUCUCUCACUGCACAGACGACUCGCUGAGGAUCCGACA |
| 1100 | 200 | GGAGGAGCUACGAUGCGGCCGAUUUCGUCAUCCCCCAUACCAUCGCCUUACCGUUCCGCAGUCAGACGACUCGCUGAGGAUCCGACA |
| 452 | 201 | GGAGGAGCUACGAUGCGGCCGAUUUCGUCAUCCUCCACACCAUCGCCUUACUGUUCCGCGUCAGACGACUCGCUGAGGAUCCGACA |
| 1720 | 202 | GGAGGAGCUACGAUGCGGCCGUCUCGCUCUCAUCCCAUGCACGAAAUCUCUCUCACUGCACAGACGACUCGCUGAGGAUCCGACA |
| 1374 | 203 | GGAGGAGCUACGAUGCGGCCCAUCACUCCCGCGUAUUGCGAACGCAUCGCUAUUUAGCCGUCAGACGACUCGCUGAGGAUCCGACA |
| 283 | 204 | GGAGGAGCUACGAUGCGGCCGAUUUCGUCAUCCUCAUACCAUCGCCUUACCGUUCCGCGUCAGACGACUCGCUGAGGAUCCGACA |
| 1724 | 205 | GGAGGAGCUACGAUGCGGACCUUGUUUCCCUCUGUACCCCACUUCCCCAUUUCUCCCUGCUCAGACGACUCGCUGAGGAUCCGACA |
| 1083 | 206 | GGAGGAGCUACGAUGCGGUGAAUUCUUCCGGCACUUUGUCAUCUCCACCCCCAUGCUGCACAGACGACUCGCUGAGGAUCCGACA |
| 2282 | 207 | GGAGGAGCUACGAUGCGGUCGAUUUCGUCAUCCUCCAUACCAUCGCCUUACUGUUCCGCGUCAGACGACUCGCUGAGGAUCCGACA |

TABLE 2-continued

Putative human islet specific aptamers isolated via cluster SELEX
(from FIG. 1)

| aptamer name | SEQ ID NO. | sequence |
|---|---|---|
| 663 | 208 | GGAGGAGCUACGAUGCGGCCGAUUUCGUCAUCCUCCAUACCAUC GUCUUACCUUUCCGCGUCAGACGACUCGCUGAGGAUCCGACA |
| 172 | 209 | GGAGGAGCUACGAUGCGGCCGAUUUCGUCAUCCUCCAUACCAUC GCCUUACGUUCCGCGUCAGACGACUCGCUGAGGAUCCGACA |
| 153 | 210 | GGAGGAGCUACGAUGCGGCCGAUUUCGUCAUCCUCCAUACCAUC GCCUUACCACUCCGCGUCAGACGACUCGCUGAGGAUCCGACA |
| 324 | 211 | GGAGGAGCUACGAUGCGGACGGAGGAUAGUUGCUAAUCGAGCCC UGCUGACGCUUCAGACAGACGACUCGCUGAGGAUCCGACA |
| 2132 | 212 | GGAGGAGCUACGAUGCGGUGUACACUGAUUGCCUUUGUGUUAUG GGCGACAGAUCUGCCAGACAGACGACUCGCUGAGGAUCCGACA |
| 1390 | 213 | GGAGGAGCUACGAUGCGGUGAAUCCUUCCGGCACUUUGUCAUCU UCACCCCCAUGCUGCACAGACGACUCGCUGAGGAUCCGACA |
| 1400 | 214 | GGAGGAGCUACGAUGCGGUGAAUUCUUCCGGCACUUUGCCAUCU UCACCCCCAUGCUGCACAGACGACUCGCUGAGGAUCCGACA |
| 1380 | 215 | GGAGGAGCUACGAUGCGGACCUCGUUUUCCUCUGUACCCCACUU CCCCAUUUCUCCCUGCUCAGACGACUCGCUGAGGAUCCGACA |
| 1721 | 216 | GGAGGAGCUACGAUGCGGCCGUCUCGCUCUCAUCCCAUGCACGA AACCUCUCUAACUGCACAGACGACUCGCUGAGGAUCCGACA |
| 375 | 217 | GGAGGAGCUACGAUGCGGCCGUCUCGCUCUCAUCCCAUGCACGA AACCUCCCUCACUGCACAGACGACUCGCUGAGGAUCCGACA |
| 1064 | 218 | GGAGGAGCUACGAUGCGGCCGUCUCGCUCUCAUCCCAUGCACGA AACCUCUCUCACCGCACAGACGACUCGCUGAGGAUCCGACA |
| 787 | 219 | GGAGGAGCUACGAUGCGGCCCAUCACUCCCGCGUAUCGCGAACG CAUCGUUAUUUAGCCGUCAGACGACUCGCUGAGGAUCCGACA |
| 848 | 220 | GGAGGAGCUACGAUGCGGCCGAUUUUUCGUCAUCCUCCAUACCA UCGCCUUACCGUUCCGCGUCAGACGACUCGCUGAGGAUCCGACA |
| 575 | 221 | GGAGGAGCUACGAUGCGGCCGUCUCGCUCUCAUCCCAUGCACGA AACCCCUCUCACUGCACAGACGACUCGCUGAGGAUCCGACA |
| 240 | 222 | GGAGGAGCUACGAUGCGGCAGAUUUCGUCAUCAUCCAUACCAUC GCCUUACCGUUCCGCGUCAGACGACUCGCUGAGGAUCCGACA |
| 210 | 223 | GGAGGAGCUACGAUGCGGCCCAUCACUCCCGCGCACUGCGAACG CAUCGUUAUUUAGCCGUCAGACGACUCGCUGAGGAUCCGACA |
| 351 | 224 | GGAGGAGCUACGAUGCGGCCCAUCCCUCCCGCGUAUUGCGAACG CCUCGUUAUUUAGCCGUCAGACGACUCGCUGAGGAUCCGACA |
| 554 | 225 | GGAGGAGCUACGAUGCGGAAUCUCCCGAACGCAUUAGUCAGUCC CAUACCCGUGUGCCGCGUCAGACGACUCGCUGAGGAUCCGACA |
| 789 | 226 | GGAGGAGCUACGAUGCGGCCCAUCACUCCCGUGUAUUGCGAACG CAUCGUUAUUUAGCCGUCAGACGACUCGCUGAGGAUCCGACA |
| 288 | 227 | GGAGGAGCUACGAUGCGGCCGAUUUCGUCAUCCUCCAACCAUCG CCUUACCGUUCCGCGUCAGACGACUCGCUGAGGAUCCGACA |
| 785 | 228 | GGAGGAGCUACGAUGCGGCCCAUCACUCCCGCGUAUUGCGAACG CAUCGUUAUCUAGCCGUCAGACGACUCGCUGAGGAUCCGACA |
| 1430 | 229 | GGAGGAGCUACGAUGCGGACGAUUUCGUCAUCCUCCAUACCAUC GCCUUACCGUUCCGAGUCAGACGACUCGCUGAGGAUCCGACA |
| 1053 | 230 | GGAGGAGCUACGAUGCGGCCCAUCACUCCCGCGUAUUGCGAACG UAUCGUUAUUUAGCCGUCAGACGACUCGCUGAGGAUCCGACA |
| 2158 | 231 | GGAGGAGCUACGAUGCGGAUUACCAACUUGAACGCCGAGAGUGU GGUCAUGUGUUCUGCAGACAGACGACUCGCUGAGGAUCCGACA |

TABLE 2-continued

Putative human islet specific aptamers isolated via cluster SELEX (from FIG. 1)

| aptamer name | SEQ ID NO. | sequence |
| --- | --- | --- |
| 892 | 232 | GGAGGAGCUACGAUGCGGCCGAUUUUCGUCAUCCUCCAUGCCAU CGCCUUACCGUUCCGCGUCAGACGACUCGCUGAGGAUCCGACA |
| 596 | 233 | GGAGGAGCUACGAUGCGGUGGAUUCUUCCGGCACUUUGUCAUCU UCACCCCCAUGCUGCACAGACGACUCGCUGAGGAUCCGACA |
| 454 | 234 | GGAGGAGCUACGAUGCGGCCGAUUUCGUCAUCCUCCACACCAUC GCCUUACCCUUCCGCGUCAGACGACUCGCUGAGGAUCCGACA |
| 1763 | 235 | GGAGGAGCUACGAUGCGGCCGAUUUCGUCAUCCUCCAUACCAUC GUCUUACCGUUCUGCGUCAGACGACUCGCUGAGGAUCCGACA |
| 605 | 236 | GGAGGAGCUACGAUGCGGUGAAUUCUUCCGGCACUUUGUCAUCU UCACCCCCAUGCUGCACAGACGACUCGCUGAGGAUCCGACA |
| 1073 | 237 | GGAGGAGCUACGAUGCGGACCUUGUUUUCCUCUGUACCCCACUU CCCAUUUCUCCCUGCUCAGACGACUCGCUGAGGAUCCGACA |
| 791 | 238 | GGAGGAGCUACGAUGCGGCCCAUCACUCCCGCGUAUUGCGAGCG CAUCGUUAUUUAGCCGUCAGACGACUCGCUGAGGAUCCGACA |
| 77 | 239 | GGAGGAGCUACGAUGCGGCCGAUUUCGUCAUCCUCCAUACCAUC GCCUUACCGUUCCGAGACAGACGACUCGCUGAGGAUCCGACA |
| 568 | 240 | GGAGGAGCUACGAUGCGGCCCAUCACUCCCGCGAAUUGCGAACG CAUCGUUAUUUAGCCGUCAGACGACUCGCUGAGGAUCCGACA |
| 803 | 241 | GGAGGAGCUACGAUGCGGCCGUCUCGCUCCCAUCCCAUGCACGA AACCUCUCUCACUGCACAGACGACUCGCUGAGGAUCCGACA |
| 571 | 242 | GGAGGAGCUACGAUGCGGCCCAUCACUCCCGCGUAUUGCGAACG CAUCGUUAUUAGCCGUCAGACGACUCGCUGAGGAUCCGACA |
| 585 | 243 | GGAGGAGCUACGAUGCGGACCUUGUUUUCCUCCGUACCCCACUU CCCCAUUUCUCCCUGCUCAGACGACUCGCUGAGGAUCCGACA |
| 851 | 244 | GGAGGAGCUACGAUGCGGCUGAUUUCGUCAUCCCCCAUACCAUC GCCUUACCGUUCCGCGUCAGACGACUCGCUGAGGAUCCGACA |
| 601 | 245 | GGAGGAGCUACGAUGCGGUGAAUUCUUCCGGCACUUUGUCAUCU UCACCCCCAUGCGGCACAGACGACUCGCUGAGGAUCCGACA |
| 706 | 246 | GGAGGAGCUACGAUGCGGACGGAGGAUAGUUGCUAAUCGAGCCC UGCGGACGCUUCAGACAGACGACUCGCUGAGGAUCCGACA |
| 1391 | 247 | GGAGGAGCUACGAUGCGGUGAAUUCUUCCGGCACUUUGUCAUCU UCACCCCCAGGCUGCACAGACGACUCGCUGAGGAUCCGACA |
| 471 | 248 | GGAGGAGCUACGAUGCGGCCGAUUUCGUAUCCUCCGUACCAUCG CCUUACCGUUCCGCGUCAGACGACUCGCUGAGGAUCCGACA |
| 116 | 249 | GGAGGAGCUACGAUGCGGCCGUCUCGAUCUCAUCCCAUGCACGA AACCUCUCUCACUGCACAGACGACUCGCUGAGGAUCCGACA |
| 47 | 250 | GGAGGAGCUACGAUGCGGCCGAUUUCGUCAUCCUCCAUACCAUC GCCUCCGUUCCGCGUCAGACGACUCGCUGAGGAUCCGACA |

Figure 2:
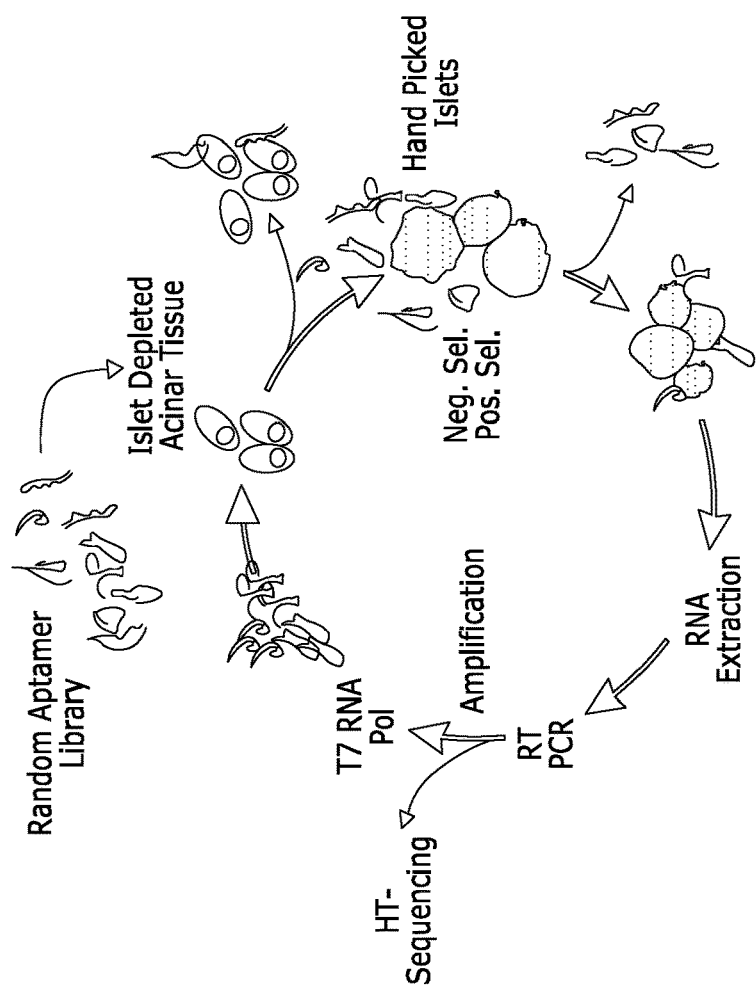
FIG. 2 is a flow chart showing HT-Toggle-cluster SELEX to isolate islets specific aptamers crossreacting between mouse and human.
Figure 2:
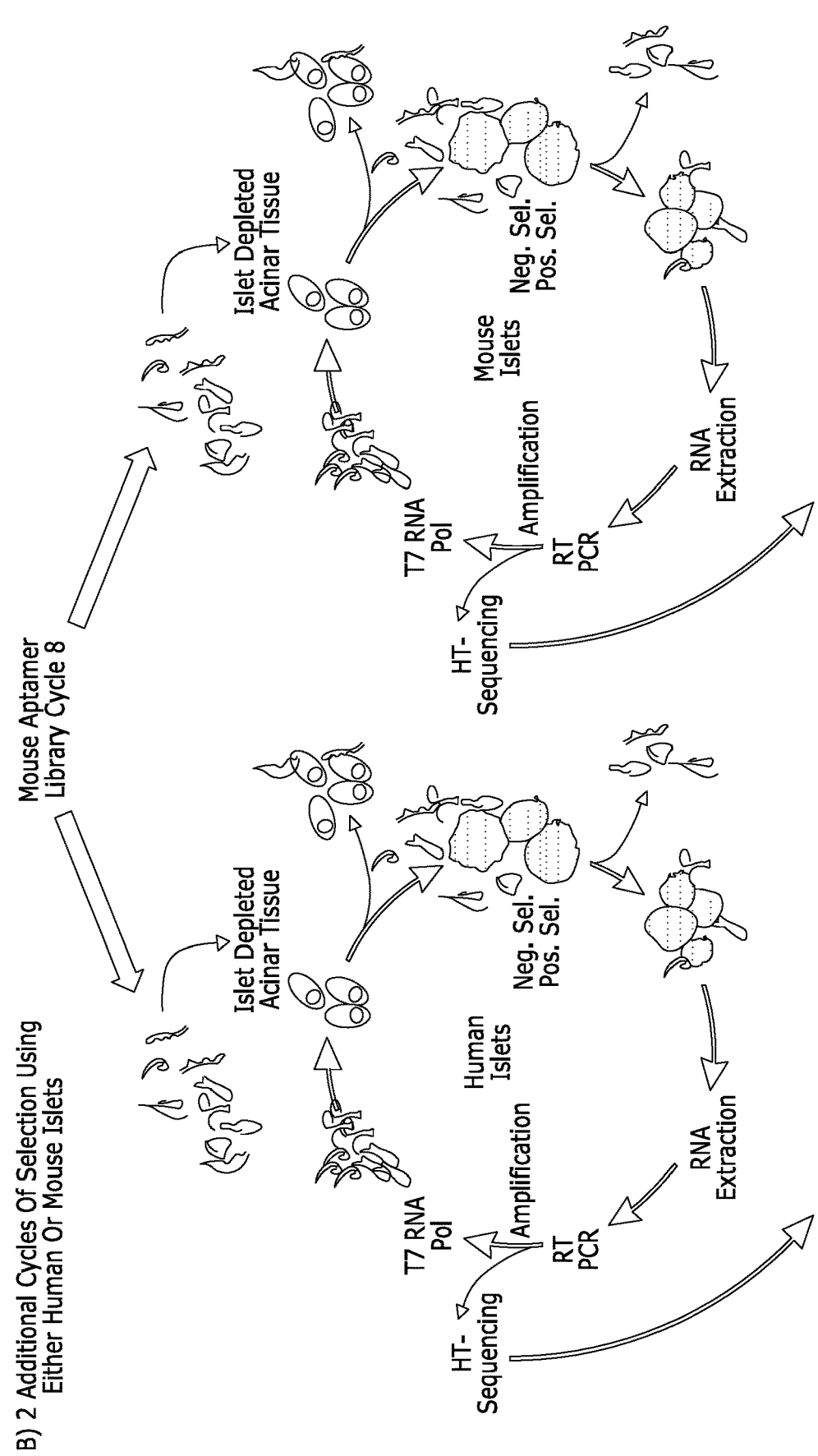
Figure 2:
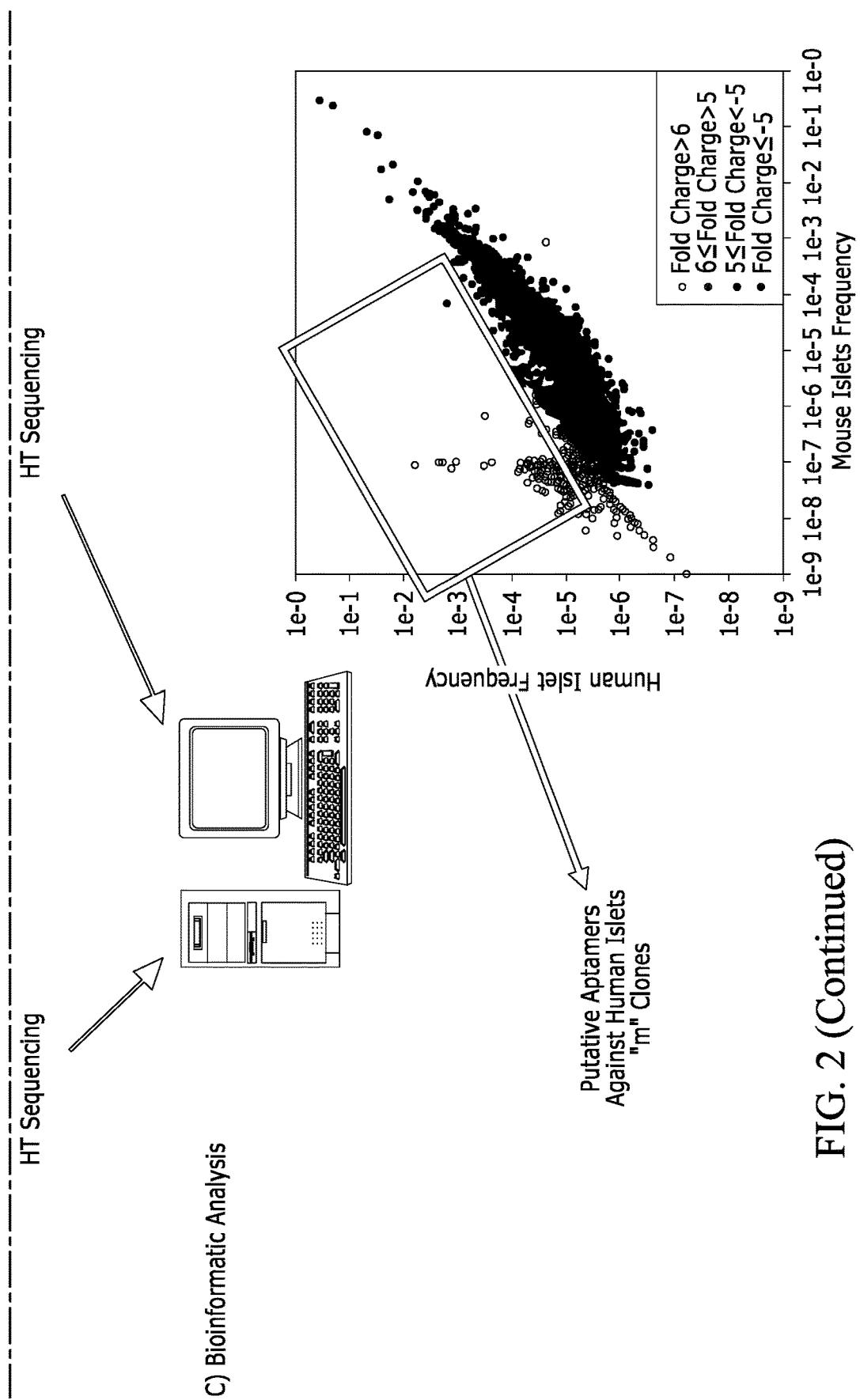
Figure 3:
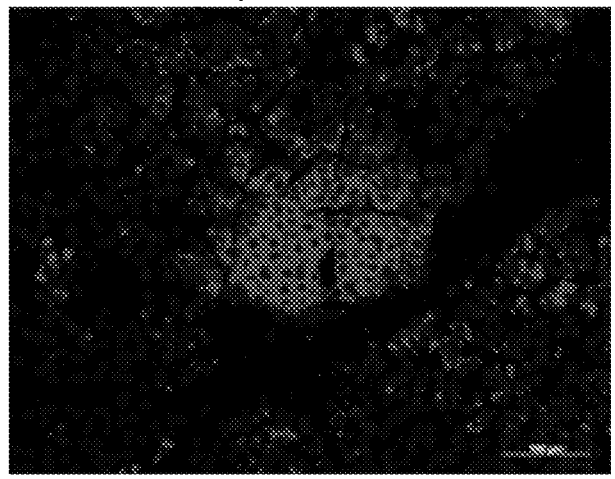
FIG. 3 shows images resulting from HT-Toggle-cluster SELEX to isolate islets specific aptamers crossreacting between mouse and human.
Figure 3:
Figure 3:

As shown in FIG. 2, HT-Toggle-cluster SELEX was used to isolate islet-specific aptamers crossreacting between mouse and human. 8 cycles of HT-cluster SELEX were performed as described in FIG. 1 using as negative and positive selectors mouse acinar tissues and mouse islets respectively (FIG. 2A). The resulting polyclonal aptamer from cycle 8 was used for two additional cycle of selection using either acinar tissue and islets from mice or acinar tissue and islets isolated from cadaveric donors (FIG. 2B). The resulting polyclonal aptamer library underwent HT-sequencing and bio-informatic analysis (FIG. 2C) to determine the frequency of each monoclonal aptamer present in the library selected using mouse or human tissues. Monoclonal aptamers (Table 3) enriched in the human library (putative aptamers against human islets, rectangular selection) were chosen for empirical testing. Table 3 provides also putative aptamers against human islets.

Table 3—aptamer sequences specific for human islets

TABLE 3 aptamers specific for human islets

| name | SEQ ID NO: | Sequence |
|---|---|---|
| 166-279 | 251 | GGAGGACGAUGCGGCCGAUUUCGUCAUCCUCCAUACC AUCGCCUUACCGUUCCGCGUCAGACGACUCGCUGAGG AUCCGAGA |
| 109-2031 | 252 | GGAGGACGAUGCGGUGAAUUCUUCCGGCACUUUGUCA UCUUCACCCCCAUGCUGCACAGACGACUCGCUGAGGAU CCGAGA |
| 208-2529 | 253 | GGAGGACGAUGCGGCCGUCUCGCUCUCAUCCCAUGCA CGAAACCUCUCUCACUGCACAGACGACUCGCUGAGGAU CCGAGA |
| 64-2437 | 254 | GGAGGACGAUGCGGCCCAUCACUCCCGCGUAUUGCGA ACGCAUCGUUAUUUAGCCGUCAGACGACUCGCUGAGG AUCCGAGA |
| 173-2273 | 255 | GGAGGACGAUGCGGACCUUGUUUUCCUCUGUACCCCA CUUCCCCAUUUCUCCCUGCUCAGACGACUCGCUGAGGA UCCGAGA |

TABLE 3-continued aptamers specific for human islets

| name | SEQ ID NO: | Sequence |
|---|---|---|
| 12-2617 | 256 | GGAGGACGAUGCGGUGUACACUGAUUGCCUUUGUGU UAUGAGCGACAGAUCUGCCAGACGACUCGCUGAGGAU CCGAGA |
| 107-901 | 257 | GGAGGACGAUGCGGGGAAGCAACACUUAGUCGCGAUU GAUACGUGCGCAGUCAUCAGACGACUCGCUGAGGAUC CGAGA |
| 155-1103 | 258 | GGAGGACGAUGCGGCCGAUUUUCGUCAUCCUCCAUAC CAUCGCCUUACCGUUCCCAGACGACUCGCUGAGGAUCC GAGA |
| 1-717 | 259 | GGAGGACGAUGCGGUAAUUCUCAGGAGGUGCGGAAC GGGAUAUGGAUUGUUCGCCAGACGACUCGCUGAGGAU CCGAGA |
| m1-2623 | 260 | GGAGGACGAUGCGGUACACUCAGUCACGUAGCACCGC AGUGACCCUUUGUACCGCAGACGACUCGCUGAGGAUC CGAGA |
| m5-3229 | 261 | GGAGGACGAUGCGGCCUAGUACAAAAGCCUGAUCUCU GUGAGCAGACACUAGAACAGACGACUCGCUGAGGAUC CGAGA |
| m7-2539 | 262 | GGAGGACGAUGCGGAUUACCAACUUGAACGCCGAGAG UGUGGUCACGUGUUCUGCAGACGACUCGCUGAGGAUC CGAGA |
| m9-3076 | 263 | GGAGGACGAUGCGGGGAAGCAACACUUAGUCGCGAUU GAUACGUGCGCAGUCAUCAGACGACUCGCUGAGGAUC CGAGA |
| m12-3773 | 264 | GGAGGACGAUGCGGCAACAAACUAAUCAGACACGAGAC AGAGAGAUAGAUCUGCCAGACGACUCGCUGAGGAUCC GAGA |
| m24-3219 | 265 | GGAGGACGAUGCGGCAGGUGCGGGAUCUAAUGCGUA GACAGCCAUAUACUGACACAGACGACUCGCUGAGGAUC CGAGA |

Table 4. Putative human islet specific aptamers isolated via toggle-clueseter SELEX (from FIG. 2)

TABLE 4

Putative human islet specific aptamers isolated via toggle-cluster SELEX (from FIG. 2)

| aptamer name | SEQ ID NO: | sequence |
|---|---|---|
| m2-1 | 266 | GGAGGAGCUACGAUGCGGCAGGUGCGGGGUCUAAUGCGUAGACAG CCAUAUACUGACACAGACAGACGACUCGCUGAGGAUCCGACA |
| m2-2 | 267 | GGAGGAGCUACGAUGCGGCAGGGGCGGGGUCUAAUGCGUAGACAG CCAUAUACUGACACAGACAGACGACUCGCUGAGGAUCCGACA |
| m322-3 | 268 | GGAGGAGCUACGAUGCGGGGAAGCAACACUUAGUCGCGAUUGAUGC GUGCGCAGUCAUCAGACAGACGACUCGCUGAGGAUCCGACA |
| m323-4 | 269 | GGAGGAGCUACGAUGCGGGGAAGCAACACUUAGUCGCGAUUGAUAU GUGCGCAGUCAUCAGACAGACGACUCGCUGAGGAUCCGACA |
| m630-5 | 270 | GGAGGAGCUACGAUGCGGGGAAGCAACACUUAGUCGCGAUUGAUAC GUGCGUAGUCAUCAGACAGACGACUCGCUGAGGAUCCGACA |
| m631-6 | 271 | GGAGGAGCUACGAUGCGGGGAAGCAACACUUAGUCGCGAUUGGUAC GUGCGCAGUCAUCAGACAGACGACUCGCUGAGGAUCCGACA |
| m635-7 | 272 | GGAGGAGCUACGAUGCGGGGAAGCAACACUUAGUCGCGAUUGAUAC GUGCGCGGUCAUCAGACAGACGACUCGCUGAGGAUCCGACA |

TABLE 4-continued

Putative human islet specific aptamers isolated via toggle-cluster SELEX (from FIG. 2)

| aptamer name | SEQ ID NO: | sequence |
|---|---|---|
| m636-8 | 273 | GGAGGAGCUACGAUGCGGGGAAGCAACGCUUAGUCGCGAUUGAUACGUGCGCAGUCAUCAGACAGACGACUCGCUGAGGAUCCGACA |
| m685-9 | 274 | GGAGGAGCUACGAUGCGGUAAUUCUCAGGAGGUGCGGAACGGGAUAUGGUUUGUUCGCCAGUCAGACGACUCGCUGAGGAUCCGACA |
| m703-10 | 275 | GGAGGAGCUACGAUGCGGUAAUUCUCAGGAGGUGCGGAACGGGAUAUGGAUUGUCCGCCAGUCAGACGACUCGCUGAGGAUCCGACA |
| m705-11 | 276 | GGAGGAGCUACGAUGCGGUAAUUCUCAGGAGGUGCGGAACGGGAUAUGGAAUGUUCGCCAGUCAGACGACUCGCUGAGGAUCCGACA |
| m706-12 | 277 | GGAGGAGCUACGAUGCGGUAAUUCUCAGGAGGUGCGGAGCGGGAUAUGGAUUGUUCGCCAGUCAGACGACUCGCUGAGGAUCCGACA |
| m1024-13 | 278 | GGAGGAGCUACGAUGCGGACCAUCGCUCCCGCGUAUUGCGAACGCAUCGUUAUUUAGCCGUCAGACGACUCGCUGAGGAUCCGACA |
| m1028-14 | 279 | GGAGGAGCUACGAUGCGGCCCAUCACUCCCGCGUAUUGCGUACGCAUCGUUAUUUAGCCGUCAGACGACUCGCUGAGGAUCCGACA |
| m1146-15 | 280 | GGAGGAGCUACGAUGCGGCCGGAGGCAGUCACUAAUCUUCACUUCCCUUAGACAUGCGCAGACAGACGACUCGCUGAGGAUCCGACA |
| m1157-16 | 281 | GGAGGAGCUACGAUGCGGGGAAGCAACACUUAGUCGCGAUUGAUACGUGUGCAGUCAUCAGACAGACGACUCGCUGAGGAUCCGACA |
| m1161-17 | 282 | GGAGGAGCUACGAUGCGGGGAAGCAACAUUUAGUCGCGAUUGAUACGUGCGCAGUCAUCAGACAGACGACUCGCUGAGGAUCCGACA |
| m1164-18 | 283 | GGAGGAGCUACGAUGCGGGGAGGCAACACUUAGUCGCGAUUGAUACGUGCGCAGUCAUCAGACAGACGACUCGCUGAGGAUCCGACA |
| m1164-19 | 284 | GGAGGAGCUACGAUGCGGGGGAGCAACACUUAGUCGCGAUUGAUACGUGCGCAGUCAUCAGACAGACGACUCGCUGAGGAUCCGACA |
| m1166-20 | 285 | GGAGGAGCUACGAUGCGGGGAAGCAAUACUUAGUCGCGAUUGAUACGUGCGCAGUCAUCAGACAGACGACUCGCUGAGGAUCCGACA |
| m1170-21 | 286 | GGAGGAGCUACGAUGCGGGGAAGCAACACUUAGUCGGGAUUGAUACGUGCCCAGUCAUCAGACAGACGACUCGCUGAGGAUCCGACA |
| m1200-22 | 287 | GGAGGAGCUACGAUGCGGCCGUCUCGCUCUCAUCCCAUGCACGACACCUCUCUCACUGCACAGACGACUCGCUGAGGAUCCGACA |
| m1233-23 | 288 | GGAGGAGCUACGAUGCGGUAAUUCUCAGGAGGUACGGAACGGGAUAUGGAUUGUUCGCCAGUCAGACGACUCGCUGAGGAUCCGACA |
| m1234-24 | 289 | GGAGGAGCUACGAUGCGGUAAUUCUCAGGAGGUGCGGAACGGGAUAUGGAUGGUUCGCCAGUCAGACGACUCGCUGAGGAUCCGACA |
| m1246-25 | 290 | GGAGGAGCUACGAUGCGGUAAUUCUCAGGAGGUGCGGAACGGGAUAUGGGUUGUUCGCCAUACAGACGACUCGCUGAGGAUCCGACA |
| m1259-26 | 291 | GGAGGAGCUACGAUGCGGUAAUUCCCAGGAGGUGCGGAACGGGAUAUGGAUUGUUCGCCAGUCAGACGACUCGCUGAGGAUCCGACA |
| m1260-27 | 292 | GGAGGAGCUACGAUGCGGUAAUUCACAGGAGGUGCGGAACGGGAUAUGGAUUGUUCGCCAGUCAGACGACUCGCUGAGGAUCCGACA |
| m1303-28 | 293 | GGAGGAGCUACGAUGCGGCCGAUUGCGUCAUCCUCCAUACCAUCGCCUUACCGUUCCGCGUCAGACGACUCGCUGAGGAUCCGACA |
| m1617-29 | 294 | GGAGGAGCUACGAUGCGGCCCAUCACUCACGCGUAGUGCGAACGCAUCGUUAUUUAGCCGUCAGACGACUCGCUGAGGAUCCGACA |
| m1684-30 | 295 | GGAGGAGCUACGAUGCGGUGUACACUGAUUGCCUUUGGGUUAAGAGCGACAGAUCCGGCAGACAGACGACUCGCUGAGGAUCCGACA |
| m1721-31 | 296 | GGAGGAGCUACGAUGCGGGGAAGCGACACUUAGUCGCGAUUGAUACGUGCGCAGUCAUCAGACAGACGACUCGCUGAGGAUCCGACA |
| m1723-32 | 297 | GGAGGAGCUACGAUGCGGGGAAGCAACACUUAGUCGGGAUUGAUACGUGCCCAGUCAGCAGACAGACGACUCGCUGAGGAUCCGACA |

TABLE 4-continued

Putative human islet specific aptamers isolated via
toggle-cluster SELEX (from FIG. 2)

| aptamer name | SEQ ID NO: | sequence |
|---|---|---|
| m1793-33 | 298 | GGAGGAGCUACGAUGCGGUAAUUCUCAGGAGGCGCGGAACGGGAU<br>AUGGAUUGUUCGCCAGUCAGACGACUCGCUGAGGAUCCGACA |
| m1794-34 | 299 | GGAGGAGCUACGAUGCGGUAAUUCUCAGGAGGAGCGGAACGGGAU<br>AUGGAUUGUUCGCCAGUCAGACGACUCGCUGAGGAUCCGACA |
| m1800-35 | 300 | GGAGGAGCUACGAUGCGGUAAUUCUCAGGAGGUGCGGAACGGGAU<br>ACGGAUUGUUCGCCAGUCAGACGACUCGCUGAGGAUCCGACA |
| m1800-36 | 301 | GGAGGAGCUACGAUGCGGUAAUUCUCAGGAGGUGCGGAACGGGAU<br>AAGGAUUGUUCGCCAGUCAGACGACUCGCUGAGGAUCCGACA |
| m1808-37 | 302 | GGAGGAGCUACGAUGCGGUAAUUCUCAGGAGGUGCGGAACGGGAU<br>AUGGAUUGCUCGCCAGUCAGACGACUCGCUGAGGAUCCGACA |
| m1809-38 | 303 | GGAGGAGCUACGAUGCGGUAAUUCUCAGGAGGUGCGGAACGGGAU<br>AUGGAUUAUUCGCCAGUCAGACGACUCGCUGAGGAUCCGACA |
| m1810-39 | 304 | GGAGGAGCUACGAUGCGGUAAUUCUCAGGAGGUGCGGAACGGGAU<br>AUGGAUUGUGCGCCAGUCAGACGACUCGCUGAGGAUCCGACA |
| m1811-40 | 305 | GGAGGAGCUACGAUGCGGUAAUUCUCAGGAGGUGCGGAACGGGAU<br>AUGGAUUGUACGCCAGUCAGACGACUCGCUGAGGAUCCGACA |
| m1812-41 | 306 | GGAGGAGCUACGAUGCGGUAAUUCUCAGGAGGUGCGGAACGGGAU<br>AUGGAUUGUUCGCAAGUCAGACGACUCGCUGAGGAUCCGACA |
| m1820-42 | 307 | GGAGGAGCUACGAUGCGGUAAUUCUCAGGAGGUGCGGAAUGGGAU<br>AUGGAUUGUUCGCCAGUCAGACGACUCGCUGAGGAUCCGACA |
| m1823-43 | 308 | GGAGGAGCUACGAUGCGGUAAUUCGCAGGAGGUGCGGAACGGGAU<br>AUGGAUUGUUCGCCAGACAGACGACUCGCUGAGGAUCCGACA |
| m2124-44 | 309 | GGAGGAGCUACGAUGCGGCCCAUCACUCCCGCGUAUUGCGACCGCA<br>UCGUUAUUUAGCCGUCAGACGACUCGCUGAGGAUCCGACA |
| m2149-45 | 310 | GGAGGAGCUACGAUGCGGAUUACCAACUUGAACGCCGAAAGUGGGG<br>UCACGUUUUCCGCAGACAGACGACUCGCUGAGGAUCCGACA |
| m2219-46 | 311 | GGAGGAGCUACGAUGCGGGGAAGCAACACUUAGUCGCGAUUGAUAC<br>GUGCGCAGUCAUCGGACAGACGACUCGCUGAGGAUCCGACA |
| m2272-47 | 312 | GGAGGAGCUACGAUGCGGUAAUUCUCAGGUGGUGCGGAACGGGAU<br>AUGGAUUGUUCGCCAGUCAGACGACUCGCUGAGGAUCCGACA |
| m2284-48 | 313 | GGAGGAGCUACGAUGCGGUGAUUCUCAGGAGGUGCGGAACGGGAU<br>AUGGAUUGUUCGCCAGUCAGACGACUCGCUGAGGAUCCGACA |
| m2288-49 | 314 | GGAGGAGCUACGAUGCGGUAAUUCUCAGGAGGUGCGGAACGGGAU<br>AUGGGUUGUUCGCCAGUCAGACGACUCGCUGAGGAUCCGACA |
| m2502-50 | 315 | GGAGGAGCUACGAUGCGGCCCAUCACUCCCGCGUAUUGCGAACGCA<br>UCGUUAUUUAGCCAGACAGACGACUCGCUGAGGAUCCGACA |
| m2514-51 | 316 | GGAGGAGCUACGAUGCGGCCCAUCACUCACGCGAAUUGCGAACGCA<br>UCGUUAUUUAGCCGUCAGACGACUCGCUGAGGAUCCGACA |
| m2548-52 | 317 | GGAGGAGCUACGAUGCGGCGCAUCACUCCCGCGUAUUGCGAACGCA<br>UCGUUAUUUAGCCGUCAGACGACUCGCUGAGGAUCCGACA |
| m2569-53 | 318 | GGAGGAGCUACGAUGCGGAUUACCAACUUGAACGCCGAGAGUGUGG<br>UCACGUGUUCUGCAGACAGACGACUCGCUGAGGAUCCGACA |
| m2578-54 | 319 | GGAGGAGCUACGAUGCGGCACAUACUGACAAUGGUUACCAGAGCAG<br>GUCCGGCACAUCCAGACAGACGACUCGCUGAGGAUCCGACA |
| m2581-55 | 320 | GGAGGAGCUACGAUGCGGUUACGCGUUUAAGUCAUUGACGCGUUAC<br>ACUGGAGGGGGCCAGACAGACGACUCGCUGAGGAUCCGACA |
| m2623-56 | 321 | GGAGGAGCUACGAUGCGGUACACUCAGUCACGUAGCACCGCAGUGA<br>CCCUUUGUACCGCAGACAGACGACUCGCUGAGGAUCCGACA |

TABLE 4-continued

Putative human islet specific aptamers isolated via toggle-cluster SELEX (from FIG. 2)

| aptamer name | SEQ ID NO: | sequence |
|---|---|---|
| m2675-57 | 322 | GGAGGAGCUACGAUGCGGGGAAGCAACACUUAGUCGUGAUUGAUACGUGCGCAGUCAUCAGACAGACGACUCGCUGAGGAUCCGACA |
| m2708-58 | 323 | GGAGGAGCUACGAUGCGGUAAUUCUCGGGAGGUGCGGAACGGGAUAUGGAUUGUUCGCCAGUCAGACGACUCGCUGAGGAUCCGACA |
| m2715-59 | 324 | GGAGGAGCUACGAUGCGGUAAUUCUCAGGAGGUGCAGAACGGGAUAUGGAUUGUUCGCCAGUCAGACGACUCGCUGAGGAUCCGACA |
| m2726-60 | 325 | GGAGGAGCUACGAUGCGGUAAUUCUCAGGAGGUGCGGAACGGGAUAUGGAUUGUUGGCCAGUCAGACGACUCGCUGAGGAUCCGACA |
| m2728-61 | 326 | GGAGGAGCUACGAUGCGGUAAUUCUCAGGAGGUGCGGAACGGGAUAUGGAUUGUUAGCCAGUCAGACGACUCGCUGAGGAUCCGACA |
| m2856-62 | 327 | GGAGGAGCUACGAUGCGGCGGAUCACUCCCGCGUAUUGCGAACGCAUCGUUAUUUAGCCGUCAGACGACUCGCUGAGGAUCCGACA |
| m2908-63 | 328 | GGAGGAGCUACGAUGCGGCCCAUCACUCCCGCGUAUUGCGAACGCAUCGUUAUUGAGCCGUCAGACGACUCGCUGAGGAUCCGACA |
| m2913-64 | 329 | GGAGGAGCUACGAUGCGGCCCAUCACUCGCGCGUAUUGCGAACGCAUAGUUAUUUAGCCGUCAGACGACUCGCUGAGGAUCCGACA |
| m2929-65 | 330 | GGAGGAGCUACGAUGCGGCAACAAACUAAUCAGACACGAGGCAGAAAGAUAGGUCCGGCAGACAGACGACUCGCUGAGGAUCCGACA |
| m2951-66 | 331 | GGAGGAGCUACGAUGCGGUGUAGCGAGAAUCGCGUUGUUGGGUGGUCUGUUGUCAGACGACUCGCUGAGGAUCCGACA |
| m3075-67 | 332 | GGAGGAGCUACGAUGCGGGGAAGCAACACUUAGUCGCGAUUGAUACGUGCGCAGUUAUCAGACAGACGACUCGCUGAGGAUCCGACA |
| m3076-68 | 333 | GGAGGAGCUACGAUGCGGGGAAGCAACACUUAGUCGCGAUUGAUACGUGCGCAGUCAUCAGACAGACGACUCGCUGAGGAUCCGACA |
| m3076-69 | 334 | GGAGGAGCUACGAUGCGGUGAAGCAACACUUAGUCGCGAUUGAUACGUGCGCAGUCAUCAGACAGACGACUCGCUGAGGAUCCGACA |
| m3076-70 | 335 | GGAGGAGCUACGAUGCGGGGAAGCAACACUUGGUCGCGAUUGAUACGUGCGCAGUCAUCAGACAGACGACUCGCUGAGGAUCCGACA |
| m3076-71 | 336 | GGAGGAGCUACGAUGCGGGGAAGCAACACUUAGUCGCGAUUGAUACGUGCGCAGUCAUCAGGCAGACGACUCGCUGAGGAUCCGACA |
| m3076-72 | 337 | GGAGGAGCUACGAUGCGGGAAGCAACACUUAGUCGCGAUUGAUACGUGCGCAGUCAUCAGACAGACGACUCGCUGAGGAUCCGACA |
| m3076-73 | 338 | GGAGGAGCUACGAUGCGGGGAAGCAGCACUUAGUCGCGAUUGAUACGUGCGCAGUCAUCAGACAGACGACUCGCUGAGGAUCCGACA |
| m3078-74 | 339 | GGAGGAGCUACGAUGCGGGGAAGUAACACUUAGUCGCGAUUGAUACGUGCGCAGUCAUCAGACAGACGACUCGCUGAGGAUCCGACA |
| m3092-75 | 340 | GGAGGAGCUACGAUGCGGUAACUCUCAGGAGGUGCGGAACGGGAUAUGGAUUGUUCGCCAGUCAGACGACUCGCUGAGGAUCCGACA |
| m3100-76 | 341 | GGAGGAGCUACGAUGCGGUAAUUCUCAGGAGGUGUGGAACGGGAUAUGGAUUGUUCGCCAGUCAGACGACUCGCUGAGGAUCCGACA |
| m3101-77 | 342 | GGAGGAGCUACGAUGCGGUAAUUCUCAGGAGGUGCGGAACGGGUUAUGGAUUGUUCGCCAGUCAGACGACUCGCUGAGGAUCCGACA |
| m3104-78 | 343 | GGAGGAGCUACGAUGCGGUAAUUCUCAGGAGGUGCGGAACGGGAUAUGGAUUGUCGCGAGUCAGACGACUCGCUGAGGAUCCGACA |
| m3117-79 | 344 | GGAGGAGCUACGAUGCGGCCGAUUUCGUCAUGCUCCAUACCAUCGCCUUACCGUUCCGCGUCAGACGACUCGCUGAGGAUCCGACA |
| m3211-80 | 345 | GGAGGAGCUACGAUGCGGCCCAUCACUCGCGCGUAUUGCGAACGCAUCGUUAUUUAGCCGUCAGACGACUCGCUGAGGAUCCGACA |

TABLE 4-continued

Putative human islet specific aptamers isolated via toggle-cluster SELEX (from FIG. 2)

| aptamer name | SEQ ID NO: | sequence |
|---|---|---|
| m3219-81 | 346 | GGAGGAGCUACGAUGCGGCAGGUGCGGGAUCUAAUGCGUAGACAGCCAUAUACUGACACAGACAGACGACUCGCUGAGGAUCCGACA |
| m3219-82 | 347 | GGAGGAGCUACGAUGCGGCAGGGGCGGGAUCUAAUGCGUAGACAGCCAUAUACUGACACAGACAGACGACUCGCUGAGGAUCCGACA |
| m3229-83 | 348 | GGAGGAGCUACGAUGCGGCCUAGUACAAAAGCCUGAUCUCUGUGAGCAGACACUAGAACAGACAGACGACUCGCUGAGGAUCCGACA |
| m3248-84 | 349 | GGAGGAGCUACGAUGCGGUGUACACUGAUUGCCUUUGUGUUAUGAGCGACAGAUCUGCCAGACAGACGACUCGCUGAGGAUCCGACA |
| m3250-85 | 350 | GGAGGAGCUACGAUGCGGCAUACACACUUGACUUUAGGGAACGAACCUCUAGCCGUGGCCAGACAGACGACUCGCUGAGGAUCCGACA |
| m3265-86 | 351 | GGAGGAGCUACGAUGCGGACGGAGGAUAGUUGCUAAUCGAGCCCUGCUGACGCUUCAGACAGACGACUCGCUGAGGAUCCGACA |
| m3428-87 | 352 | GGAGGAGCUACGAUGCGGCCGUCUCGCUCUCAUCCCAUGCACGAAACCUCUCUCAGUGCACAGACGACUCGCUGAGGAUCCGACA |
| m3435-88 | 353 | GGAGGAGCUACGAUGCGGUAAUUCUCAGGGGGUGCGGAACGGGAUAUGGAUUGUUCGCCAGUCAGACGACUCGCUGAGGAUCCGACA |
| m3435-89 | 354 | GGAGGAGCUACGAUGCGGUAAUUCUCAGGAGGUGCGGAACGGGACAUGGAUUGUUCGCCAGUCAGACGACUCGCUGAGGAUCCGACA |
| m3435-90 | 355 | GGAGGAGCUACGAUGCGGUAAUUCUCAGGAGGUGCGGAACGAGAUAUGGAUUGUUCGCCAGUCAGACGACUCGCUGAGGAUCCGACA |
| m3435-91 | 356 | GGAGGAGCUACGAUGCGGUAAUUCUCAGGAGGUGCGGAACGGGAUAUGAAUUGUUCGCCAGUCAGACGACUCGCUGAGGAUCCGACA |
| m3435-92 | 357 | GGAGGAGCUACGAUGCGGUAAUUCUCAGGAAGUGCGGAACGGGAUAUGGAUUGUUCGCCAGUCAGACGACUCGCUGAGGAUCCGACA |
| m3500-93 | 358 | GGAGGAGCUACGAUGCGGCCCAUCACUCCCGCGUAUGGCGAACGCAUCGUUAUUUAGCCGUCAGACGACUCGCUGAGGAUCCGACA |
| m3523-94 | 359 | GGAGGAGCUACGAUGCGGUCAUGGAUUCAUUACAGGAGGUGCGGUGCUAUAUGCACGCCAGACAGACGACUCGCUGAGGAUCCGACA |
| m3546-95 | 360 | GGAGGAGCUACGAUGCGGCCAGCCACACUUUGACCGAAUUGGCAAGCGCGGGCAAAUCGAACAGACGACUCGCUGAGGAUCCGACA |
| m3548-96 | 361 | GGAGGAGCUACGAUGCGGCCUAGUACAAAAGCCUGAUCUUUGGGAACCGACCCUAGGACAGACAGACGACUCGCUGAGGAUCCGACA |
| m3550-97 | 362 | GGAGGAGCUACGAUGCGGCUUACAGCUCACCAUUUAUGGGAGGCCCGGUGUUGUGUUCCAGACAGACGACUCGCUGAGGAUCCGACA |
| m3565-98 | 363 | GGAGGAGCUACGAUGCGGAUUAUUGUUUGACGUAUUCCAAGUGAGAUUACGCACGCACCAGACAGACGACUCGCUGAGGAUCCGACA |
| m3568-99 | 364 | GGAGGAGCUACGAUGCGGAACAGCUUAAUCGCCAGUCGAUACGCGCCAUACAUCAUCACAGACAGACGACUCGCUGAGGAUCCGACA |
| m3745-100 | 365 | GGAGGAGCUACGAUGCGGUAAUUCUCAGGAGAUGCGGAACGGGAUAUGGAUUGUUCGCCAGUCAGACGACUCGCUGAGGAUCCGACA |
| m3745-101 | 366 | GGAGGAGCUACGAUGCGGUAAUUCUCAGGAGGUGCGAAACGGGAUAUGGAUUGUUCGCCAGUCAGACGACUCGCUGAGGAUCCGACA |
| m3748-102 | 367 | GGAGGAGCUACGAUGCGGACGAUUUCGUCAUCCUCCAUACCAUCGCCUUACCGUUCAGCGUCAGACGACUCGCUGAGGAUCCGACA |
| m3773-103 | 368 | GGAGGAGCUACGAUGCGGCAACAAACUAAUCAGACACGAGACAGAGAGAUAGAUCUGCCAGACAGACGACUCGCUGAGGAUCCGACA |
| m3788-104 | 369 | GGAGGAGCUACGAUGCGGUUAUGCGUUUAAGUCAUUGACGCGUUACACUGGAGGGGCCAGACGACUCAGACGACUCGCUGAGGAUCCGACA |

TABLE 4-continued

Putative human islet specific aptamers isolated via
toggle-cluster SELEX (from FIG. 2)

| aptamer name | SEQ ID NO: | sequence |
|---|---|---|
| m3823-105 | 370 | GGAGGAGCUACGAUGCGGACGGAGGAUAGUUGCUAAUCGAGCCCU GCGGACGCUUCAGACAGACGACUCGCUGAGGAUCCGACA |
| m3831-106 | 371 | GGAGGAGCUACGAUGCGGCUUACAGCUCACCAUUUUUGGGAGGCC CGGUGUUGUGUUCCAGACAGACGACUCGCUGAGGAUCCGACA |
| m3845-107 | 372 | GGAGGAGCUACGAUGCGGACGGAAGGAUAGUUGCUAAUCGAGCCCU GCCGACGCUUCAGACAGACGACUCGCUGAGGAUCCGACA |
| m3997-108 | 373 | GGAGGAGCUACGAUGCGGUAAUUCUCAGGAGGUGCGGAACGGGAU AUAGAUUGUUCGCCAGUCAGACGACUCGCUGAGGAUCCGACA |
| m3997-109 | 374 | GGAGGAGCUACGAUGCGGUAAUUCUCAGAAGGUGCGGAACGGGAUA UGGAUUGUUCGCCAGUCAGACGACUCGCUGAGGAUCCGACA |
| m3997-110 | 375 | GGAGGAGCUACGAUGCGGUAAUUCUCAGGAGGUGCGGAACGGGAU AUGGAUUGUUCGCCCGUCAGACGACUCGCUGAGGAUCCGACA |
| m3997-111 | 376 | GGAGGAGCUACGAUGCGGUAAUUCUCAAGAGGUGCGGAACGGGAUA UGGAUUGUUCGCCAGUCAGACGACUCGCUGAGGAUCCGACA |
| m4097-112 | 377 | GGAGGAGCUACGAUGCGGCAAAAACUGAUAAACACAGGUCCGGCAU UUGAGCGUACACCCAGACAGACGACUCGCUGAGGAUCCGACA |
| m4110-113 | 378 | GGAGGAGCUACGAUGCGGUCGGAGGAUAGUUGCUAAUCGAGCCCU GCCGACGCUUCAGACAGACGACUCGCUGAGGAUCCGACA |
| m4275-114 | 379 | GGAGGAGCUACGAUGCGGUUAUGCGUUUAAGUCAUUGACGCGUUAC ACUGGAGGGGCCAGACAGACGACUCGCUGAGGAUCCGACA |
| m4347-115 | 380 | GGAGGAGCUACGAUGCGGCAAAAACUGAUAAACACAGGUCCGGCA UUUGAGCGUACACCCAGACAGACGACUCGCUGAGGAUCCGACA |
| m4365-116 | 381 | GGAGGAGCUACGAUGCGGACGGAGGAUAGUUGCUAAUCGAGCCCU GCCGACGCUUCAGACAGACGACUCGCUGAGGAUCCGACA |

Next, the specificity for human islets of the identified monoclonal aptamers were tested with the two high throughput cluster SELEX strategies described in FIG. 1 and FIG. 2. Briefly, monoclonal aptamers corresponding to the sequences identified by the bio-informatic analysis were generated by PCR and T7 RNA polymerase using overlapping oligonucleotides as template. The resulting monoclonal aptamers were labelled with Cyanin-3 and used as fluorescent probes on sections of human pancreas from cadaveric donor. Clone number is reported with the prefix "m" indicating the identification of aptamer from the HT-Toggle cluster SELEX. Data show that while some aptamers (m166-279, m5-3229, 107-901, m7-2537, m9-3076, 1-717, 173-2273, m12-3772) show a good specificity for the islets, others label also the acinar tissue (12-2617, 109-2031, m1-2623, m24-3219), and others did not show any staining (208-2529, 155-1113, 64-2437).

Figure 4:
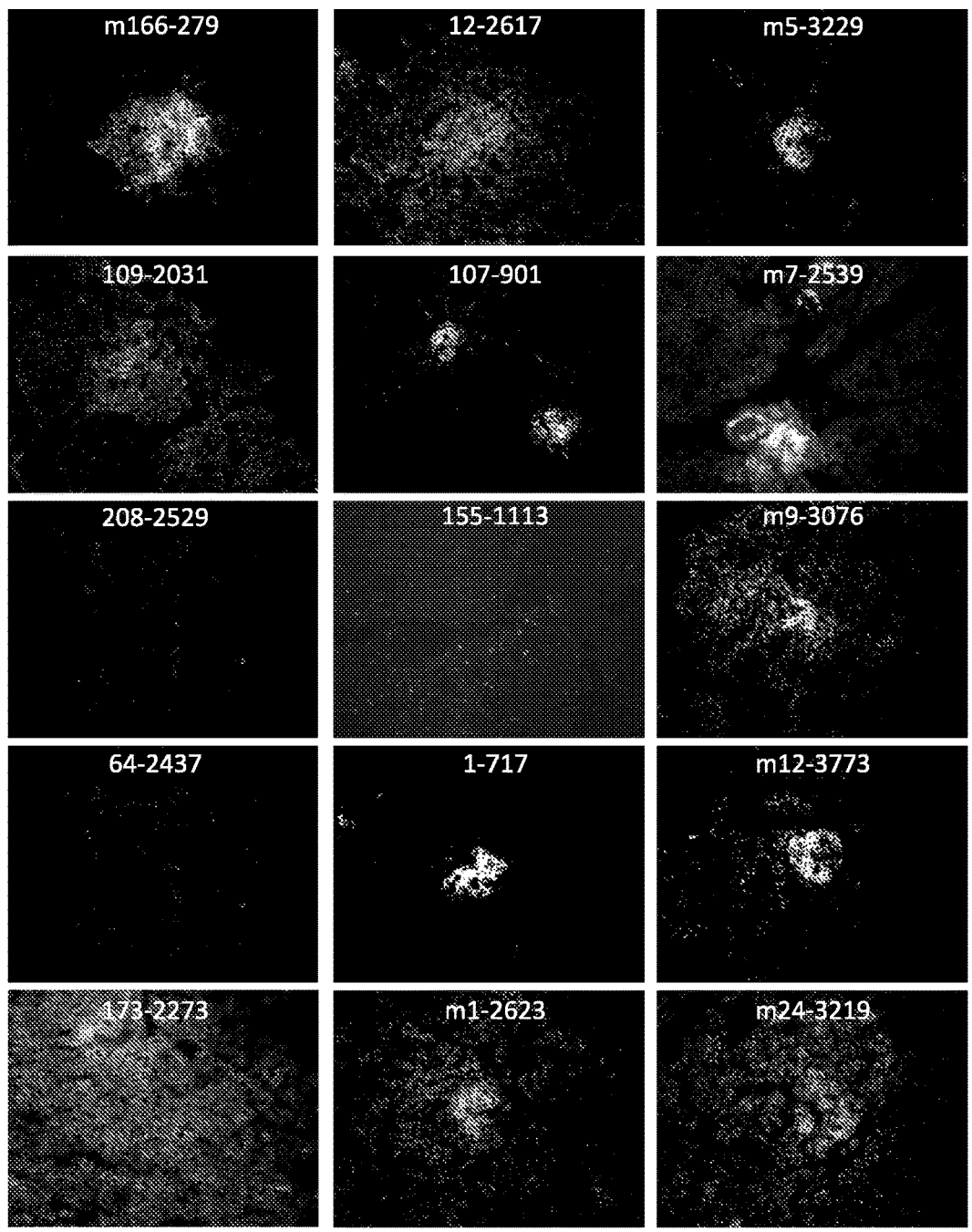
FIG. 4 shows images resulting from HT-Toggle-cluster SELEX identifying monoclonal aptamers that recognize human islets but not human acinar tissue.
Figure 5B:
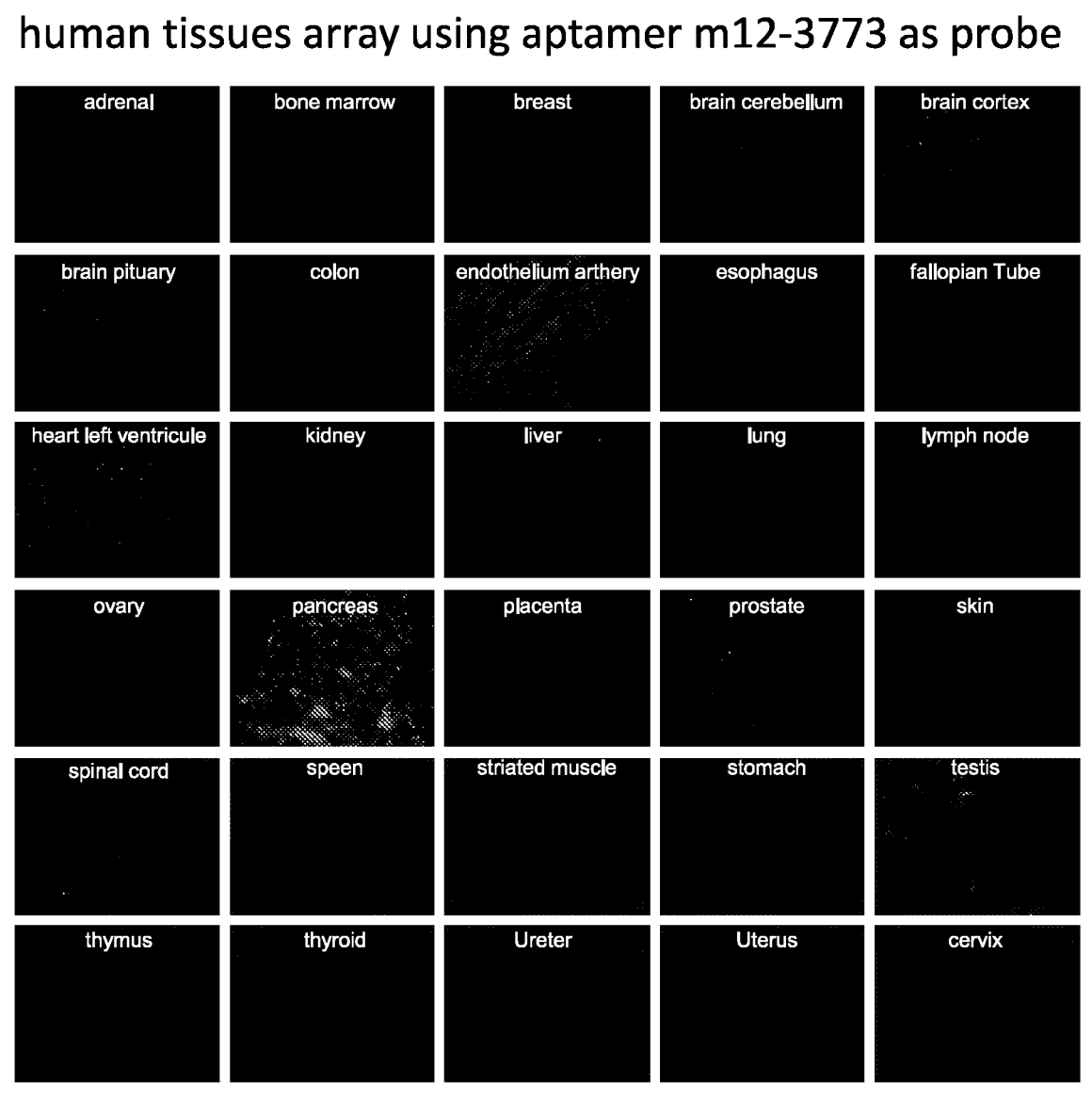

In order to evaluate further the specificity of the chosen monoclonal aptamers, the best performers of FIG. 4 (166-279, 173-2273, 107-901, 1-717, m1-2623, m5-3239, and m12-3773) were used to stained FDA approved tissues microarrays. Each of these arrays contains sections from 30 human tissues (with each tissue replicated from 3 different donors) and are usually used for antibodies screening but have not yet been used for aptamer evaluation. Briefly, these tissues microarrays were stained with the chosen cy3 labelled RNA aptamers of irrelevant aptamers as control. Each tissue was then analyzed by immunofluorescence microscopy. While most of the aptamers show binding not only as expected in the pancreatic islet but also in other tissues (FIG. 5C), aptamer 1-717 (FIG. 5A) and aptamer m12-3773 (FIG. 5B) show an extraordinary specificity for the pancreatic islets and negligible binding to the other tissues evaluated (adrenal, bone marrow, breast, brain, colon, endothelial, esophagus, fallopian tube, heart, kidney, liver, lung, lymph node, Ovary, placenta, prostate, skin, spinal cord, spleen, muscle, stomach, testis, thymus, thyroid, ureter, uterus, and testis).

To evaluate if aptamer 1-717 and m12-3772 can recognize not only human islets but also the mouse counterpart, staining with these two Cy-3 labelled monoclonal aptamers were performed on tissues microarrays each containing 11 tissues from healthy mice. These experiments show that both aptamer 1-717 and aptamer m12-3773 can also recognize mouse islets. See FIG. 6. However, in contrast to what observed on human tissues, both aptamers can recognize at different level not only the pancreatic tissue but also the spleen, the stomach, and the jejunum. These data suggest that differences in the distribution of the cognate targets may exist between the two species.

Figure 7A:
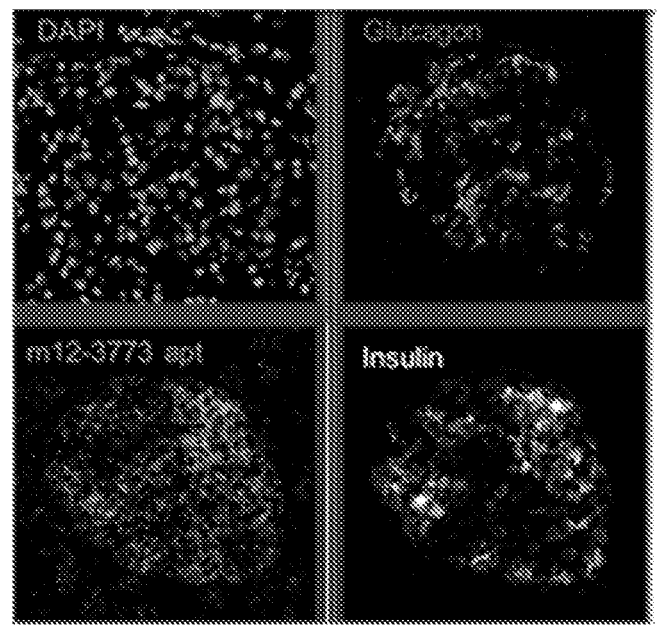
FIG. 7 shows that aptamers 1-717 and M12-3773 recognize preferentially human beta cells.
Figure 7B:
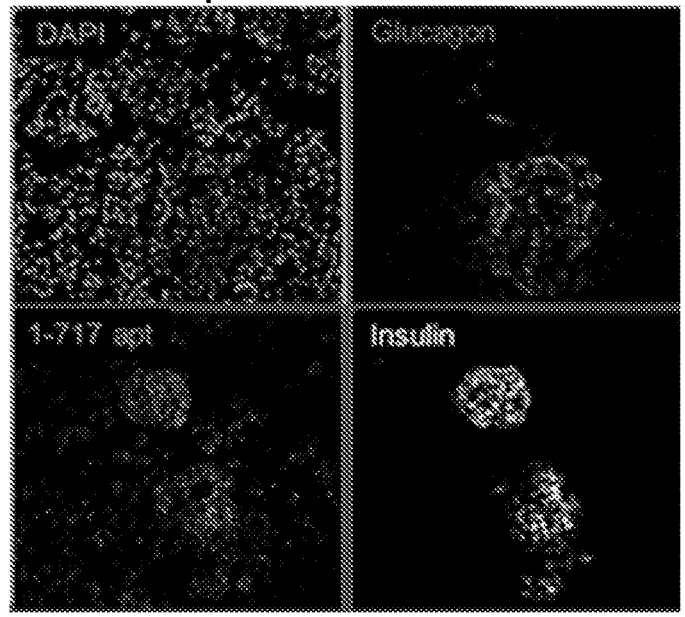
Figure 7C:
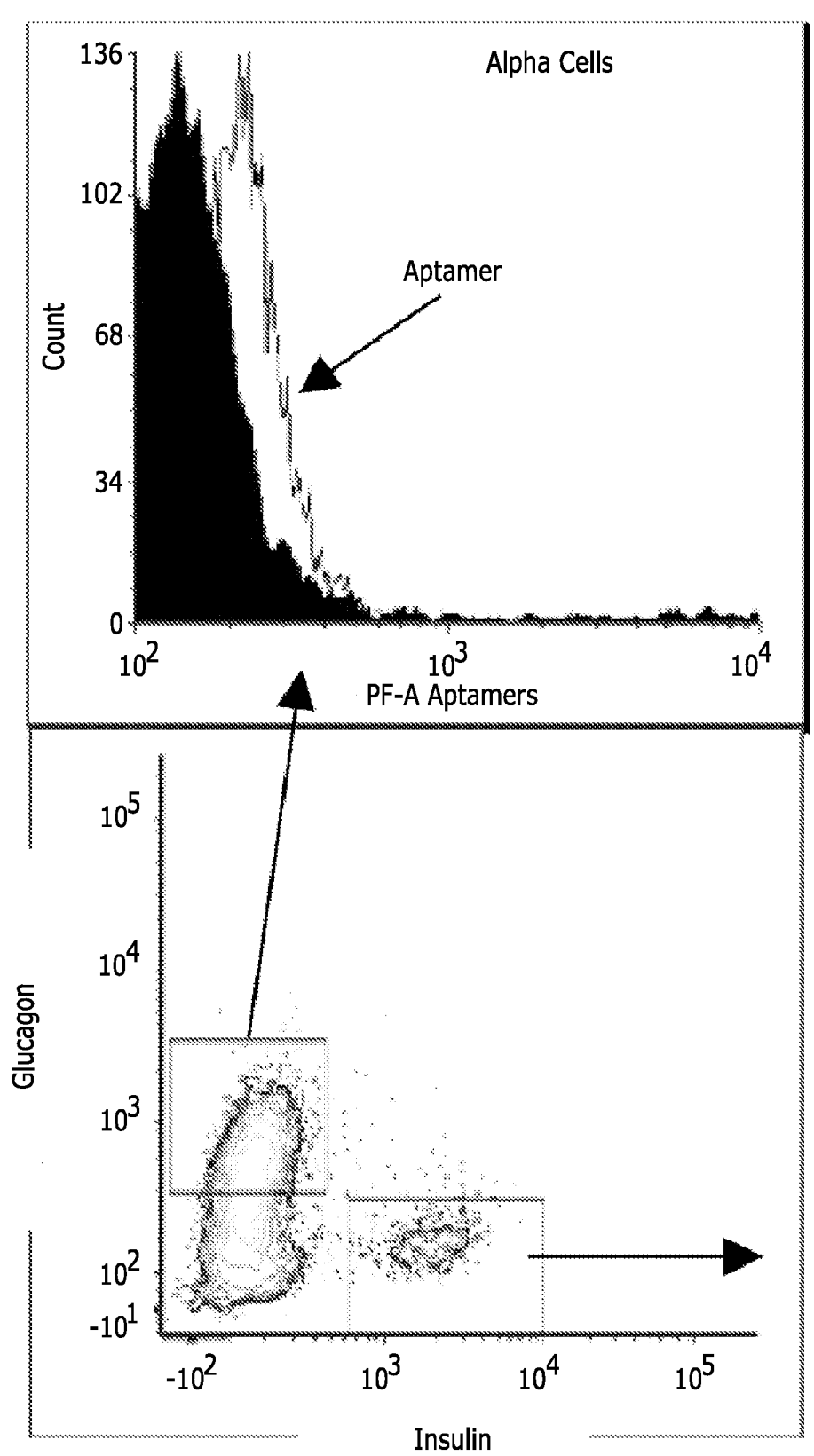
Figure 7C:
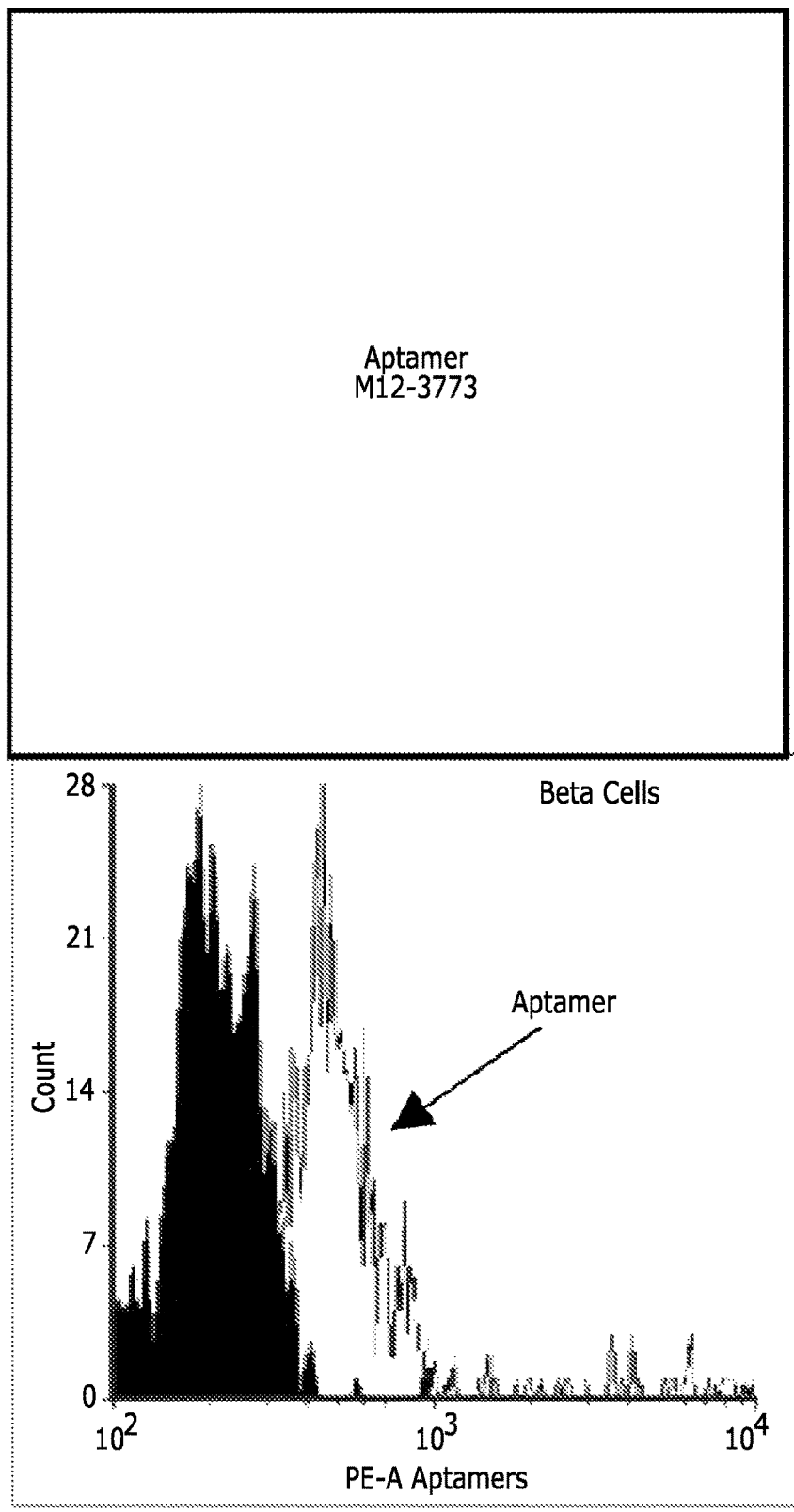
Figure 7D:
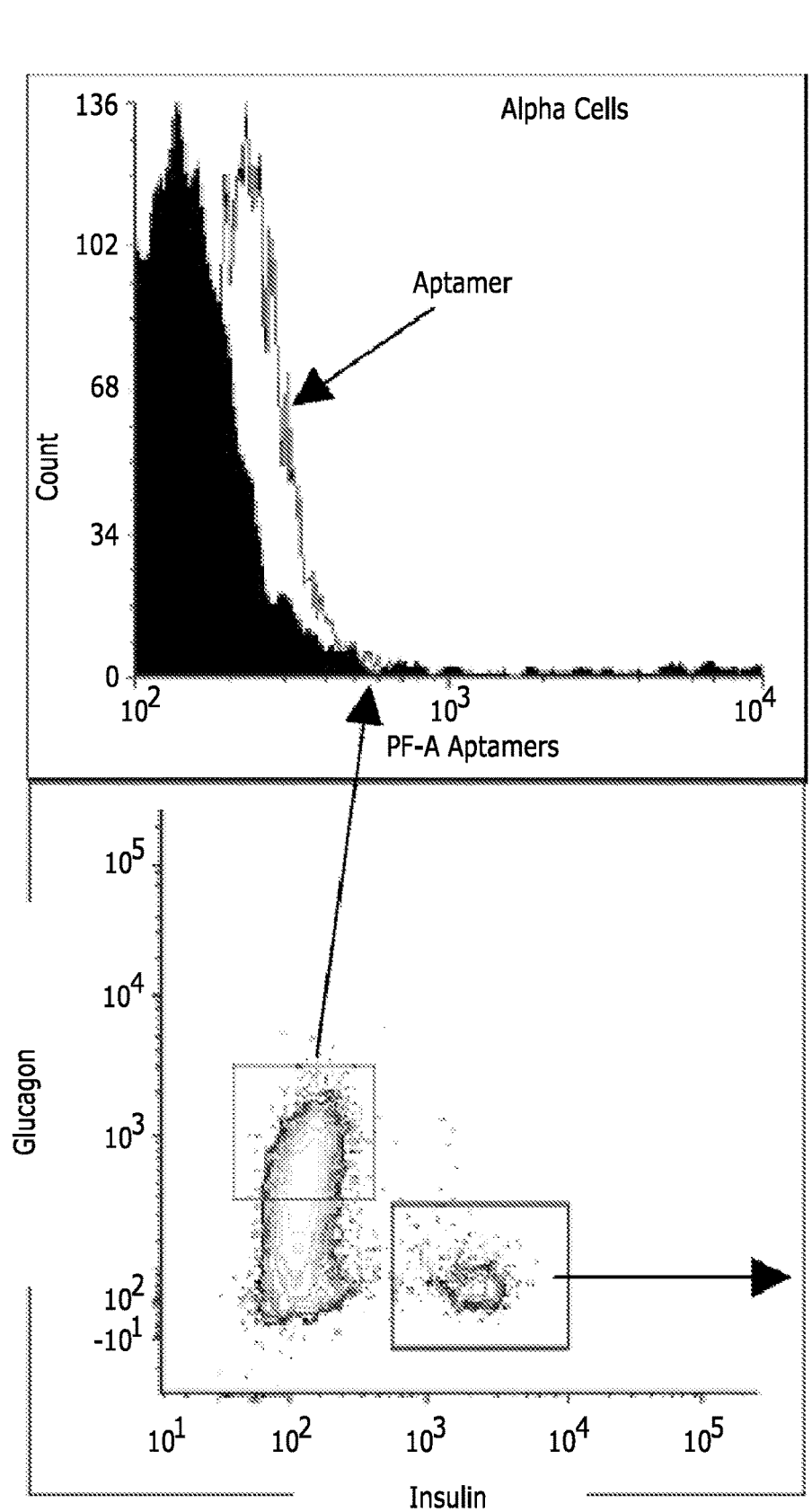
Figure 7D:
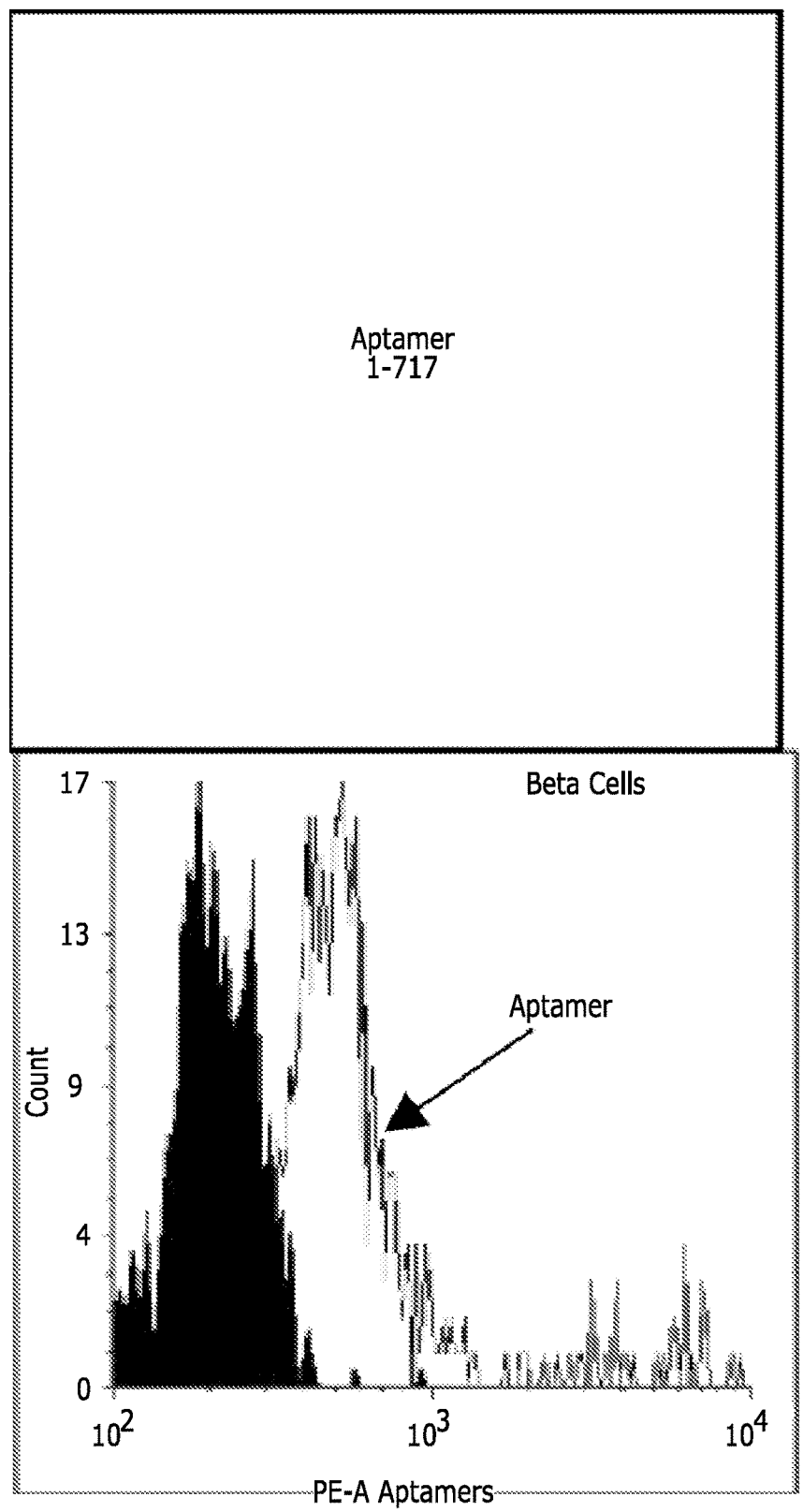

To evaluate better the specificity of the aptamers within the islets, two different techniques were employed: confocal microscopy (FIG. 7A and FIG. 7B) and flow cytometry (FIG. 7C and FIG. 7D). For confocal microscopy, sections of human pancreas were stained with cy-3 labelled aptamer M12-3773 (FIG. 7A) or cy3-labeled aptamer 1-717 (FIG. 7B). Sections were counterstained with antibodies against insulin and glucagon, and DAPI and evaluated by confocal microscopy. Data show binding of both aptamers to both alpha and beta cells but with an higher signal on beta cells.

For flow cytometry, single cell suspension of human islets were stained with Cy3 labelled aptamer M12-3773 (FIG. 7C) or cy3-labeled aptamer 1-717 (FIG. 7D), counterstained with vital dye and antibodies specific for insulin and glucagon, and analyzed. Aptamer signal (open histograms) was quantified on the alpha (top histograms) or beta cells (right histograms) after gating respectively on glucagon positive or insulin positive cells (contour plot). An irrelevant aptamer (filled histograms) was used as negative control.

Figure 8A:
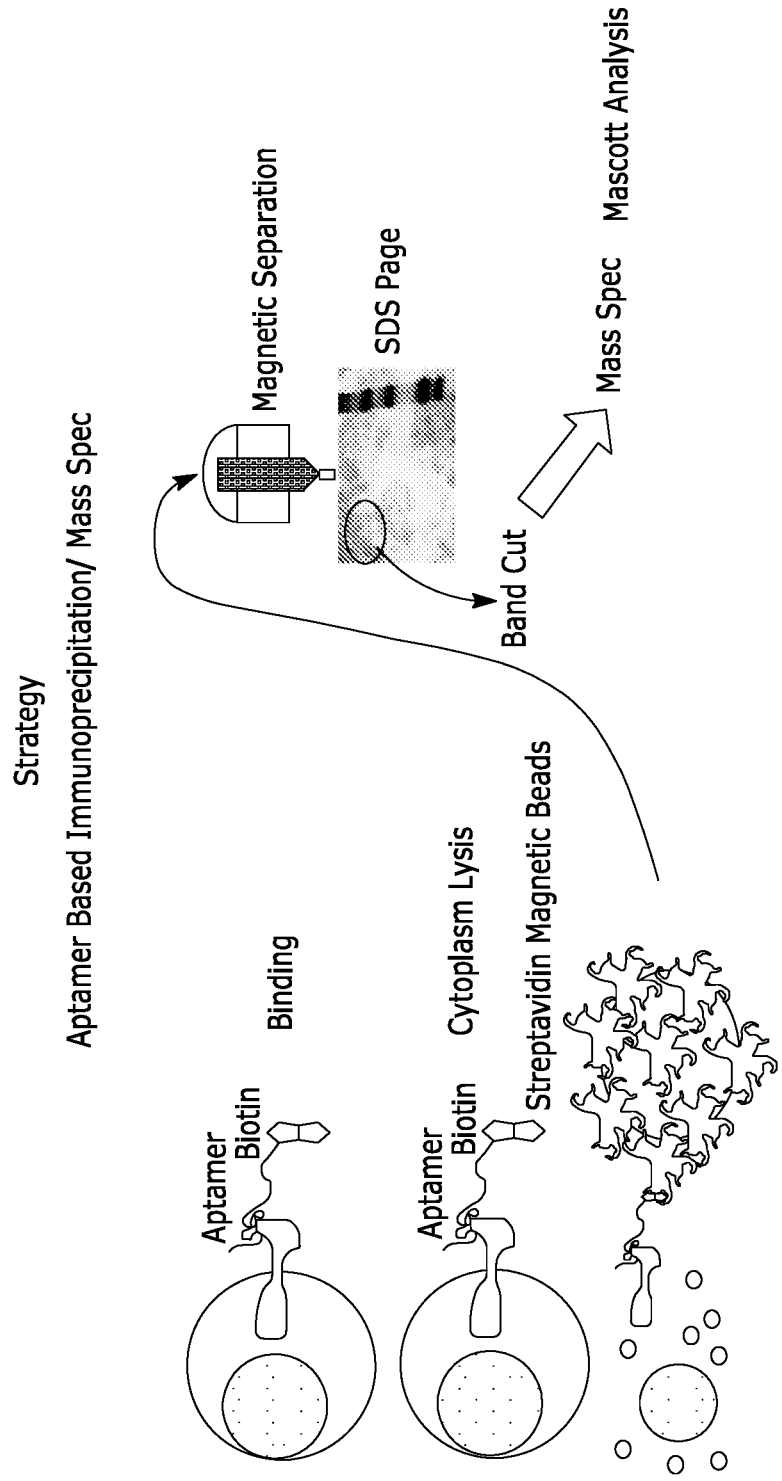
FIG. 8 shows that clusterin is a possible target for aptamer m12-3773.

Clusterin is a possible target for aptamer m12-3773. 3'biotin-aptamer m12-3773 was synthetized with a oligo synthesizer and used to label single cell suspension from human islets. Cells were washed and their cytoplasm lysed with tween20/BSA solution. Aptamers bound to their ligand recovered with magnetic beads and magnetic separation. Capture ligands were released by the aptamer-beads complex at 95° C. in SDS and run in SDS page. Bands were cut and subjected to mass spectrometry and mascot-based analysis (FIG. 8A). Clusterin (UniProtKB-P10909) (FIG. 9B) was one of the protein with the higher score (236), had an elevated sequence covered from peptides identified by mass spectrometry, had a molecular weight compatible to the one of the band cut from the SDS page, and more importantly, was the only one of the tested one whose silencing reduced the capacity of aptamer m12-7337, but not of aptamer 1-717, to bind to beta cells (FIG. 8C).

Figure 9A:
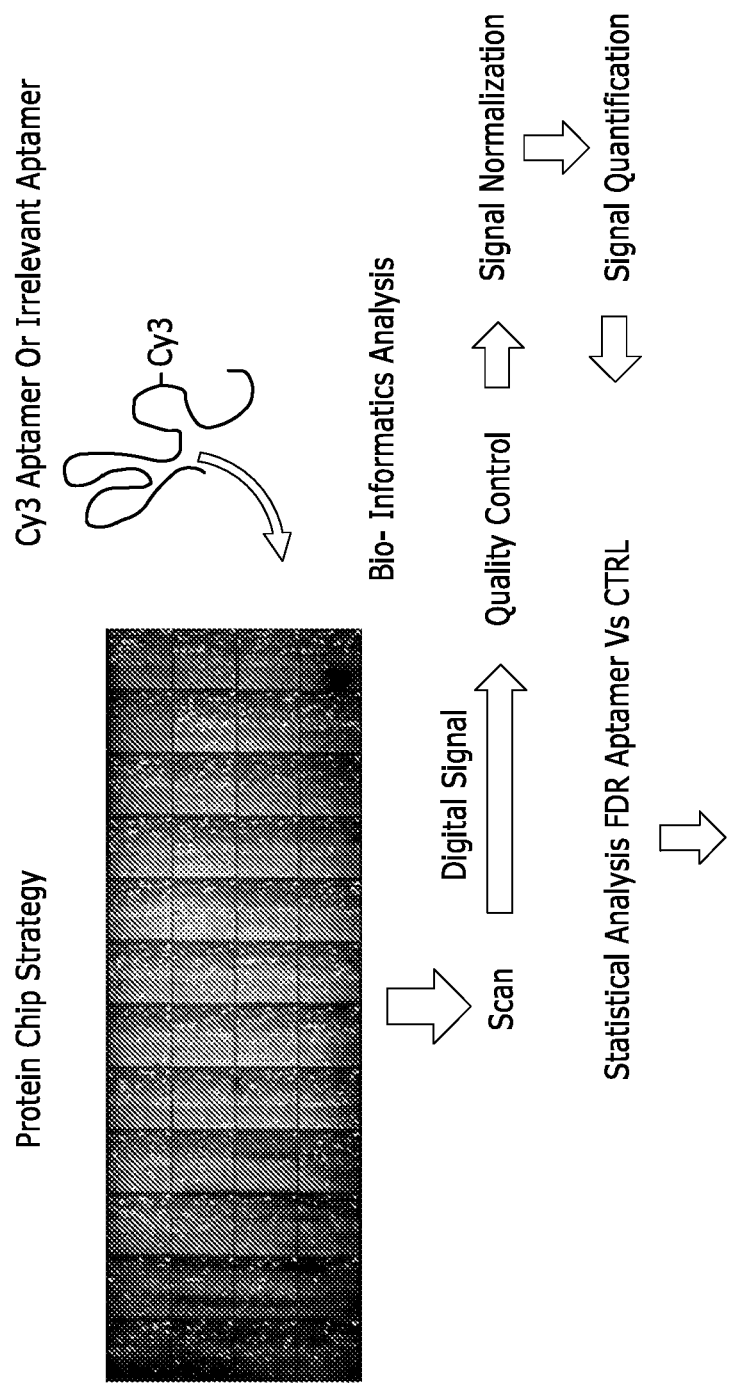
FIG. 9 shows that TMED6 is the putative target for aptamer 1-717.
Figure 9C:
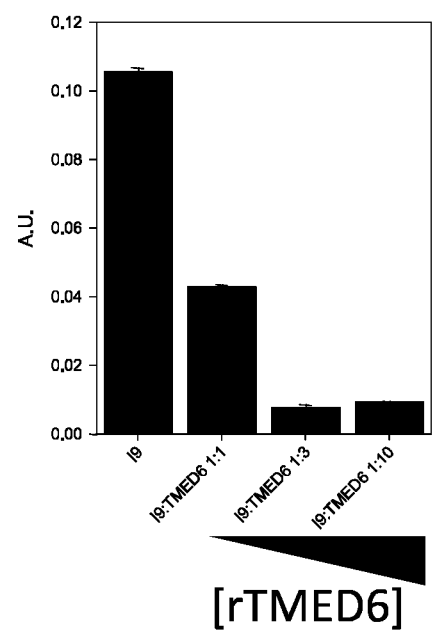

FIG. 9 shows that TMED6 is the putative target for aptamer 1-717. FIG. 9A shows the experimental strategy to detect the target for aptamer 1-717. To identify the target of aptamer 1-717, protein arrays (HuProt™v2.0, Arrayit) were used. These protein arrays contains more than 19,000 human recombinant proteins allowing, by informatics analysis, the identification of the cognate protein of antibodies, peptides, or protein. This technology has been adapted for the identification of aptamer's ligands. Briefly, pre-blocked arrays were hybridized with 1 µg of cy3 labeled 1-717 or m12-3773 in blocking buffer for 30' at RT. Arrays were washed, read in triplicate on a Genepix microarray reader and analyzed by an ad hoc generated software. This software 1) acquires the data from the gpr file, 2) adds a description column with (GeneID, Control, blank, ND), 2) use a optimized "plotArray" function modified in several points (the script was implemented for a specific protein array, plus some problem in UTF file format), 3) performs a quality control that includes a microarray image rebuilding the generation of MA plots, 4) normalized the data and substracts the background; and 5) analyze the differential expression between arrays via graphs of p-value distribution, volcano plot, and analysis of significant modulation by t-test. This analysis proposed TMED6 (NM144676.1, protein id Q8WW62) as the most likely ligand of aptamer 1-717. See FIG. 9B. Competitive assays (FIG. 9C) confirm the specificity of this target. As shown in FIG. 9C, competitive assays confirm the specificity of aptamer 1-717 for TMED6. Briefly, serial sections of human pancreas were stained with Cy-3 labelled aptamer 1-717 in the presence of different concentration of recombinant TMED6 protein (i.e., molar ratio aptamer/recombinant protein range=1/1-1/10). Images were acquired by a fluorescence microscope and aptamer binding quantified by cellprofiler. Data show that addition of recombinant TMED6 inhibit aptamer 1-717 binding in a dose dependent manner strongly suggesting that TMED6 is the target of this aptamer.

Example 2—Identified Aptamers were Islet Specific In Vivo

To evaluate whether aptamer 1-717 and m12-3773 can recognize human islets in vivo, we employed immunodeficient NSG mice engrafted with human islets in the epydidimal fatpad. Additionally, we use a new formulation of aptamer 1-717 and aptamer m12-3773 in which each monoclonal aptamer is biotinylated and complexed with streptavidin to form a tetrameric nanoparticle (hereafter called tetraptamer). This formulation has a superior pharmacokinetic and better affinity than the corresponding monomeric aptamer.

Figure 10A:
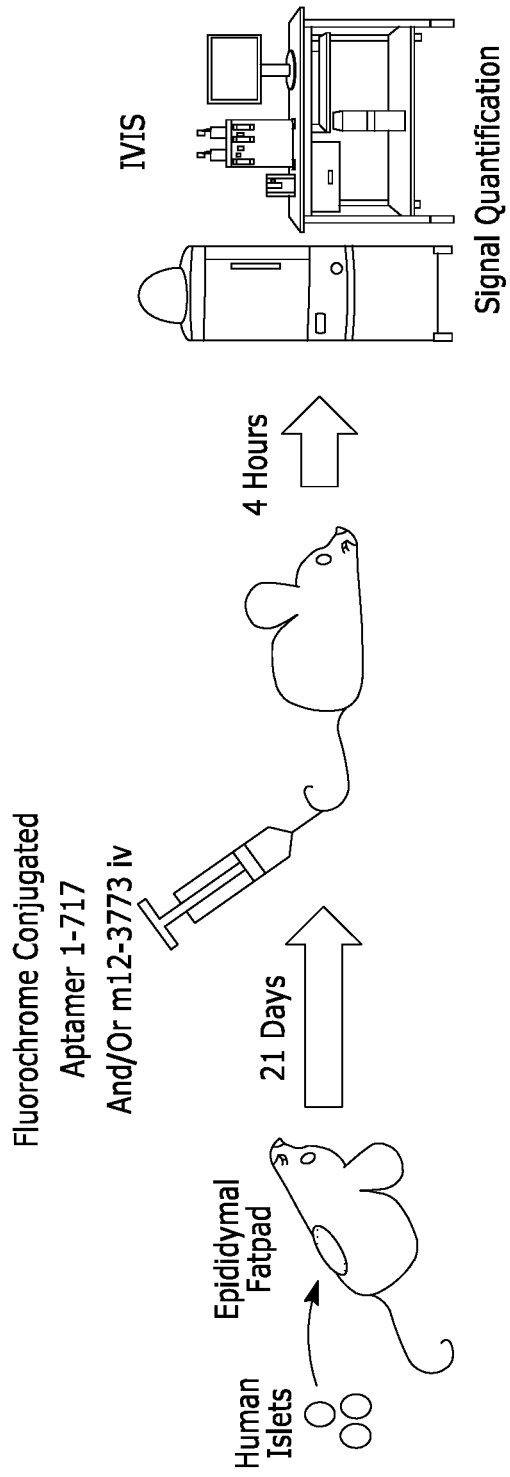
FIG. 10 shows that a mixture of aptamer 1-717 and m12-3773 recognize human islets in vivo better than the individual clones.
Figure 10B:
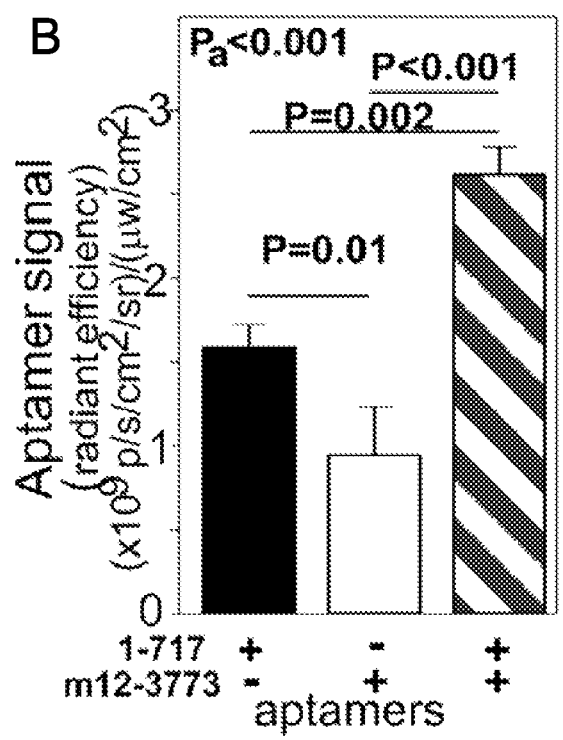

Biotin/streptavidin Alexafluor (AF750)-labeled aptamers (amptamer 1-717 or aptamer m12-3773, or an equimolar mixture of the two aptamers) were injected intravenously in immunodeficient NSG mice (engrafted with human islets in the epididymal fat pad (EFP)) to evaluate whether m12-3773 and 1-717 can recognize human islets in vivo. A cumulative-synergistic signal was observed in the EFP region when the mixture of both aptamers was used possibly because different islet epitopes were targeted by each aptamer (FIG. 10A). 4 hour later fluorescence signal in epididymal fat pad region was measure by "In vivo imaging system (IVIS)". The data in FIG. 10B shows that both aptamer 1-717 and aptamer m12-3773 can recognize the islets in vivo. Additionally this experiment reveals that the use of an equimolar mixture of the two aptamers significantly increase the signal to background ratio.

Figure 11A:
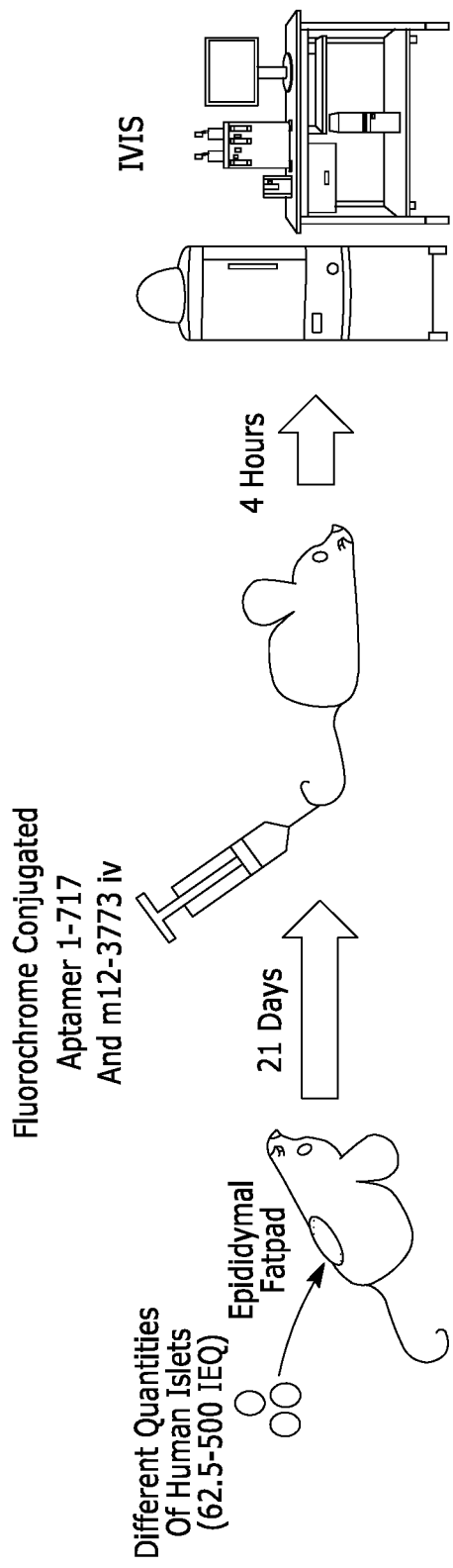
FIG. 11A is a schematic of the experiment performed in Example 2.
Figures 11B, 11C:
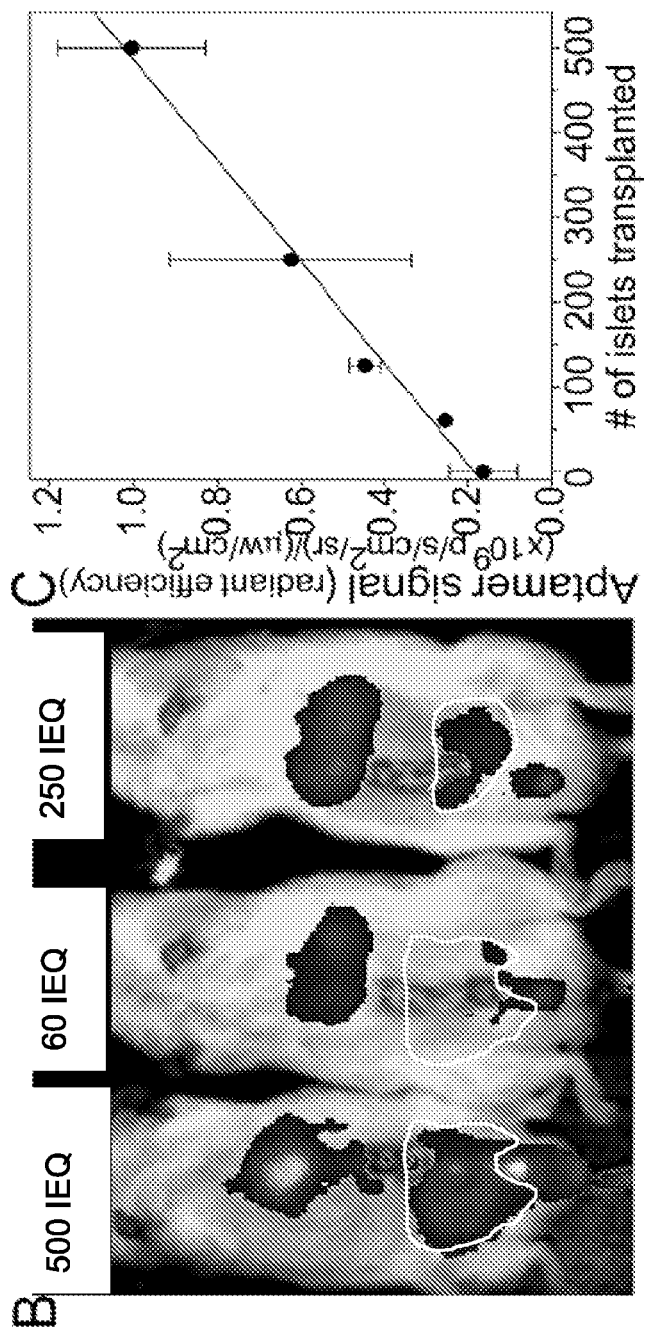
FIGS. 11B and 11C show that fluorescence signal in the EFP region was proportional to the number of engrafted islets indicating that these aptamers can be used to measure β cell mass in vivo

To determine if aptamers m12-3773 and 1-717 can be used to measure β mass in vivo, immune deficient NSG mice were transplanted with different quantities (range 62.5-500 IEQ) of human islets in the epididymal fatpad. 21 days later, mice were injected iv with Alexafluor 750 tetraptamer generated by the complexation of an equimolar mixture of aptamer 1-717 and m12-3773 to streptavidin. 4 hours later signal was quantified by IVIS. FIG. 11A. Aptamers m12-3773 and 1-717 recognized both the mouse endogenous islets and the human islets transplanted in the EFP (FIG. 11B). Importantly, fluorescence signal in the EFP region was proportional to the number of engrafted islets indicating that these aptamers can be used to measure β cell mass in vivo (FIGS. 11B and 11C). The signal from the islets persisted for 10 days after injection (not shown). As shown in FIG. 11D, rejection of the allogeneic C57B16 islet graft can be measured over time as seen by the loss of signal on the left flank. Instead signal (right panel of FIG. 11D) of the syngeneic graft is maintained over time indicating graft survival.

In summary, the selected aptamers m12-3773 and 1-717 bind mouse and human β cells with good specificity in vitro and in vivo and thus may be useful in targeting therapeutics to human β in vivo.

Example 3—Aptamera Chimera can Deliver Therapeutic RNA to Islets

Figure 12:
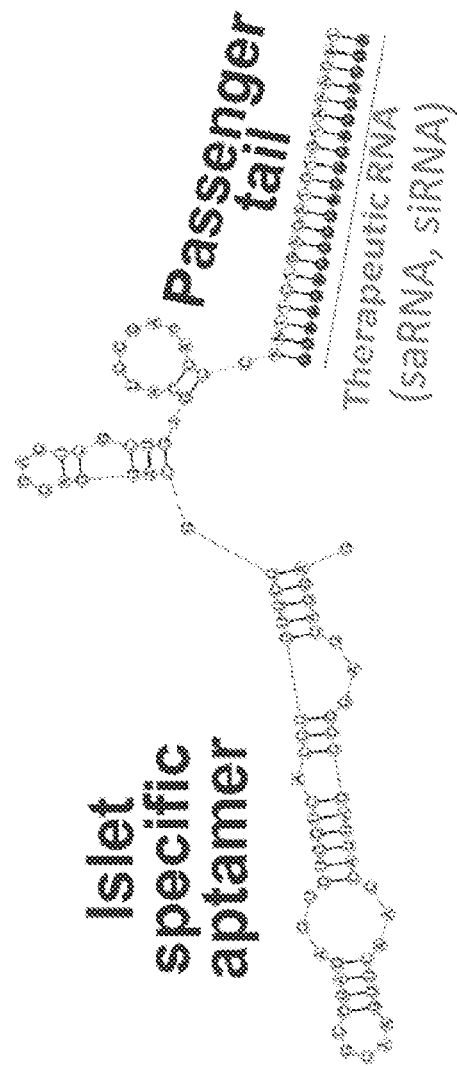
FIG. 12 is a schematic diagram aptamer chimera for the delivery of therapeutic RNA via islets specific aptamers.

As shown in FIG. 12, islet-specific RNA aptamers 1-717 and m12-3773 can be easily conjugated to therapeutic RNA by prolonging their 3' end with a trinucleotide linker region (i.e. GGG) and the passenger strand (passenger tail) of the desired therapeutic RNA. The therapeutic RNA guide strand is then simply annealed to the modified aptamer by admixing equimolar quantities of the two RNAs at 70° C. and allowing the mixture to slowly cool down at room temperature.

Figure 13A:
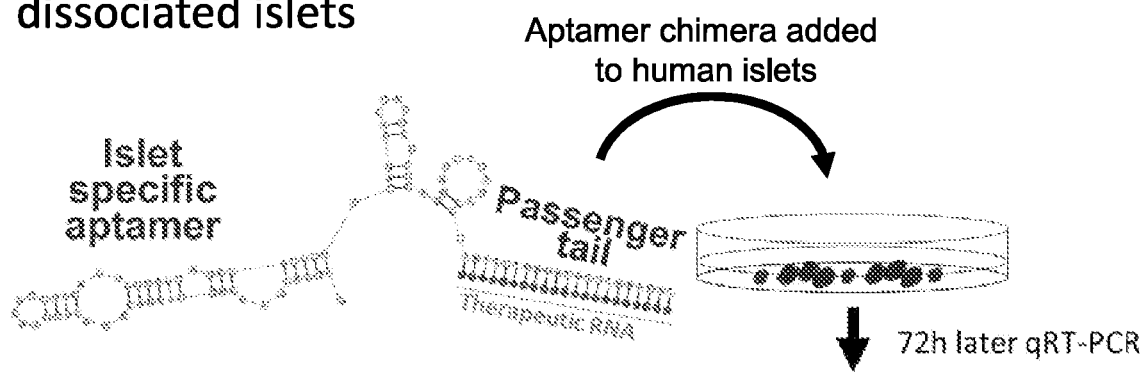
FIG. 13 shows that islets specific aptamer chimera allows for the delivery of therapeutic RNA via islets specific aptamers.
Figure 13B:
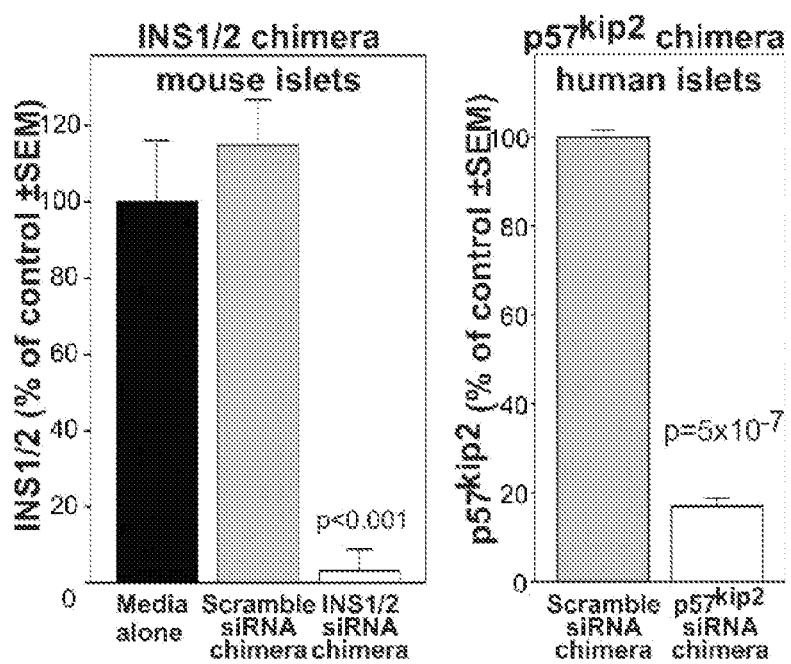
Figure 14A:
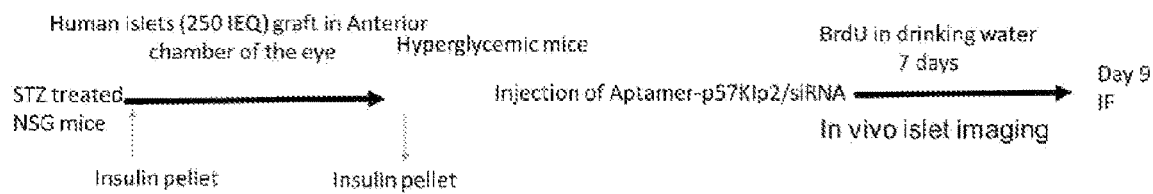
FIG. 14 shows that p57kip2-siRNA-islet specific aptamer chimera induce human beta cell proliferation in vivo.
Figure 14B:
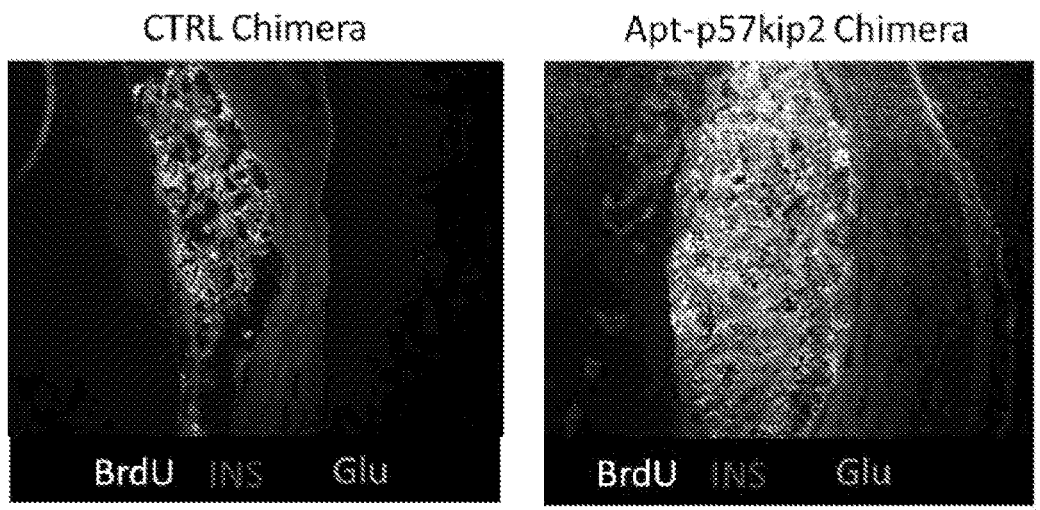
Figure 14C:
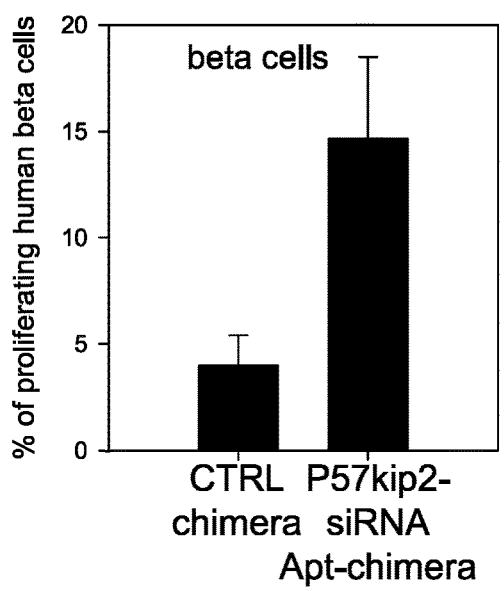
Figure 14C:
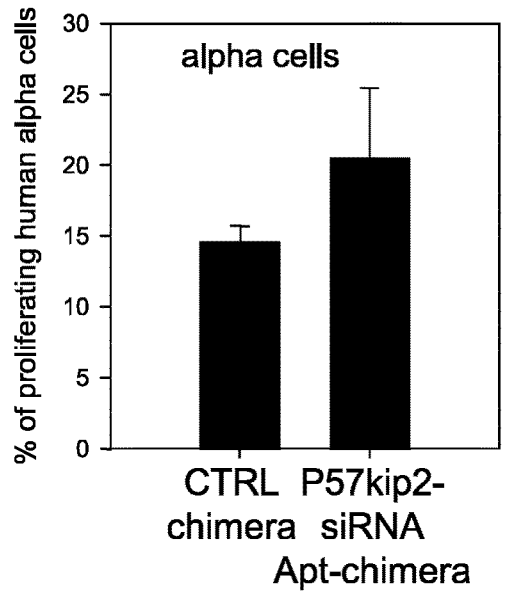

To evaluate if aptamers can be a non-viral alternative for transfecting β cells, we conducted proof of principle experiments aimed to knockdown via aptamer delivery insulin (INS) 1 and 2 in non-dissociated mouse islets. FIG. 13A is a schematic of the experimental procedure. Islets specific aptamer chimera were generated as detailed in FIG. 12 by conjugating aptamer 1-717 or aptamer m12-3773 with siRNA specific for mouse insulin 1/2 (INS1/2) or the inhibitor of cell proliferation human p57kip2 (uniprot P49918, alias CDN1c). The INS1/2-siRNA/aptamer chimera was added to non-dissociated mouse islets whereas the p57kip2-siRNA/aptamer chimera was added to human islets from a cadaveric donor. Scramble siRNA/aptamer chimera were used as negative controls. 72 hours later, expression of INS1/2 and p57kip2 was quantified by qRT-PCR on transfected mouse islets and transfected human islets respectively. As shown in FIG. 13B, the aptamer chimera significantly downregulate the expression of the target gene.

As shown in FIG. 14, p57kip2-siRNA-islet specific aptamer chimera induce human beta cell proliferation in vivo. FIG. 14A shows the experimental procedure: Streptozotocin-treated, immune deficient NSG mice were transplanted with a suboptimal quantity (250 IEQ) of human islets in the anterior chamber of the eye. Mice were maintained euglycemic by s.c. implantation of insulin pellet. 21 days later, when islets were vascularized, insulin pellet was removed to allow the development of hyperglycemia, mice were fed with BrdU for 7 days to evaluate cell proliferation, and treated with i) scramble-siRNA/aptamer chimera, or ii) p57kip2-siRNA/aptamer chimera. Nine days after treatment, mice were humanely euthanized, and beta and alpha cell proliferation was evaluated by immune fluorescence microscopy after labeling the graft sections with antibodies against insulin, glucagon, and BrDU (white). FIG. 14B provides immunofluorescence pictures of the graft from mice treated with control chimera or p57kip2-siRNA/aptamer chimera. Glucagon and insulin staining is depicted in dark gray as pseudocolor whereas BrdU staining as measure of cell proliferation is depicted in white as pseudocolor. FIG. 14C shows quantification of proliferating beta and alpha cells. Taken together these data indicate that p57kip2-siRNA/aptamer chimera can induce in vivo human beta cell proliferation in a hyperglycemic setting that mimic T1 and T2 diabetes.

P57kip2 silencing in $\beta$ cells has important therapeutic implications. Indeed, mutations of p57Kip2 are associated with focal hyperinsulinism of infancy (FHI), a clinical syndrome characterized by a dramatic non-neoplastic clonal expansion of $\beta$ cells (14), overproduction of insulin, and severe uncontrollable hypoglycemia (89,90). FHI's focal lesions are characterized by excessive $\beta$ cell proliferation that correlates with p57kip2 loss (91,92). Although the pro-proliferative activity of p57kip2 silencing is not desirable in FHI and in cancers, a temporally defined silencing might be useful to promote adult $\beta$ cell proliferation in T1D. Indeed, adenoviral-shRNA mediated silencing of p57kip2 in human islets obtained from deceased adult organ donors increased $\beta$ cell replication by more than 3-fold once the islets were transplanted into hyperglycemic, immune-deficient mice (14). The newly replicated cells retained properties of mature $\beta$ cells, such as expression of insulin, PDX1, and NKX6.114. Interestingly, no $\beta$ cell proliferation was observed in normoglycemic mice indicating that hyperglycemia may provide additional pro-proliferative signals (93). These findings opened the possibility for a new therapeutic intervention to restore an adequate $\beta$ cell mass in patients with T1D and/or to reduce the number of islets needed during transplantation. However, to date the translatability of these finding was hindered by safety concerns associated with use of viral vectors and neoplasm formation as a result of stable p57Kip2silencing. Indeed, p57Kip2 is frequently downregulated in human cancers (94) and has been proposed as a tumor suppressor gene since its ectopic expression is sufficient to halt neoplastic cell proliferation (94). However, a temporally controlled modulation of p57kip2 through aptamer delivery may be important in diabetes to increase $\beta$ cell proliferation in a temporally controlled manner. This might be sufficient to increase $\beta$ cell mass during timed administrations while avoiding the safety concerns with non-controllable, neoplastic-like proliferation of $\beta$ that may results with stable silencing.

Example 4—Upregulation of XIAP Via saRNA-Aptamer Chimera Inhibits Apoptosis in $\beta$Cells Apoptotic cell death is a hallmark in the loss of insulin-producing $\beta$ in all forms of diabetes (99-101). Leukocytes infiltration and activation as well as high glycemia within the islets leads to high local concentrations of apoptotic trigger including inflammatory cytokines, chemokines, and reactive oxygen species 99. Most of these apoptotic pathways converge onto caspase (CASP) 3 and 7 activation leading to genetic reprogramming, phosphatidylserine flip, and apoptotic bodies formation (102).

$\beta$ cell apoptosis can further feed the autoimmune process by stimulating self-antigen presentation and autoreactive T cell activation (103). Similarly, in islets transplantation setting, primary non-function, i.e. the partial but significant and sometimes total loss of the grafted islet mass, which occurs early after transplantation (104-106). $\beta$ cell apoptosis initiates during the isolation procedure and upon transplantation is exacerbated by hypoxia and hyperglycemia as well as pro-coagulatory and proinflammatory cascades (107). Primary-non-function accounts for more than 50% of the functional islet mass loss occurring during the first 48 hours after transplantation (106).

Thus, blocking even temporally apoptotic $\beta$ cell death is highly desirable not only to preserve $\beta$ cell mass in type 1 diabetes (T1D) and in islet transplantation but also to reduce auto-reactive T cell activation and further immune damage.

This protein is most potent member of the apoptosis-inhibitor family and prevents the activation of CASP 3, 7 and 9 (108); ii) Xiap overexpression using viral vector improved $\beta$ cell viability, prevented their cytokine- or hypoxia-induced apoptosis (109-111), iii) Xiap transduced human islets prolonged normoglycemia when are transplanted in diabetic NOD-SCID mice (11). However, since Xiap is upregulated in many cancers, its stable overexpression raise important safety concerns. Therefore, a controlled Xiap activation via saRNA delivered with islets specific aptamers can be useful alternative to reduce primary non-function, prevent $\beta$ cell loss and the self-feeding autoimmune process in T1D.

Small activating RNAs (saRNAs) are oligonucleotides that exert their action in specific promoter regions and upregulate mRNA and protein expression for up to 4 weeks (depending on cell replication, mRNA and protein turnover) (112-122). saRNA-mediated gene upregulation through mechanisms still not fully understood but is thought to involve epigenetic changes or down-modulation of inhibitory RNA (123-125). saRNAs provide safe, specific, and temporary gene activation without the insertion of DNA elements since their specificity is comparable to that of gRNA in CRISP/CAS9 system but no irreversible DNA modification are induced 126. While therapeutic saRNAs are being investigated for cancer treatment, to our knowledge no studies have been performed in T1D (127-130).

Figure 15A:
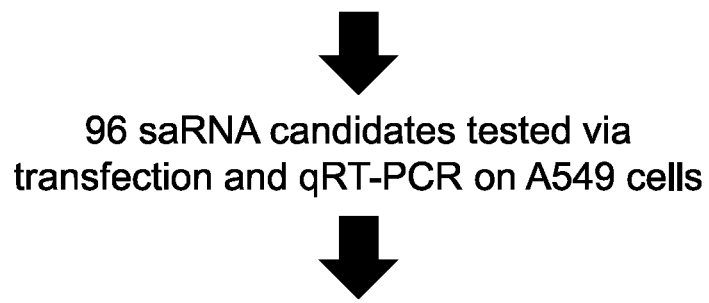
FIG. 15 shows the identification of small activating RNA (saRNA) specific for the human "X-Linked Inhibitor Of Apoptosis" (Xiap, Gene ID: 331).
Figure 15B:
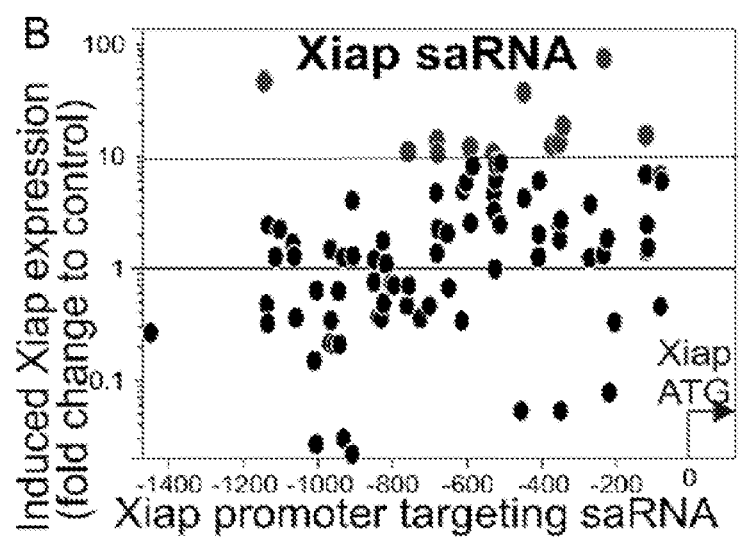

Therefore, we have identified saRNAs capable of specifically upregulating the anti-apoptotic gene XIAP. Briefly, we have first examined the human XIAP promoter using the previously described algorithms (112,131). This analysis that includes genome blast analysis to avoid non-specific sequences, returned more than 156 putative saRNA target regions. We synthetized the 96 putative saRNA with highest scores and tested them for their capacity to upregulate Xiap by transfecting the human epithelial cell line A549. This cell line was used because it is easily transfectable, has low basal expression of PDL1 and Xiap. qRT-PCR was performed 96 hours after transfection and results were normalized on the same cell line transfected with scrambled saRNA (FIG. 15). Twelve saRNAs (provided in Table 5) were found to upregulate Xiap expression more than 10 times (range 10.4-74.8) over scrambled saRNA.

TABLE 5 saRNA sequences to upregulate human Xiap

| Position | Fold change | Xiap saRNA sequence | SEQ ID NO: |
|---|---|---|---|
| -234 | 74.8083 | UAGCUGAAGUUCAUCUCUCuu | 382 |
| -1134 | 46.7026 | UUUCAGCCUUAAGGAUGGUuu | 383 |
| -449 | 37.1938 | UUUAUUCUCCCCUUGGGUGuu | 384 |
| -344 | 18.7146 | UACUCCCUCUGCCUAUGUGuu | 385 |
| -121 | 15.4365 | UUUACUGUUUUGGCUGGGCuu | 386 |
| -682 | 13.9281 | AAAAUGCUGGUCAUACCCUuu | 387 |
| -354 | 13.1961 | UUGUUCAAACUACUCCCUCuu | 388 |
| -374 | 12.5789 | UUUUCCUGCCUUCCGCUAAuu | 389 |
| -593 | 11.9908 | UUACAGGGUAAUGUGGUGAuu | 390 |
| -758 | 11.0947 | GAUGGGAGGUGAAGGGAAuu | 391 |
| -680 | 10.6792 | AAUGCUGGUCAUACCCUGGuu | 392 |
| -531 | 10.5239 | UACAAGAUAUGAUCCUCCCuu | 393 |

Figure 16A:
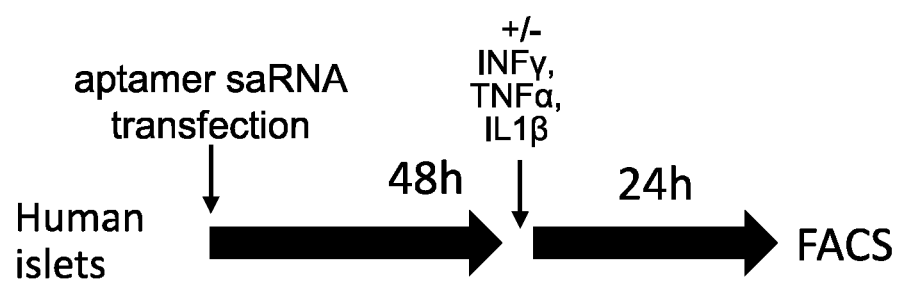
FIG. 16. Xiap-saRNA aptamer chimera protect human beta cells from cytokine induced apoptosis.
Figure 16B:
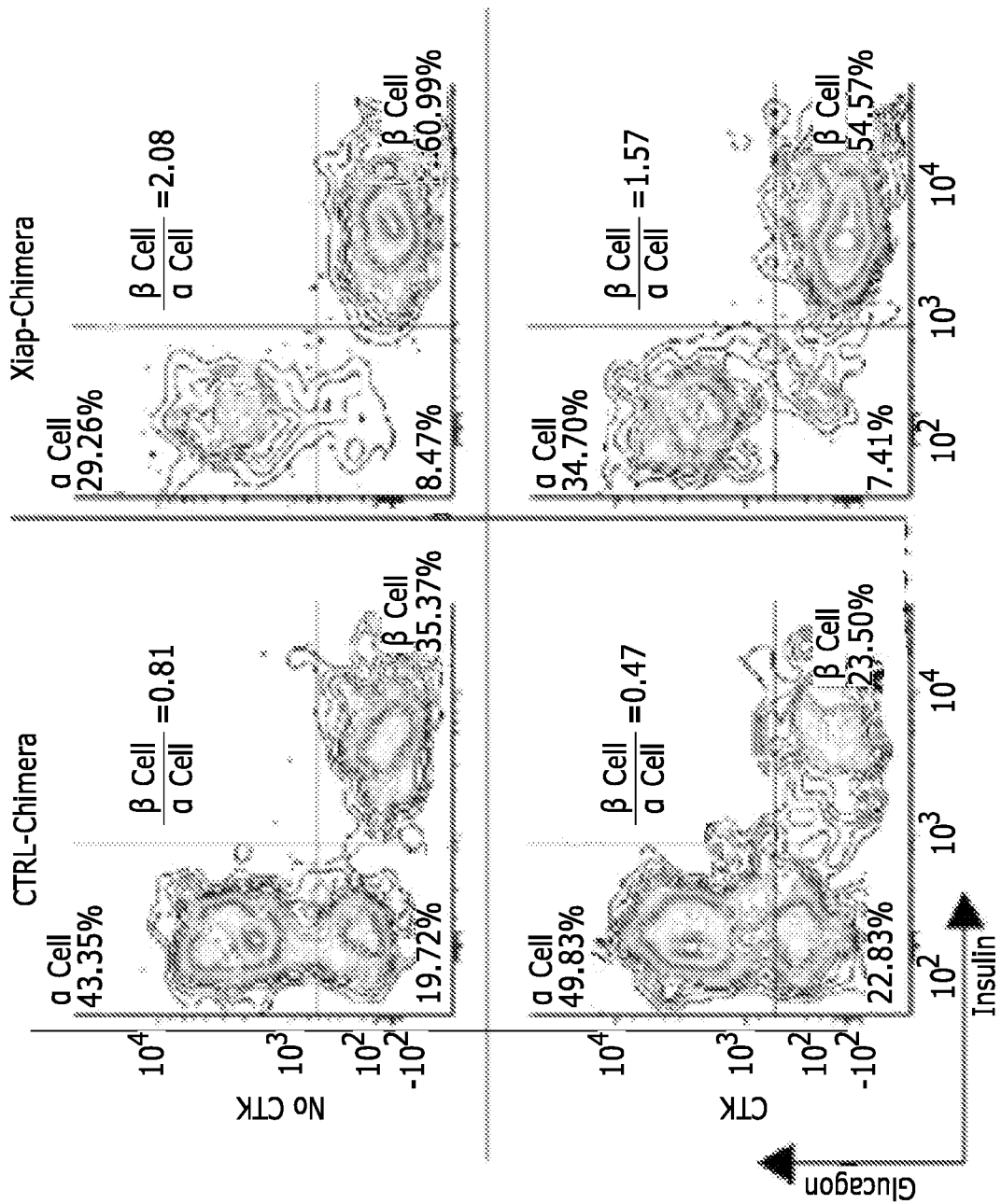

In vitro proof of principle experiments were performed using human islets isolated from cadaveric donors to determine if Xiap-saRNA delivered by aptamer can protect β cell from apoptosis. Xiap-saRNA aptamer chimeras were generated as described in FIG. 12 by conjugating the identified Xiap saRNA (-449, table 2) to either aptamer m12-3773 or aptamer 1-717. FIG. 16A shows the experimental procedure: Freshly-isolated, non-dissociated, human islets (200 IEQ) from cadaveric donor were transfected with Xiap-saRNA by adding the Xiap/saRNA aptamer chimera (5 ug) to the culture. Scramble saRNA/aptamer chimera were used as negative control. 48 hours later, half of the wells were challenged with inflammatory cytokines (IFNg, TNFa, and IL1b) to induce beta cell apoptosis. Beta cell death was evaluated by flow cytometry 24 hours after cytokine challenge by measuring beta/alpha cell ratio after staining for insulin and glucagon. FIG. 16B shows the flow cytometry analysis of single cell suspension of islets treated with scrambled saRNA chimera (CTRL chimera) or XIAP-saRNA/aptamer chimera (Xiap Chimera) and later challenged with cytokines (CTK) or left untreated (No CTK).

Figure 16C:
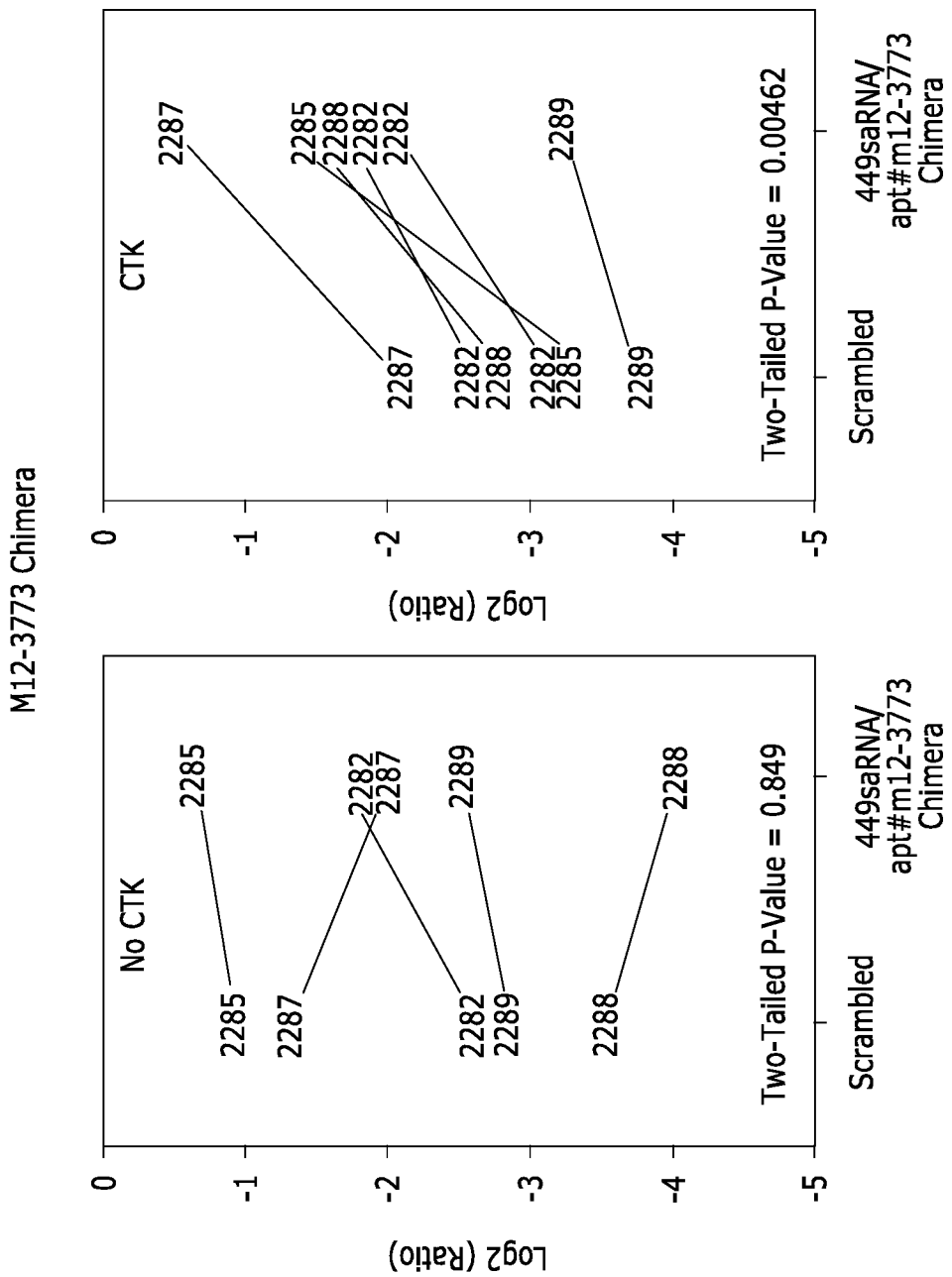
Figure 16C:
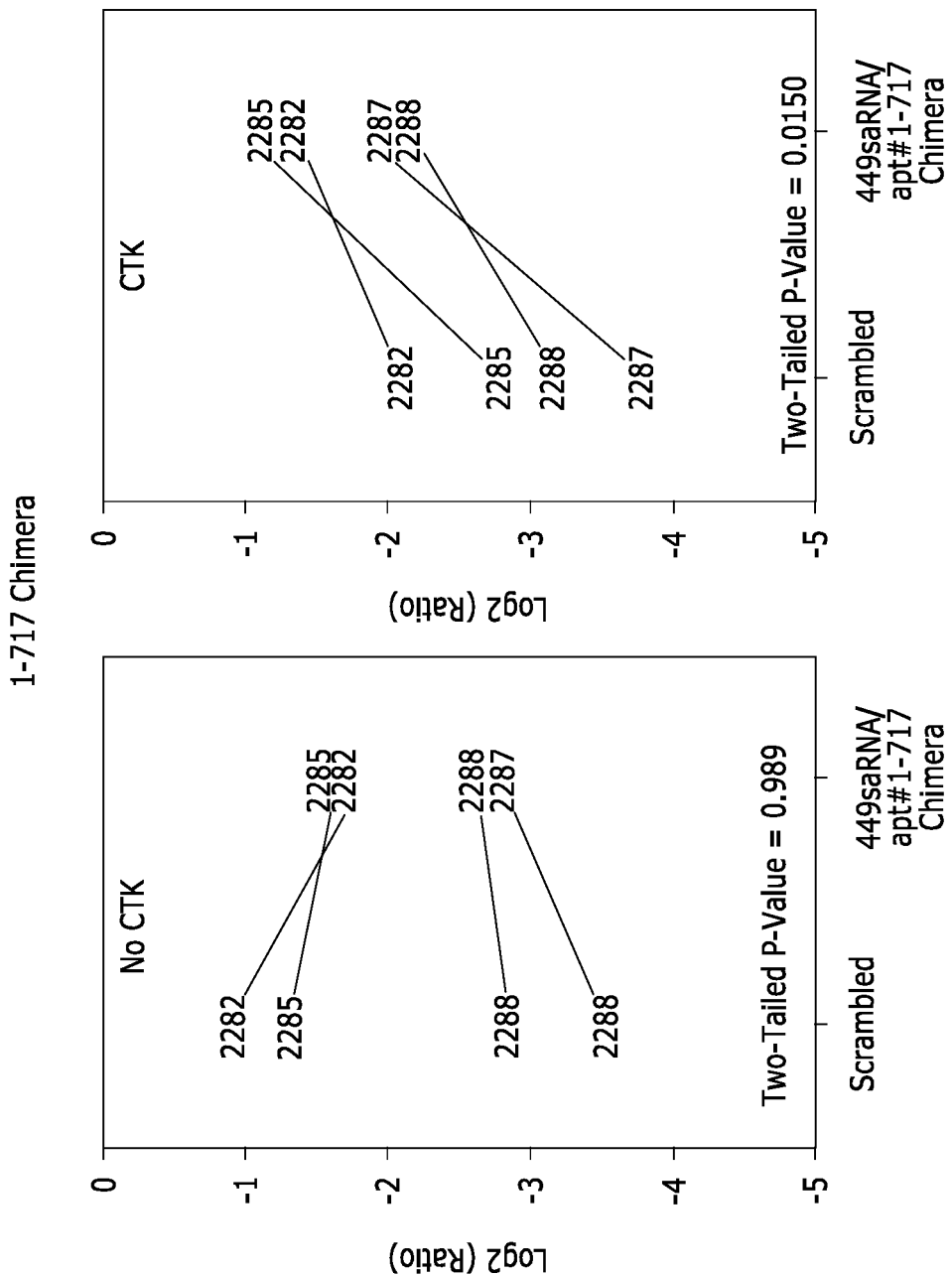

FIG. 16C is a spaghetti plot from 5 independent experiments each with islets from a different cadaveric donor using chimera generated with either aptamer m12-3773 or aptamer 1-717. Paired T test value is reported. Data show that Xiap-saRNA aptamer chimera protect beta cells from cytokine-induced apoptosis.

Interestingly, untreated islets in the absence of cytokines showed higher proportion in α cells (β/α cell ratio=0.8) in the presence of CTRL-chimera (FIG. 16B) and in absence of any chimera (data not shown), suggesting that β cell viability may be affected more than α cells during islet isolation. Addition of cytokines further reduced β cell proportion (β/α cell ratio~0.5). Notably, incubation with Xiap-saRNA/chimera not only prevented the CTKs-induced decrease in β cells (β/α cell ratio~1.6) but also prevented β cell loss associated with islets isolation. These data indicate that saRNA-chimeras can be used to modulate Xiap expression in human islets.

Example 5—Use of Xiap-saRNA/Aptamer Chimera to Prevent Primary Nonfunction

Figure 17:
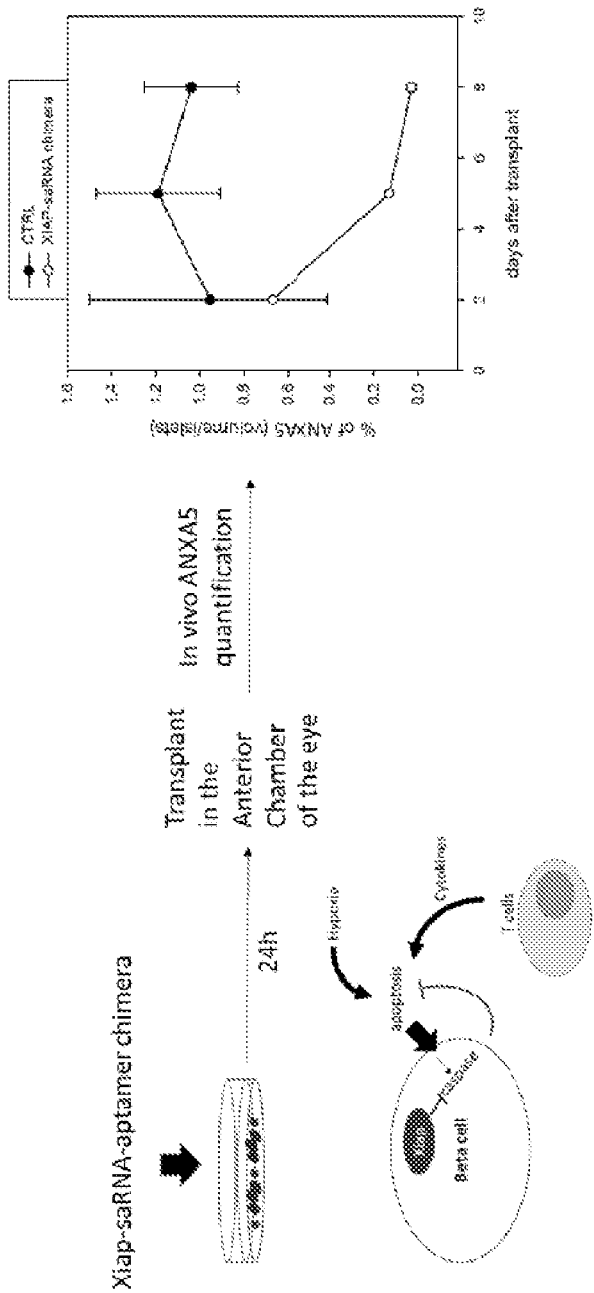
FIG. 17A shows that the Xiap-saRNA/islet specific aptamer chimera protect beta cells from primary nonfunction.
FIG. 17B is a schematic for the experiment described in Example 5.
FIG. 17C: human Islets were cultured in media where chimera was added at 48 h, 24 h and on the day of transplantation 600 IEQ were transplanted per mouse in the left kidney capsule of streptozotocin diabetic NOG mice. Data showed that pretreatment of human islets with aptamer chimera greatly improve the efficacy of islet transplantation with approximately 80% of mice becoming normoglycemic by day 2. In contrast only 50% od mice engrafted with islets (P=0.02; $n_{chimera\ treated}$=10; $n_{untreated}$=8) reverse diabetes and with a delayed kinetic.

Human islets from cadaveric donors were transfected with Xiap-saRNA aptamer chimera or control-chimera as detailed in FIG. 17A Twenty-four hours after transfection, islets were transplanted in the anterior chamber of the eye of immune deficient NSG mice. Islets cell apoptosis was evaluate longitudinally by in vivo annexin V (ANXA5) staining and in vivo microscopy. Data show that treatment with Xiap-saRNA/aptamer chimera before transplantation drastically reduce apoptosis (ANXA5), and thus cellular loss of the graft.

Provided in FIG. 17B is the schematic the Xiap-saRNA/aptamer chimera for graft preservation. As shown in FIG. 17C, human Islets were cultured in media where chimera was added at 48 h, 24 h and on the day of transplantation 600 IEQ were transplanted per mouse in the left kidney capsule of streptozotocin diabetic NOG mice. Data showed that pretreatment of human islets with aptamer chimera greatly improve the efficacy of islet transplantation with approximately 80% of mice becoming normoglycemic by day 2. In contrast only 50% od mice engrafted with islets (P=0.02; $n_{chimera\ treated}$=10; $n_{untreated}$=8) reverse diabetes and with a delayed kinetic.

Example 6—Protect Islets from Allo- and Auto-Immunity in Humanized Mice Via PDL1-saRNA/Aptamer Chimera The clinical importance of PDL1 expression in the maintenance of tissue specific tolerance is highlighted by the success of PDL1-PD1 antagonists in cancer (135). Engagement of PD1 by PDL1 down-regulates effector T cell proliferation and activation, induces T cell cycle arrest and apoptosis, and promotes IL10-producing Treg (136-139). Interestingly, one of the emerging side effect anti-PD1 treatment is T1D140. This suggests that PDL1/PD1 may play an important role in controlling T cell tolerance against β cells. Indeed, in NOD mice PDL1 blockade accelerate T1D in female mice and induce it in male (13). Conversely, PDL1 ectopic expression in syngeneic transplanted islets protects NOD mice against T1D recurrence (12,13). NOD transgenic mice expressing PDL1 under control of the insulin promoter shows delayed incidence in diabetes, reduction T1D incidence, and a systemic, islet specific, T cell anergy (141). In humans, PDL1 polymorphisms is associated with T1D (OR=1.44) (142).

Figure 18A:
FIG. 18. Identification of small activating RNA (saRNA) specific for the human "PDL1" (CD274, Gene ID: 29126).
Figure 18A:
Figure 18B:
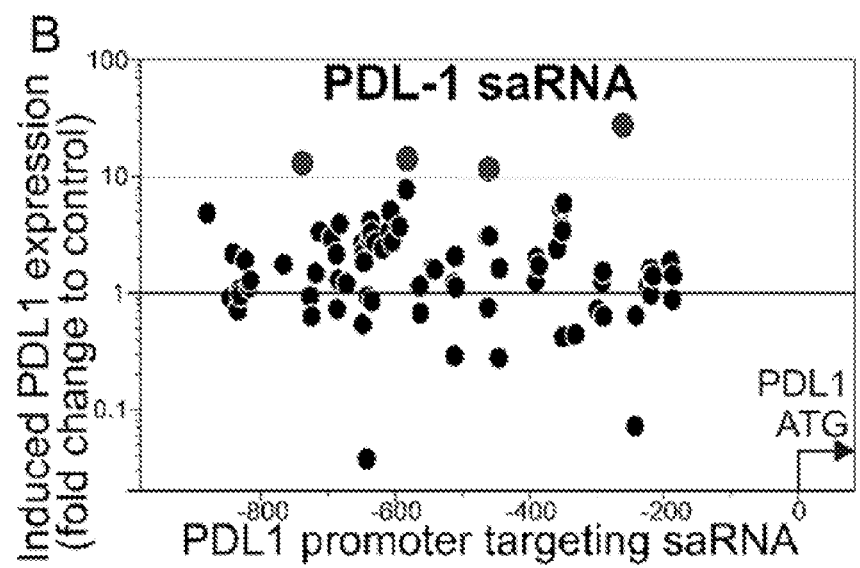

Given the importance that PDL1 expression might play in controlling T cell reactivity to β cells, we identified saRNAs specific for PDL1 (FIG. 18). Briefly, putative candidate sequence of small activating RNA for PDL1 were identified by scanning the PDL1 promoter using publically available algorithms. This analysis return more than 200 putative target saRNA target regions. The 95 putative saRNA with higher score were synthetized and tested for their capacity to up-regulate PDL1 by transfecting the human epithelial cell line A549. qRT-PCR was performed 96 hours after transfection and results normalized on the same cell line transfected with scrambled saRNA. 19 saRNAs were found able to upregulate Xiap expression more than 3 times (range 3.01-63.27) over scrambled saRNA (Table 6).

TABLE 6 saRNA sequences to upregulate human PDL1.

| Position | fold change | PDL1-saRNA | SEQ ID NO: |
|---|---|---|---|
| −261 | 63.2769 | UUUAUCAGAAAGGCGUCCCuu | 394 |
| −583 | 14.1907 | UUAAGGCUGCGGAAGCCUAuu | 395 |
| −739 | 13.0165 | UUGACCUCAAGUGAUCCGCuu | 396 |
| −461 | 11.5844 | GACUUCCUCAAAGUUCCUCuu | 397 |
| −584 | 7.7063 | UAAGGCUGCGGAAGCCUAUuu | 398 |
| −349 | 5.8792 | UAAAAGUCAGCAGCAGACAuu | 399 |
| −353 | 5.2152 | AAGUCAGCAGCAGACCCAUuu | 400 |
| −608 | 5.0249 | GUGAGGGUUAAGAAAGCCCuu | 401 |
| −881 | 4.833 | CUGCAGUUCAAAAUACUGCuu | 402 |
| −637 | 4.1477 | UUUGGGUUAGUGAAUGGGCuu | 403 |
| −683 | 3.9179 | UUUACUUAAGUAUUAUCCCuu | 404 |
| −594 | 3.7109 | GAAGCCUAUUCUAGGUGAGuu | 405 |
| −352 | 3.6316 | AAAGUCAGCAGCAGACCCAuu | 406 |
| −351 | 3.3859 | AAAAGUCAGCAGCAGACCCuu | 407 |
| −609 | 3.3669 | UGAGGGUUAAGAAAGCCCUuu | 408 |
| −713 | 3.3464 | CUAGGUGCUCUCUUUUCUCuu | 409 |
| −636 | 3.28 | CUUUGGGUUAGUGAAUGGGuu | 410 |
| −460 | 3.0587 | UGACUUCCUCAAAGUUCCUuu | 411 |
| −464 | 3.0192 | UUCCUCAAAGUUCCUCGACuu | 412 |

Figures 19A, 19B:
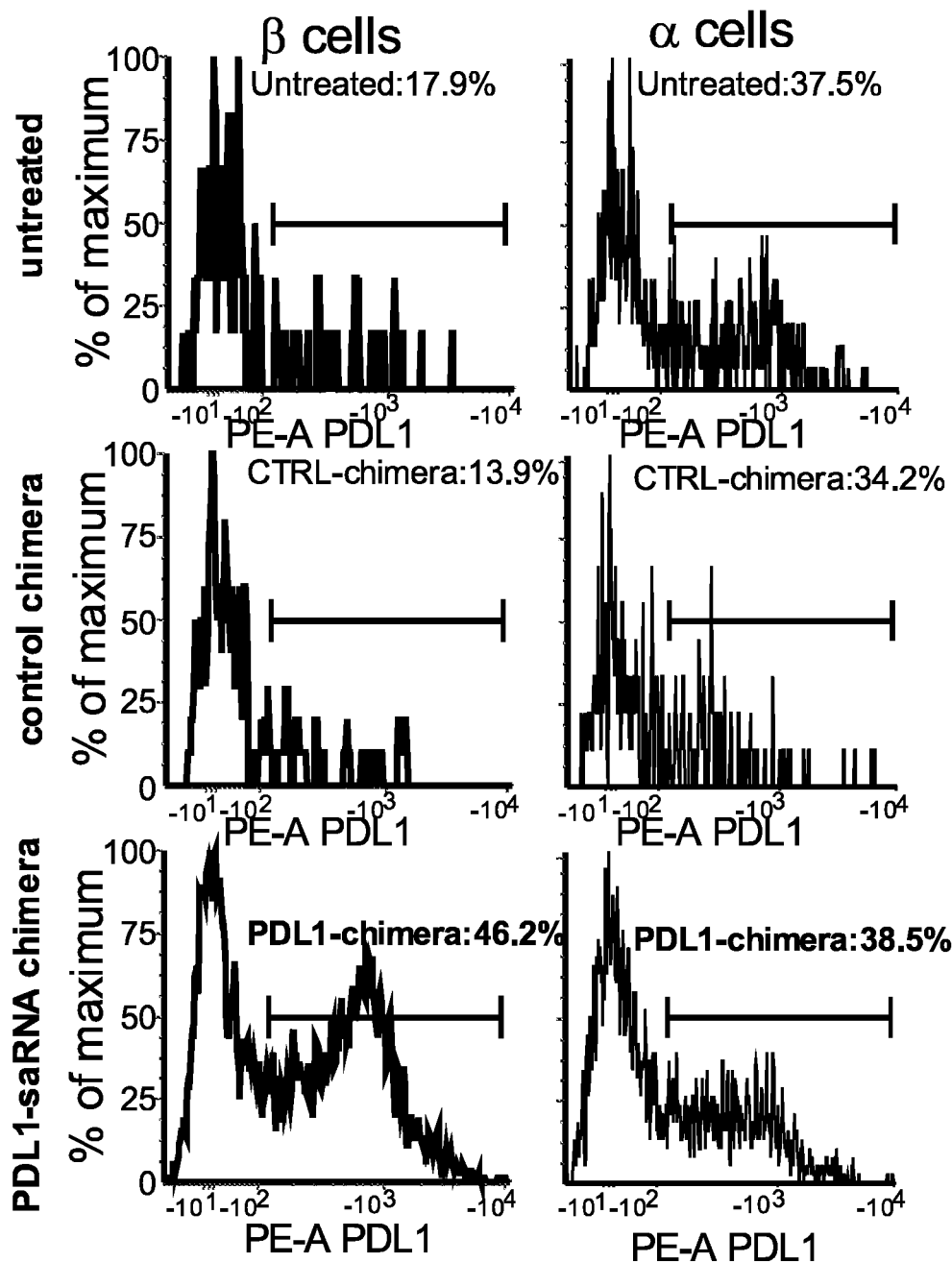
FIG. 19. PDL1-saRNA/islet specific aptamer chimera upregulate PDL1 on human beta cells.

Next whether the islet-specific-aptamers described herein can effectively deliver PDL1-saRNAs to human islets and upregulate PDL1 expression was tested. Aptamer-PDL1-saRNA chimeras were generated by conjugating aptamer 1-717 to PDL1-saRNA-636 (Table 6) as described in FIG. 12. As shown in FIG. 19A, these PDL1-saRNA/aptamer chimera were added to non-dissociated human islets from cadaveric donor. 48 h later, islets were dissociated, labelled with anti-insulin, anti-glucagon and anti-PDL1 antibodies and analyzed by flow cytometry (FIG. 19B). PDL1 expression was evaluated by gating on insulin positive beta cells or glucagon positive alpha cells. While treatment with control chimera does not modify PDL1 expression, treatment with PDL1-saRNA/aptamer significantly upregulate the expression of this important immune modulatory protein on beta cells (FIG. 19B). Interestingly no changes were observed in alpha cells confirming indirectly the preferential binding of this aptamer to beta cells. These proof of principle data indicate that aptamers can be effectively used to deliver functional PDL1-saRNA into human β cells in vitro.

Next, the ability of PDL1-saRNA/aptamer chimera to upregulate PDL1 in vivo was assessed. As shown in FIG. 20A, immune deficient NSG mice were transplanted in the anterior chamber of the eye with human islets from a cadaveric donor. 3 weeks later, mice were treated with PDL1-saRNA(636)/1-717-aptamer chimera generated as described in FIG. 12 and FIG. 19. Scramble-saRNA/aptamer chimera was used as control (CTRL chimera). Five days after treatment, PDL1 expression (white) on the islets (dark gray) was quantified by in vivo labelling with anti-PDL1 antibody and in vivo microscopy (FIG. 20B). Summary of PDL1 expression on the engrafted islets at baseline or 5 days after treatment with PDL1-saRNA/aptamer chimera or scrambled-saRNA/aptamer chimera FIG. 20C).

These results indicated that: i) it is possible to detect PDL1 in human islet cells in vivo, ii) our aptamer chimeras transfect human islets in vivo, and iii) it is possible to upregulate PDL1 in human islets in vivo via aptamer chimera.

Example 7—Assess β Cell Protection from Apoptosis by Aptamer Mediated Xiap Upregulation In the first set of experiments, NSG mice will be engrafted with human islets in the ACE. Three weeks after transplant, mice will be treated with Xiap saRNA-aptamer chimera(s) or control chimera. At different time points, human islet grafts will be challenged by intraocular injection of IL1β, TNF-α, and IFNγ to induce apoptosis in β cells via activation of caspase 3 and 7. Caspase 3 and 7 activity will be evaluated in vivo by our intraocular imaging system using CASP3/7 Green Detection Reagent. This cell-permeant reagent consists of a four-amino acid peptide (DEVD) conjugated to a nucleic acid-binding dye. Upon activation, caspase 3 and 7 cleave the probe, allow the dye to bind to the DNA, and emit a bright, fluorogenic signal that can be detected at the cellular level in the ACE28. Additionally, in vivo staining with anti-Annexin V antibodies will be used to directly measured islet cell apoptosis in vivo (FIG. 7).

The second set of experiment aims to evaluate the effect of Xiap modulation on anti-islet allo-immunity. Briefly, STZ-diabetic NSG mice will be transplanted with 500 IEQ human islets in the ACE or EFP. 3 weeks later mice will be treated with Xiap chimera(s) or scrambled controls. Treatment will be repeated as determine in Aim2b. One week after the first treatment, mice will receive CFSE labelled human T cells mismatched for HLA to the islet. Without any treatment, the adoptive transfer of allogeneic T cells results in graft loss and return to hyperglycemia within 3 weeks. Thus, we will assess the protective effect of Xiap chimera treatment on the human islet allograft survival using as readouts: i) glycemia, ii) human c-peptide plasma levels and, in the ACE group, iii) the longitudinal evaluation of T cell infiltration and volumetric analysis of engrafted islets as we showed in (77,78).

To ensure data reproducibility of Xiap chimera effect among individuals, the chimera identified in the EndoC-BH3 cells will be further validated using primary human islets from 6 cadaveric donors; this will provide 88% of power to detect 1.25SD difference from control in one tailed paired t-test. To avoid artifacts, 3 different readout methods (qPCR, western blot, and enzymatic assay) will be used and at least 3 independent repetitions will be performed for each experiment using human islets from 3 different cadaveric donors. In transplantation studies, a total of 9 mice per group (3 in each repetition) will be used to ensure 90% of power (ANOVA, $\alpha=0.05$) and detect 1.6SD difference to control.

Example 8—Optimize the Dose for In Vivo Silencing of P57Kip2

In a first set of experiments, NSG mice transplanted with 500 IEQ human islets in the EFP will be treated i.v. or s.c. with different doses (6, 20, and 60 pmoles/g) of islets-specific aptamers conjugated with p57kip2siRNA or scrambled siRNA (control-chimera) as negative control. We will use adenovirus encoding the same p57kip2 shRNA-transfected islets as positive control (14). At predefined time-points (e.g., day 1, 2, 3, 4, and 5 after administration), grafts will be harvested, and p57kip2 expression quantified by i) qRT-PCR on laser captured islets, and ii) by quantitative computer assisted immunofluorescence analysis 95. Both techniques are optimized at the Diabetes Research Institute (96,97) and in the laboratories of the PIs95. To evaluate possible dose-dependent toxicity, sera and organs of interest (spleen, liver, lymph nodes, lung, kidney, and brain) will be collected and sent to the mouse pathology laboratory of University of Miami for histopathological evaluation.

In the second set of experiments, NSG mice will be transplanted with 500 IEQ human islets in the ACE. Three weeks later, mice will be treated i.v. or by intraocular injection (i.o) with different doses (6, 20, 60 pm/g) of our aptamer-chimera loaded with p57kip2 siRNA or AF647-scrambled siRNA (control-chimera) as negative control. In vivo transfection efficiency of the AF647 siRNA will be evaluated with our intraocular imaging system 2, 3, 4, 8, and 24 hours after injection (28). At selected time-points (e.g., 2, 3, 4, and 7 days after treatment), graft will be removed and p57kip2 expression quantified by qRT-PCR on islets explanted from the ACE and by i) qRT-PCR on laser capture islets and ii) by quantitative computer assisted immunofluorescence microscopy analysis (95).

Example 9—Optimize Treatment Length and Frequency for Aptamer-Chimera Administration Once the optimal dose and route of administration are identified and the kinetics of p57kip2 silencing evaluated, we will determine the number of administrations of p57kip2siRNA-aptamer chimera needed to induce substantial changes (i.e., ≥100% increase) in β cell mass. Since p57kip2 silencing was shown to induce β cell proliferation only in hyperglycemic mice14, sub-marginal human islet mass (250 IEQ) will be transplanted in the EFP or ACE of NSG mice. 21 days after transplant, mice will be rendered hyperglycemic by streptozotocin (STZ) treatment. STZ selectively eliminates mouse islets as human β are considerably more resistant (98). Once the mice become hyperglycemic (usually 5-6 days after treatment), mice will receive 1, 2, 3, or 4 administration of islet-specific or control aptamer chimeras. The frequency of the aptamer administration will be determined based on the time course established in Example 5. BrdU will be administered in drinking water for ex vivo determination of proliferation. β cell mass in the EPF group will be evaluated longitudinally (baseline, during treatment, 5 and 10 days after the last treatment) by IVIS (FIG. 2). In the ACE group, islets mass will be evaluated by in vivo imaging and quantitative analysis of islet volume (28). Ten days after the last treatment, grafts will be harvested and analyzed by immunostaining to determine (i) β cell proliferation via BrdU and Ki76 staining and (ii) α to β cell ratio.

Example 10—Determine if Aptamer Mediated Silencing can Restore Normoglycemia in Diabetic Mice Transplanted with Sub-Marginal Islet Mass The purpose of this Example is to test if aptamer mediated p57kip2 silencing can restore normoglycemia in diabetic mice transplanted with suboptimal number of human islets.

In the first set of experiments, STZ-diabetic NSG mice maintained on insulin therapy (s.c pellet implant for sustained insulin release) will be transplanted with different quantities of human islets (50, 150, 350 IEQ) in the ACE. Three weeks later, insulin pellets will be removed, and mice will be treated with p57kip2siRNA-aptamer chimera or scrambled control, locally or systemically. To compare this treatment with today gold standard for islets transfection, two additional groups of mice will be treated locally with adenoviral vector encoding for p57kip2shRNA or RFP as control. Pilot experiments using RFP encoding adenovirus will be performed in the ACE to determine the minimal dose necessary for transducing at least 90% of the islets. Transduction efficiency will be quantified using our in vivo imaging system (28). In the experimental groups (which received 50, 150, and 350 IEQ), blood glucose will be used as readout for treatment efficacy in addition to intravital imaging and volume analysis of the ACE islet grafts. The varied sub-marginal islet mass in the different groups may also reveal the degree of the hyperglycemic drive on human islet proliferation.

In the second set of experiments, STZ-diabetic mice will be transplanted in the EFP with the same sub-marginal human islet masses (50, 150, 350 IEQ) and maintained on insulin during the engraftment period. 3 weeks later insulin pellet will be removed and mice will be treated with p57kip2siRNA-aptamer chimera or the scrambled control. We will monitor glycemia and β cell mass by IVIS longitudinally as readouts.

In both sets of experiments, glucose tolerance tests (GTTs) will be performed in mice with restored normoglycemia to further evaluate the islet function under stress conditions.

To ensure reproducibility in the results, at least 3 independent repetitions will be performed for each experiment using human islets from 3 different cadaveric donors. The use a total of 9 mice per experimental group (3 in each repetition) gives 90% of power (One way ANOVA, $\alpha=0.05$) to detect an effect size of 1.6 SD to control. 12 mice per group will be used to accounting for the higher expected variation of the read-out. To minimize readout-specific artifacts, the same phenomenon will be measured with at least 2 independent methods.

REFERENCES CITED

1 Roep, B. O. Diabetes 65, 545-547, (2016).
2 VanBuecken, et al., Pediatric diabetes 15, 84-90, (2014).
3 Keenan et al., Joslin Medalist Study. Diabetes 59, 2846-2853, (2010).
4 Liu et al., Diabetologia 52, 1369-1380, (2009).
5 Rother, et al., Diabetes Care 32, 2251-2257, (2009).
6 Wang et al., Diabetes Care 35, 465-470, (2012).
7 Oram et al., Diabetologia 57, 187-191, (2014).

8 Potter et al., Diabetes 63, 12-19, (2014).
9 Shapiro et al., Nat Rev Endocrinol advance online publication, doi:10.1038/nrendo.2016.178 (2016).
10 Mehrotra et al., IET nanobiotechnology/IET 9, 386-395, doi:10.1049/iet-nbt.2015.0018 (2015).
11 Wu et al., Mol Pharm 7, 1655-1666, doi:10.1021/mp100070j (2010).
12 Li, et al., Diabetes 64, 529-540, doi:10.2337/db13-1737 (2015).
13 Ansari, et al., J Exp Med 198, 63-69, doi:10.1084/jem.20022125 (2003).
14 Avrahami, et al., J Clin Invest 124, 670-674, doi:10.1172/JCI69519 (2014).
15 Ng, et al., Nat Rev Drug Discov 5, 123-132, doi:10.1038/nrd1955 (2006).
16 Alagia, A. & Eritja, R. siRNA and RNAi optimization. Wiley interdisciplinary reviews. RNA, doi:10.1002/wrna.1337 (2016).
17 Abe, et al., Folia pharmacologica Japonica 147, 362-367, doi:10.1254/fpj.147.362 (2016).
18 Bandello, et al., Current pharmaceutical design 21, 4731-4737 (2015).
19 Camorani, et al., Central nervous system agents in medicinal chemistry 15, 126-137 (2015).
20 Kanwar, et al., Current medicinal chemistry 22, 2539-2557 (2015).
21 Lao, et al., ACS nano 9, 2235-2254, (2015).
22 Lee, et al., BMB reports 48, 234-237 (2015).
23 Woodruff, et al., Arteriosclerosis, thrombosis, and vascular biology 35, 2083-2091, (2015).
24 Yu, Y. et al., International journal of molecular sciences 17, 358, (2016).
25 Vater, A. et al., The Journal of Biological Chemistry 288, 21136-21147, (2013).
26 Zheng, et al., Cancer Lett 355, 18-24, doi:10.1016/j.canlet.2014.09.004 (2014).
27 Berman, D. M. et al., Diabetes 65, 1350-1361, (2016).
28 Abdulreda, M. H. et al., Proc Natl Acad Sci U.S.A. 108, 12863-12868, doi:10.1073/pnas.1105002108 (2011).
29 Abdulreda, et al., J Vis Exp, e50466, (2013).
30 Miska, J. et al., J Exp Med 211, 441-456, (2014).
31 Hu, P. P. Recent Advances in Aptamers Targeting Immune System Inflammation, doi:10.1007/s10753-016-0437-9 (2016).
32 Parashar, A., J Clin Diagn Res 10, Be01-06, (2016).
33 Qu, J. et al., Cell Mol Life Sci, doi:10.1007/s00018-016-2345-4 (2016).
34 Sullenger, et al., Science 352, 1417-1420, (2016).
35 Thiel, W. H. et al., PLoS One 7, e43836, doi:10.1371/journal.pone.0043836 (2012).
36 Magalhaes, et al., Mol Ther 20, 616-624, (2012).
37 Farokhzad, et al., Cancer Research 64, 7668-7672 (2004).
38 Chu, et al., Nucleic Acids Res 34, e73, (2006).
39 McNamara, et al., Nat Biotechnol 24, 1005-1015, (2006).
40 Caroli, et al., Bioinformatics 32, 161-164, (2016).
41 Ulrich, et al., Cytometry A 59, 220-231, (2004).
42 Zhu, G. et al. Chem Commun (Camb) 48, 10472-10480, (2012).
43 Zhou, et al., Front Genet 3, 234, (2012).
44 Bagalkot et al., Angew Chem Int Ed Engl 45, 8149-8152 (2006).
45 Huang, et al., Chembiochem 10, 862-868, (2009).
46 Taghdisi, et al., J Drug Target 18, 277-281, (2010).
47 Farokhzad, et al., Proc Natl Acad Sci U.S.A. 103, 6315-6320, (2006).
48 Dhar et al., Proc Natl Acad Sci U.S.A. 105, 17356-17361, (2008).
49 Gu, et al., Proc Natl Acad Sci U.S.A. 105, 2586-2591, (2008).
50 Cao, et al., Angew Chem Int Ed Engl 48, 6494-6498, (2009).
51 Kang, et al., Chem Commun (Camb) 46, 249-251, (2010).
52 Zhang, et al., ChemMedChem 2, 1268-1271, (2007).
53 Huang, et al., Anal Chem 80, 567-572, (2008).
54 Javier, et al., Bioconjug Chem 19, 1309-1312, (2008).
55 Li, et al., Chem Commun (Camb) 46, 392-394, (2010).
56 Guo, P., J Nanosci Nanotechnol 5, 1964-1982 (2005).
57 Guo, et al., Hum Gene Ther 16, 1097-1109, (2005).
58 Wullner, et al., Curr Cancer Drug Targets 8, 554-565 (2008).
59 Zhou, et al., Mol Ther 16, 1481-1489, (2008).
60 Dassie, et al., Nat Biotechnol 27, 839-849, (2009).
61 Zhou, et al., Curr Top Med Chem 9, 1144-1157 (2009).
62 Pastor, et al., Nature 465, 227-230, (2010).
63 Wheeler, et al., J Clin Invest 121, 2401-2412, (2011).
64 Wheeler, et al., Mol Ther 21, 1378-1389, (2013).
65 Neff, et al., Science translational medicine 3, 66ra66, (2011).
66 Zhou, et al., Mol Ther 21, 192-200, (2013).
67 Subramanian, et al., Nucleic acid therapeutics, (2015).
68 Zhou, et al., Methods Mol Biol 1297, 169-185, (2015).
69 Hao, et al., Drug delivery, 1-8, (2015).
70 Gilboa-Geffen et al., Mol Cancer Ther 14, 2279-2291, (2015).
71 Song, P. et al. Biochem Biophys Res Commun 452, 1040-1045, (2014).
72 Lai, et al., Biomaterials 35, 2905-2914, (2014).
73 Hu et al., Nucleic acids 3, e209, (2014).
74 Herrmann, et al., J Clin Invest 124, 2977-2987, (2014).
75 Bruno, J. G., Molecules (Basel, Switzerland) 20, 6866-6887, (2015).
76 Abdulreda, et al., Proc Natl Acad Sci U.S.A., 108, 12863-12868, (2011).
77 Ilegems et al., Proc Natl Acad Sci U.S.A., doi:10.1073/pnas.1313696110 (2013).
78 Almaca, et al. Proc Natl Acad Sci USA, doi:10.1073/pnas.1414053111 (2014).
79 Becker, et al., J Biol Chem 269, 21234-21238 (1994).
80 Flotte, et al., Diabetes 50, 515-520 (2001).
81 Yang, et al., Pharm Res 19, 968-975 (2002).
82 Loiler, et al., Gene Ther 10, 1551-1558, (2003).
83 Bain, et al., Diabetes 53, 2190-2194 (2004).
84 Hanayama, et al., Cell Medicine 8, 31-38, (2015).
85 Thomas, et al., Nat Rev Genet 4, 346-358, (2003).
86 Bottino, et al., Gene Ther 10, 875-889, (2003).
87 Giannoukakis, et al., American journal of therapeutics 12, 512-528 (2005).
88 Jimenez-Moreno, et al., Curr Gene Ther 15, 436-446 (2015).
89 Mehta, N., Stone, J. & Whitelaw, A. Practical management of hyperinsulinism in infancy. Archives of disease in childhood. Fetal and neonatal edition 84, F218 (2001).
90 Menni, et al., Pediatrics 107, 476-479 (2001).
91 de Lonlay, et al., J Clin Invest 100, 802-807, (1997).
92 Kassem, et al., Diabetes 50, 2763-2769, (2001).
93 dilorio, et al., Pancreas 40, 1147-1149, (2011).
94 Borriello, et al., Molecular Cancer Research 9, 1269-1284, (2011).
95 Kassem, et al., Diabetes 50, 2763 (2001).
96 Zhang, et al., J Proteomics 150, 149-159, (2017).
97 Richardson, et al., Diabetologia 59, 2448-2458, (2016).

98 Yang et al., Endocrinology 143, 2491-2495, (2002).
99 Mathis, et al., Nature 414, 792-798, (2001).
100 Butler, et al., Diabetologia 50, 2323-2331, (2007).
101 Meier, et al., Diabetologia 48, 2221-2228, (2005).
102 Hui, et al., Journal of Cellular Physiology 200, 177-200, (2004).
103 Turley, et al., The Journal of Experimental Medicine 198, 1527-1537, (2003).
104 Viste, et al., Transplant Proc 22, 808-809 (1990).
105 Deng, et al., Transplant Proc 29, 2062-2063 (1997).
106 Hughes, et al., Current diabetes reviews 6, 274-284 (2010).
107 Bellin, et al., Ann Surg 261, 21-29, (2015).
108 Lazard, et al., Diabetes/metabolism research and reviews 28, 475-484, (2012).
109 Emamaullee, et al., Am J Transplant 5, 1297-1305, (2005).
110 Plesner, et al., Diabetes 54, 2533-2540 (2005).
111 Emamaullee, et al., Diabetes 54, 2541-2548 (2005).
112 Li, et al., Proc Natl Acad Sci U.S.A. 103, 17337-17342, (2006).
113 Huang, et al., PLoS One 5, e8848, (2010).
114 Janowski, et al., Nature chemical biology 3, 166-173, (2007).
115 Kosaka, et al., Nucleic acid therapeutics 22, 335-343, (2012).
116 Pan, et al., Gene 527, 102-108, (2013).
117 Sakurai, et al., Cancer Gene Ther 21, 164-170, (2014).
118 Ren, et al., Prostate 73, 1591-1601, (2013).
119 Turner, et al., Cell Cycle 13, 772-781, (2014).
120 Wang, et al., Cancer Res 70, 10182-10191, (2010).
121 Wang, et al., Biochem J 443, 821-828, (2012).
122 Qin, et al., World journal of surgical oncology 10, 11, (2012).
123 Meng, et al., Nucleic Acids Research 44, 2274-2282, (2016).
124 Schwartz, et al., Nature structural & molecular biology 15, 842-848, (2008).
125 Weinberg, et al., Nucleic Acids Res 35, 7303-7312, (2007).
126 Guo, et al., RNA biology 11, 1221-1225, (2014).
127 Chen, et al., The journal of sexual medicine 8, 2773-2780, (2011).
128 Chen, et al., Mol Cancer Ther 7, 698-703, (2008).
129 Dong, et al., Yonsei Med J 55, 324-330, (2014).
130 Yang, et al., Int J Biochem Cell Biol 45, 1338-1346, (2013).
131 Chu, et al., Nucleic Acids Res 38, 7736-7748, (2010).
132 Benazra, et al., Molecular metabolism 4, 916-925, (2015).
133 Wei et al., The Journal of Clinical Investigation 121, 3395-3397, (2011).
134 Brehm, et al., Cold Spring Harbor Perspectives in Medicine 2, a007757, (2012).
135 Hughes, et al., Trends Immunol 37, 462-476, (2016).
136 Pardoll, et al., Semin Oncol 42, 523-538, (2015).
137 Francisco, et al., Immunological reviews 236, 219-242, (2010).
138 Keir, et al., J Immunol 179, 5064-5070 (2007).
139 Lee, et al., J Immunol 171, 6929-6935 (2003).
140 Hughes, et al., Diabetes Care 38, e55-57, (2015).
141 Wang, et al., Diabetes 57, 1861-1869, (2008).
142 Pizarro, et al., Diabetes/metabolism research and reviews 30, 761-766, (2014).
143 Goldman, et al., Br J Haematol 103, 335-342 (1998).
144 Mazurier, et al., J Interferon Cytokine Res 19, 533-541 (1999).
145 Ito, et al., Blood 100, 3175-3182 (2002).
146 Ishikawa, et al., Blood 106, 1565-1573 (2005).
147 Berges, et al., Virology 373, 342-351 (2008).
148 Brainard, et al., Virol 83, 7305-7321 (2009).
149 Brehm, et al., Clin Immunol 135, 84-98.
150 Gorantla, et al., J Immunol 184, 7082-7091.
151 Gorantla, et al., J Virol 79, 2124-2132 (2005).
152 Joseph, et al., J Virol 84, 6645-6653.
153 Kumar, et al., Cell 134, 577-586 (2008).
154 Lepus et al., Hum Immunol 70, 790-802, (2009).
155 Mukherjee, et al., Mol Ther 18, 803-811.
156 Nakata, et al., J Virol 79, 2087-2096 (2005).
157 Rajesh, et al., Hum Immunol 71, 551-559.
158 Sato, et al., Vaccine 28 Suppl 2, B32-37.
159 Watanabe, et al., Blood 109, 212-218 (2007).
160 Akkina, et al., PLoS One 6, e20169, (2011).
161 Gonzalez, et al., Immunol Res 57, 326-334, (2013).
162 Shultz, et al., J Immunol 174, 6477-6489 (2005).
163 Giannelli, et al., Cytometry B Clin Cytom 74, 349-355 (2008).
164 Shapiro, et al., Diabetologia 45, 224-230, (2002).
165 Borrello, et al., Blood 114, 1736 (2009).
166 Serafini, et al., Cancer Res 64, 6337-6343, (2004).
167 Strbo, et al., Am J Reprod Immunol 59, 407-416, (2008).
168 Armitage P, B. G., and Matthews J N. Statistical Methods in Medical Research, Fourth Edition. (Blackwell Scientific, 2001).
169 Brown H, P., R. Applied Mixed Models in Medicine. (Wiley, 1999).
170 Hosmer D W, L. S. Applied Logistic Regression, 2nd edition. (Wiley, 2000).
171 Machin D, C. Y., and Parmar MKB. Survival Analysis: A Practical Approach. Second Edition. (John Wiley & Sons, 2006).

What is claimed is:

1. A method of modulating beta cell proliferation comprising contacting the beta cell with a construct comprising an aptamer conjugated to a therapeutic RNA in an amount effective to modulate proliferation of the beta cell, wherein the therapeutic RNA is a siRNA or a saRNA, and wherein the aptamer is specific for clusterin (SEQ ID NO: 414) expressed on islets of Langerhans or "Transmembrane emp24 domain-containing protein 6" (TMED6, Genbank Accession No. NM144676.1) expressed on islets of Langerhans.

2. The method of claim 1, wherein the aptamer comprises the nucleotide sequence set forth in SEQ ID NO: 264 or SEQ ID NO: 259.

3. A method for inhibiting tissue graft apoptosis in a subject in need thereof comprising contacting the tissue graft with a construct comprising an aptamer conjugated to a therapeutic RNA, in an amount effective to inhibit apoptosis of the tissue graft, wherein the therapeutic RNA is a siRNA or a saRNA, and wherein the aptamer is specific for clusterin (SEQ ID NO: 414) expressed on islets of Langerhans or "Transmembrane emp24 domain-containing protein 6" (TMED6, NM144676.1) expressed on islets of Langerhans.

4. The method of claim 3, wherein the aptamer comprises the nucleotide sequence set forth in SEQ ID NO: 264 or SEQ ID NO: 259.

5. A method for protecting a beta cell from T-cell mediated cytotoxicity of the beta cell comprising contacting the beta cell with a construct comprising an aptamer conjugated to a therapeutic RNA, in an amount effective to inhibit T cell mediated cytotoxicity of the beta cell, wherein the therapeutic RNA is a siRNA or a saRNA, and wherein the aptamer is specific for clusterin (SEQ ID NO: 414) expressed on islets of Langerhans or "Transmembrane emp24 domain-containing protein 6" (TMED6, NM144676.1) expressed on islets of Langerhans.

6. The method of claim 5, wherein the aptamer comprises the nucleotide sequence set forth in SEQ ID NO: 264 or SEQ ID NO: 259.

7. A method for treating diabetes in a subject in need thereof comprising administering to the subject a construct comprising an aptamer conjugated to a therapeutic RNA, wherein the therapeutic RNA is a siRNA or a saRNA, and wherein the aptamer is specific for clusterin (SEQ ID NO: 414) expressed on islets of Langerhans or "Transmembrane emp24 domain-containing protein 6" (TMED6, NM144676.1) expressed on islets of Langerhans.

8. The method of claim 7, wherein the aptamer comprises the nucleotide sequence set forth in SEQ ID NO: 264 or SEQ ID NO: 259.

9. A method of delivering a therapeutic RNA to islets of Langerhans in a subject comprising administering construct comprising an aptamer conjugated to a therapeutic RNA to the subject, wherein the therapeutic RNA is a siRNA or a saRNA, and wherein the aptamer is specific for clusterin (SEQ ID NO: 414) expressed on islets of Langerhans or "Transmembrane emp24 domain-containing protein 6" (TMED6, NM144676.1) expressed on islets of Langerhans.

10. The method of claim 9, wherein the aptamer comprises the nucleotide sequence set forth in SEQ ID NO: 264 or SEQ ID NO: 259.

* * * * *

SEQUENCE LISTING

<160> NUMBER OF SEQ ID NOS: 416

<210> SEQ ID NO 1
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 1

```
ggaggagcua cgaugcggcc gauuucguca uccuccauac caucgccuua ccguuccgcg      60
ucagacgacu cgcugaggau ccgaca                                            86
```

```
<210> SEQ ID NO 2
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 2
ggaggagcua cgaugcggcc gucucgcucu caucccaugc acgaaaccuc ucucacugca      60
cagacgacuc gcugaggauc cgaca                                            85

<210> SEQ ID NO 3
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 3
ggaggagcua cgaugcggug aauucuuccg gcacuuuguc aucuucaccc ccaugcugca      60
cagacgacuc gcugaggauc cgaca                                            85

<210> SEQ ID NO 4
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 4
ggaggagcua cgaugcggcc gauuucguca uccuccauac caucgccuca ccguuccgcg      60
ucagacgacu cgcugaggau ccgaca                                           86

<210> SEQ ID NO 5
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 5
ggaggagcua cgaugcggcc gauuucguca uccuccacac caucgccuua ccguuccgcg      60
ucagacgacu cgcugaggau ccgaca                                           86

<210> SEQ ID NO 6
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 6
ggaggagcua cgaugcggcc gauuucguca uccuccguac caucgccuua ccguuccgcg      60
ucagacgacu cgcugaggau ccgaca                                           86

<210> SEQ ID NO 7
<211> LENGTH: 86
<212> TYPE: DNA
<213> ORGANISM: Artificial Sequence
<220> FEATURE:
<223> OTHER INFORMATION: Synthetic Polynucleotide
```

-continued

<400> SEQUENCE: 7
ggaggagcua cgaugcggcc caucacuccc gcguauugcg aacgcaucgu uauuuagccg    60
ucagacgacu cgcugaggau ccgaca                                        86

<210> SEQ ID NO 8
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 8
ggaggagcua cgaugcgguc gauuucguca uccuccauac caucgccuua ccguccgcg    60 ucagacgacu cgcugaggau ccgaca                                        86

<210> SEQ ID NO 9
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 9
ggaggagcua cgaugcggcc gauuucguca uccuccauac caucgucuua ccguccgcg    60 ucagacgacu cgcugaggau ccgaca                                        86

<210> SEQ ID NO 10
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 10
ggaggagcua cgaugcggcc gauuucguca uccuccauac caucgccuua ccgcuccgcg    60
ucagacgacu cgcugaggau ccgaca                                        86

<210> SEQ ID NO 11
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 11
ggaggagcua cgaugcggcc gauuucguca uccuccaugc caucgccuua ccguccgcg    60 ucagacgacu cgcugaggau ccgaca                                        86

<210> SEQ ID NO 12
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 12
ggaggagcua cgaugcggcc gauuucguca uccuccauac caucgcccua ccguccgcg    60 ucagacgacu cgcugaggau ccgaca                                        86

<210> SEQ ID NO 13
<211> LENGTH: 86

<212> TYPE: DNA
<213> ORGANISM: Artificial Sequence
<220> FEATURE:
<223> OTHER INFORMATION: Synthetic Polynucleotide

<400> SEQUENCE: 13
ggaggagcua cgaugcggcc gauuucguca uccuccauac caucgccuug ccguuccgcg    60
ucagacgacu cgcugaggau ccgaca                                         86

<210> SEQ ID NO 14
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 14
ggaggagcua cgaugcggcc gauuucguca uccuccauac caucgccuua ccauuccgcg    60
ucagacgacu cgcugaggau ccgaca                                         86

<210> SEQ ID NO 15
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 15
ggaggagcua cgaugcggcc gauuucguca uccccauac caucgccuua ccguuccgcg     60
ucagacgacu cgcugaggau ccgaca                                         86

<210> SEQ ID NO 16
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 16
ggaggagcua cgaugcggcc gauaucguca uccuccauac caucgccuua ccguuccgcg    60
ucagacgacu cgcugaggau ccgaca                                         86

<210> SEQ ID NO 17
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 17
ggaggagcua cgaugcggcc gauuucguca uccuccauac caucgccuac cguuccgcgu    60
cagacgacuc gcugaggauc cgaca                                          85

<210> SEQ ID NO 18
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 18
ggaggagcua cgaugcggug uacacugauu gccuuugugu uaugagcgac agaucugcca    60
gacagacgac ucgcugagga uccgaca    87

<210> SEQ ID NO 19
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 19
ggaggagcua cgaugcggac cuuguuuucc ucguaccccc acuucccccau uucucccugc    60 ucagacgacu cgcugaggau ccgaca    86

<210> SEQ ID NO 20
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 20
ggaggagcua cgaugcggcc gaucucguca uccuccauac caucgccuua ccguuccgcg    60
ucagacgacu cgcugaggau ccgaca    86

<210> SEQ ID NO 21
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 21
ggaggagcua cgaugcggcc gauuucguca uccuccauac caucgccuua ccgucccgcg    60
ucagacgacu cgcugaggau ccgaca    86

<210> SEQ ID NO 22
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 22
ggaggagcua cgaugcggcc gauuucguca uccuccauac cgucgccuua ccguuccgcg    60
ucagacgacu cgcugaggau ccgaca    86

<210> SEQ ID NO 23
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 23
ggaggagcua cgaugcggcc gauuucgucg uccuccauac caucgccuua ccguuccgcg    60
ucagacgacu cgcugaggau ccgaca    86

<210> SEQ ID NO 24

```
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 24
ggaggagcua cgaugcgggg aagcaacacu uagucgcgau ugauacgugc gcagucauca      60
gacagacgac ucgcugagga uccgaca                                         87

<210> SEQ ID NO 25
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 25
ggaggagcua cgaugcggcc gauuucgcca uccuccauac caucgccuua ccguuccgcg      60
ucagacgacu cgcugaggau ccgaca                                          86

<210> SEQ ID NO 26
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 26
ggaggagcua cgaugcggcc gauuucguca uccuccauac caucgccuuc cguuccgcgu      60
cagacgacuc gcugaggauc cgaca                                           85

<210> SEQ ID NO 27
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 27
ggaggagcua cgaugcggcc gauuucguca uccuccauau caucgccuua ccguuccgcg      60
ucagacgacu cgcugaggau ccgaca                                          86

<210> SEQ ID NO 28
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 28
ggaggagcua cgaugcggcc gauuucguca cccuccauac caucgccuua ccguuccgcg      60
ucagacgacu cgcugaggau ccgaca                                          86

<210> SEQ ID NO 29
<211> LENGTH: 86
<212> TYPE: DNA
<213> ORGANISM: Artificial Sequence
<220> FEATURE:
<223> OTHER INFORMATION: Synthetic Polynucleotide
```

-continued

<400> SEQUENCE: 29
ggaggagcua cgaugcggcc gacuucguca uccuccauac caucgccuua ccguuccgcg    60
ucagacgacu cgcugaggau ccgaca                                        86

<210> SEQ ID NO 30
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 30
ggaggagcua cgaugcggcc gauuucguca uccuccauac caucgccuua ccuuccgcgu    60
cagacgacuc gcugaggauc cgaca                                         85

<210> SEQ ID NO 31
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 31
ggaggagcua cgaugcggcc gauuucguca uccuccauac caucgccuua ccguuccgca    60
gucagacgac ucgcugagga uccgaca                                       87

<210> SEQ ID NO 32
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 32
ggaggagcua cgaugcggcc gauuucguca uccuccuuac caucgccuua ccguuccgcg    60
ucagacgacu cgcugaggau ccgaca                                        86

<210> SEQ ID NO 33
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 33
ggaggagcua cgaugcggcc gauuucguca uccuucauac caucgccuua ccguuccgcg    60
ucagacgacu cgcugaggau ccgaca                                        86

<210> SEQ ID NO 34
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 34
ggaggagcua cgaugcggcc gauuucguca uccuccauac uaucgccuua ccguuccgcg    60
ucagacgacu cgcugaggau ccgaca                                        86

<210> SEQ ID NO 35

```
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 35
ggaggagcua cgaugcggcc gauuucauca uccuccauac caucgccuua ccguuccgcg      60
ucagacgacu cgcugaggau ccgaca                                          86

<210> SEQ ID NO 36
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 36
ggaggagcua cgaugcggcc gauuucguca uccuccauac caucgccuua ccuuccgcg      60 ucagacgacu cgcugaggau ccgaca                                          86

<210> SEQ ID NO 37
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 37
ggaggagcua cgaugcggcc gauuucguca uccucuauac caucgccuua ccguuccgcg      60
ucagacgacu cgcugaggau ccgaca                                          86

<210> SEQ ID NO 38
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 38
ggaggagcua cgaugcggcc gauuucguca uccccaaac caucgccuua ccguuccgcg      60
ucagacgacu cgcugaggau ccgaca                                          86

<210> SEQ ID NO 39
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 39
ggaggagcua cgaugcggcc gauuucguca uccuccauac caucgccuua ucguuccgcg      60
ucagacgacu cgcugaggau ccgaca                                          86

<210> SEQ ID NO 40
<211> LENGTH: 86
<212> TYPE: DNA
<213> ORGANISM: Artificial Sequence
<220> FEATURE:
<223> OTHER INFORMATION: Synthetic Polynucleotide
```

<400> SEQUENCE: 40
ggaggagcua cgaugcggcc gauuccguca uccuccauac caucgccuua ccguuccgcg    60
ucagacgacu cgcugaggau ccgaca                                        86

<210> SEQ ID NO 41
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 41
ggaggagcua cgaugcggcu gauuucguca uccuccauac caucgccuua ccguuccgcg    60
ucagacgacu cgcugaggau ccgaca                                        86

<210> SEQ ID NO 42
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 42
ggaggagcua cgaugcggcc gauuuucguc auccuccaua ccaucgccuu accguuccgc    60
gucagacgac ucgcugagga uccgaca                                       87

<210> SEQ ID NO 43
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 43
ggaggagcua cgaugcggcc gauuucguca uccucaauac caucgccuua ccguuccgcg    60
ucagacgacu cgcugaggau ccgaca                                        86

<210> SEQ ID NO 44
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 44
ggaggagcua cgaugcggcc gauuucguca uccuccauac caucgccuuc ccguuccgcg    60
ucagacgacu cgcugaggau ccgaca                                        86

<210> SEQ ID NO 45
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 45
ggaggagcua cgaugcggau uaccaacuug aacgccgaga guguggucac guuucugca    60 gacagacgac ucgcugagga uccgaca                                       87

<210> SEQ ID NO 46

```
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 46
ggaggagcua cgaugcggcc gauuucguca uccuccauac caucgccuua ccguuucgcg      60
ucagacgacu cgcugaggau ccgaca                                          86

<210> SEQ ID NO 47
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 47
ggaggagcua cgaugcggcc gauuucguau ccuccauacc aucgccuuac cguccgcgu       60 cagacgacuc gcugaggauc cgaca                                           85

<210> SEQ ID NO 48
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 48
ggaggagcua cgaugcgguu augcguuuaa gucauugacg cguuacacug gagggggcca      60
gacagacgac ucgcugagga uccgaca                                         87

<210> SEQ ID NO 49
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 49
ggaggagcua cgaugcggcc gauuucguca uccuccauac caucgccuua ccguccgca       60 ucagacgacu cgcugaggau ccgaca                                          86

<210> SEQ ID NO 50
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 50
ggaggagcua cgaugcggcc gauuucguca uccuccauaa caucgccuua ccguccgcg       60 ucagacgacu cgcugaggau ccgaca                                          86

<210> SEQ ID NO 51
<211> LENGTH: 85
<212> TYPE: DNA
<213> ORGANISM: Artificial Sequence
<220> FEATURE:
<223> OTHER INFORMATION: Synthetic Polynucleotide
```

<400> SEQUENCE: 51
ggaggagcua cgaugcggcc gauuucguca uccuccuacc aucgccuuac cguuccgcgu    60
cagacgacuc gcugaggauc cgaca                                          85

<210> SEQ ID NO 52
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 52
ggaggagcua cgaugcggcc gauuucguua uccuccauac caucgccuua ccguuccgcg    60
ucagacgacu cgcugaggau ccgaca                                         86

<210> SEQ ID NO 53
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 53
ggaggagcua cgaugcggcc gauuucguca uccuccauac caucgccaua ccguuccgcg    60
ucagacgacu cgcugaggau ccgaca                                         86

<210> SEQ ID NO 54
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 54
ggaggagcua cgaugcggcc gauuucguca uccuccauac caucgccuaa ccguuccgcg    60
ucagacgacu cgcugaggau ccgaca                                         86

<210> SEQ ID NO 55
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 55
ggaggagcua cgaugcggcc gauuucguca uccuccauac caucgcuuua ccguuccgcg    60
ucagacgacu cgcugaggau ccgaca                                         86

<210> SEQ ID NO 56
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 56
ggaggagcua cgaugcggcc gauuucguca uccuccauac cauugccuua ccguuccgcg    60
ucagacgacu cgcugaggau ccgaca                                         86

<210> SEQ ID NO 57

```
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 57
ggaggagcua cgaugcggcc gauuucguca uacuccauac caucgccuua ccguuccgcg      60
ucagacgacu cgcugaggau ccgaca                                          86

<210> SEQ ID NO 58
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 58
ggaggagcua cgaugcggcc gauuucguca uccuccauag caucgccuua ccguuccgcg      60
ucagacgacu cgcugaggau ccgaca                                          86

<210> SEQ ID NO 59
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 59
ggaggagcua cgaugcggcc gauuucguca uccuccauac caucgccuua cccuuccgcg      60
ucagacgacu cgcugaggau ccgaca                                          86

<210> SEQ ID NO 60
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 60
ggaggagcua cgaugcggcc gauuucguaa uccuccauac caucgccuua ccguuccgcg      60
ucagacgacu cgcugaggau ccgaca                                          86

<210> SEQ ID NO 61
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 61
ggaggagcua cgaugcggcc gauuucguca uccuccauac caucaccuua ccguuccgcg      60
ucagacgacu cgcugaggau ccgaca                                          86

<210> SEQ ID NO 62
<211> LENGTH: 86
<212> TYPE: DNA
<213> ORGANISM: Artificial Sequence
<220> FEATURE:
<223> OTHER INFORMATION: Synthetic Polynucleotide
```

```
<400> SEQUENCE: 62
ggaggagcua cgaugcggcc gauuucguca uccuccauac caucgccuuu ccguuccgcg      60
ucagacgacu cgcugaggau ccgaca                                          86

<210> SEQ ID NO 63
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 63
ggaggagcua cgaugcggcc caucccuccc gcguauugcg aacgcaucgu uauuuagccg      60
ucagacgacu cgcugaggau ccgaca                                          86

<210> SEQ ID NO 64
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 64
ggaggagcua cgaugcggua auucucagga ggugcggaac gggauaugga uuguucgcca     60
gacagacgac ucgcugagga uccgaca                                         87

<210> SEQ ID NO 65
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 65
ggaggagcua cgaugcggcc gauuucguca uccuccaucc caucgccuua ccguuccgcg     60
ucagacgacu cgcugaggau ccgaca                                          86

<210> SEQ ID NO 66
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 66
ggaggagcua cgaugcggcc gauuucguca ucauccauac caucgccuua ccguuccgcg     60
ucagacgacu cgcugaggau ccgaca                                          86

<210> SEQ ID NO 67
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 67
ggaggagcua cgaugcggug aauucuuccg gcacuuuguc aucuucacuc ccaugcugca     60
cagacgacuc gcugaggauc cgaca                                           85

<210> SEQ ID NO 68
```

```
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 68
ggaggagcua cgaugcggcc gauuucguca uccuacauac caucgccuua ccguuccgcg     60
ucagacgacu cgcugaggau ccgaca                                         86

<210> SEQ ID NO 69
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 69
ggaggagcua cgaugcggcc gauuucguca uccuccauac caucccuua ccguuccgcg     60 ucagacgacu cgcugaggau ccgaca                                         86

<210> SEQ ID NO 70
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 70
ggaggagcua cgaugcggcc gauuucguca uccaccauac caucgccuua ccguuccgcg     60
ucagacgacu cgcugaggau ccgaca                                         86

<210> SEQ ID NO 71
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 71
ggaggagcua cgaugcggcc gucucgcucu caucccgugc acgaaaccuc ucucacugca     60
cagacgacuc gcugaggauc cgaca                                          85

<210> SEQ ID NO 72
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 72
ggaggagcua cgaugcggca acaaacuaau cagacacgag acagagagau agaucugcca     60
gacagacgac ucgcugagga uccgaca                                        87

<210> SEQ ID NO 73
<211> LENGTH: 85
<212> TYPE: DNA
<213> ORGANISM: Artificial Sequence
<220> FEATURE:
<223> OTHER INFORMATION: Synthetic Polynucleotide
```

```
<400> SEQUENCE: 73
ggaggagcua cgaugcggug aauucuuccg gcacuuuguc aucuucaccc cccugcugca    60
cagacgacuc gcugaggauc cgaca                                         85

<210> SEQ ID NO 74
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 74
ggaggagcua cgaugcggcc gauuucguca uccuccauac caucgccuua gcguccgcg    60 ucagacgacu cgcugaggau ccgaca                                        86

<210> SEQ ID NO 75
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 75
ggaggagcua cgaugcggcc gauuucguca uccuccauac cauagccuua ccguccgcg    60 ucagacgacu cgcugaggau ccgaca                                        86

<210> SEQ ID NO 76
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 76
ggaggagcua cgaugcggcc gauuucguca uccuccauac aaucgccuua ccguccgcg    60 ucagacgacu cgcugaggau ccgaca                                        86

<210> SEQ ID NO 77
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 77
ggaggagcua cgaugcggcc caucacuccc gcguacugcg aacgcaucgu uauuuagccg    60
ucagacgacu cgcugaggau ccgaca                                        86

<210> SEQ ID NO 78
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 78
ggaggagcua cgaugcggcc gauuucguca uccuccauac caucgccuua ccgauccgcg    60
ucagacgacu cgcugaggau ccgaca                                        86

<210> SEQ ID NO 79
```

```
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 79
ggaggagcua cgaugcggcc gaauucguca uccuccauac caucgccuua ccguuccgcg      60
ucagacgacu cgcugaggau ccgaca                                          86

<210> SEQ ID NO 80
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 80
ggaggagcua cgaugcggcc gauuucguca uccuccauac caucgacuua ccguuccgcg      60
ucagacgacu cgcugaggau ccgaca                                          86

<210> SEQ ID NO 81
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 81
ggaggagcua cgaugcggcc gauuucguca uccugcauac caucgccuua ccguuccgcg      60
ucagacgacu cgcugaggau ccgaca                                          86

<210> SEQ ID NO 82
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 82
ggaggagcua cgaugcgguc cuuguuuucc ucguacccc acuuccccau uucucccugc       60
ucagacgacu cgcugaggau ccgaca                                          86

<210> SEQ ID NO 83
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 83
ggaggagcua cgaugcggcc gauuucuuca uccuccauac caucgccuua ccguuccgcg      60
ucagacgacu cgcugaggau ccgaca                                          86

<210> SEQ ID NO 84
<211> LENGTH: 86
<212> TYPE: DNA
<213> ORGANISM: Artificial Sequence
<220> FEATURE:
<223> OTHER INFORMATION: Synthetic Polynucleotide
```

<400> SEQUENCE: 84
ggaggagcua cgaugcggcc gauuucguca uccuccauac caucuccuua ccguuccgcg    60
ucagacgacu cgcugaggau ccgaca                                        86

<210> SEQ ID NO 85
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 85
ggaggagcua cgaugcggcc gauuucguca uccuccauac caugccuua ccguuccgcg     60 ucagacgacu cgcugaggau ccgaca                                        86

<210> SEQ ID NO 86
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 86
ggaggagcua cgaugcggcc gauuucggca uccuccauac caucgccuua ccguuccgcg    60
ucagacgacu cgcugaggau ccgaca                                        86

<210> SEQ ID NO 87
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 87
ggaggagcua cgaugcggcc gauuucguga uccuccauac caucgccuua ccguuccgcg    60
ucagacgacu cgcugaggau ccgaca                                        86

<210> SEQ ID NO 88
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 88
ggaggagcua cgaugcggcc gauuucguca uccuccauac caucgccuua ccguaccgcg    60
ucagacgacu cgcugaggau ccgaca                                        86

<210> SEQ ID NO 89
<211> LENGTH: 84
<212> TYPE: DNA
<213> ORGANISM: Artificial Sequence
<220> FEATURE:
<223> OTHER INFORMATION: Synthetic Polynucleotide

<400> SEQUENCE: 89
ggaggagcua cgaugcggac ggaggauagu ugcuaaucga gcccugccga cgcuucagac    60
agacgacucg cugaggaucc gaca                                          84

<210> SEQ ID NO 90

<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 90
ggaggagcua cgaugcggcc gauuucguca uccuccguac caucgccuca ccguuccgcg    60
ucagacgacu cgcugaggau ccgaca                                        86

<210> SEQ ID NO 91
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 91
ggaggagcua cgaugcggcc gauuucguca uccuccauac caucgccuua caguuccgcg    60
ucagacgacu cgcugaggau ccgaca                                        86

<210> SEQ ID NO 92
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 92
ggaggagcua cgaugcggcc gauuucguca uccuccauac caucccuuac cguccgcgu    60 cagacgacuc gcugaggauc cgaca                                         85

<210> SEQ ID NO 93
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 93
ggaggagcua cgaugcggcc gauuucguca uccuccauac caucgccuga ccguuccgcg    60
ucagacgacu cgcugaggau ccgaca                                        86

<210> SEQ ID NO 94
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 94
ggaggagcua cgaugcggcc gauuucguca uccuccauac caucgccuua acguuccgcg    60
ucagacgacu cgcugaggau ccgaca                                        86

<210> SEQ ID NO 95
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 95
ggaggagcua cgaugcggcc gauuucguca uccuccauac caucgccuua ccgguccgcg    60
ucagacgacu cgcugaggau ccgaca    86

<210> SEQ ID NO 96
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 96
ggaggagcua cgaugcggcc gauucgucau ccuccauacc aucgccuuac cguccgcgu    60 cagacgacuc gcugaggauc cgaca    85

<210> SEQ ID NO 97
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 97
ggaggagcua cgaugcggcc gauuucguca uccuccauac caucgccuua ccguccgcgu    60
cagacgacuc gcugaggauc cgaca    85

<210> SEQ ID NO 98
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 98
ggaggagcua cgaugcggug aauucuuccg gcacuuuguc aucuucaccc ccaugcugcg    60
cagacgacuc gcugaggauc cgaca    85

<210> SEQ ID NO 99
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 99
ggaggagcua cgaugcggcc gauucguca uccuccauac caacgccuua ccguccgcg    60 ucagacgacu cgcugaggau ccgaca    86

<210> SEQ ID NO 100
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 100
ggaggagcua cgaugcggcc gauuucguca uccuccauac ccucgccuua ccguccgcg    60 ucagacgacu cgcugaggau ccgaca    86

<210> SEQ ID NO 101

<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 101
ggaggagcua cgaugcggug aauucuuccg gcacuuuguc aucuucaccu ccaugcugca    60
cagacgacuc gcugaggauc cgaca                                         85

<210> SEQ ID NO 102
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 102
ggaggagcua cgaugcggcc gauuucguca uccccauac caucggcuua ccguuccgcg    60
ucagacgacu cgcugaggau ccgaca                                        86

<210> SEQ ID NO 103
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 103
ggaggagcua cgaugcggcc gucucgcucu caucccaugc acgaaaccuc ucucgcugca    60
cagacgacuc gcugaggauc cgaca                                         85

<210> SEQ ID NO 104
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 104
ggaggagcua cgaugcggcc gauuugucau ccuccauacc aucgccuuac cguuccgcgu    60
cagacgacuc gcugaggauc cgaca                                         85

<210> SEQ ID NO 105
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 105
ggaggagcua cgaugcggug aauucuuccg gcacuuuguc aucuucaccc ccacgcugca    60
cagacgacuc gcugaggauc cgaca                                         85

<210> SEQ ID NO 106
<211> LENGTH: 86
<212> TYPE: DNA
<213> ORGANISM: Artificial Sequence
<220> FEATURE:
<223> OTHER INFORMATION: Synthetic Polynucleotide

```
<400> SEQUENCE: 106
ggaggagcua cgaugcggcc gauuacguca uccuccauac caucgccuua ccguuccgcg    60
ucagacgacu cgcugaggau ccgaca                                        86

<210> SEQ ID NO 107
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 107
ggaggagcua cgaugcggcc gauuucgcca uccuccauac caucgccuca ccguuccgcg    60
ucagacgacu cgcugaggau ccgaca                                        86

<210> SEQ ID NO 108
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 108
ggaggagcua cgaugcggcc gauuucgaca uccuccauac caucgccuua ccguuccgcg    60
ucagacgacu cgcugaggau ccgaca                                        86

<210> SEQ ID NO 109
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 109
ggaggagcua cgaugcggcc gauuucguca uccuccauac aucgccuuac cguuccgcgu    60
cagacgacuc gcugaggauc cgaca                                         85

<210> SEQ ID NO 110
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 110
ggaggagcua cgaugcggcc gauuucguca uccuccauac gaucgccuua ccguuccgcg    60
ucagacgacu cgcugaggau ccgaca                                        86

<210> SEQ ID NO 111
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 111
ggaggagcua cgaugcggcc gauuucguca uccuccguac caucgccuua ccauuccgcg    60
ucagacgacu cgcugaggau ccgaca                                        86

<210> SEQ ID NO 112
```

```
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 112
ggaggagcua cgaugcggcc gauuucguca uccccauacc aucgccuuac cguuccgcgu      60
cagacgacuc gcugaggauc cgaca                                           85

<210> SEQ ID NO 113
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 113
ggaggagcua cgaugcggcc gauuucguca uccuccauac cuucgccuua ccguuccgcg      60
ucagacgacu cgcugaggau ccgaca                                          86

<210> SEQ ID NO 114
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 114
ggaggagcua cgaugcggcc gauuucguca ugcuccauac caucgccuua ccguuccgcg      60
ucagacgacu cgcugaggau ccgaca                                          86

<210> SEQ ID NO 115
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 115
ggaggagcua cgaugcggcc caucacuccc gcgcauugcg aacgcaucgu uauuuagccg      60
ucagacgacu cgcugaggau ccgaca                                          86

<210> SEQ ID NO 116
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 116
ggaggagcua cgaugcggcc gauuucguca ucuccauacc aucgccuuac cguuccgcgu      60
cagacgacuc gcugaggauc cgaca                                           85

<210> SEQ ID NO 117
<211> LENGTH: 85
<212> TYPE: DNA
<213> ORGANISM: Artificial Sequence
<220> FEATURE:
<223> OTHER INFORMATION: Synthetic Polynucleotide
```

<400> SEQUENCE: 117
ggaggagcua cgaugcggug aauucuuccg gcacuuuguc aucuucaccc ccaugccgca    60
cagacgacuc gcugaggauc cgaca                                         85

<210> SEQ ID NO 118
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 118
ggaggagcua cgaugcggcc caucacuccc gcguauugcg aacgccucgu uauuuagccg    60
ucagacgacu cgcugaggau ccgaca                                        86

<210> SEQ ID NO 119
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 119
ggaggagcua cgaugcgguc gauuucguca uccuccguac caucgccuua ccguuccgcg    60
ucagacgacu cgcugaggau ccgaca                                        86

<210> SEQ ID NO 120
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 120
ggaggagcua cgaugcggug aauucuuccg gcacuuuguc aucuucaucc ccaugcugca    60
cagacgacuc gcugaggauc cgaca                                         85

<210> SEQ ID NO 121
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 121
ggaggagcua cgaugcggcc gauuucguca uccuccauac caucgccuua ccguuacgcg    60
ucagacgacu cgcugaggau ccgaca                                        86

<210> SEQ ID NO 122
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 122
ggaggagcua cgaugcggcc gauuucguca accuccauac caucgccuua ccguccgcg    60 ucagacgacu cgcugaggau ccgaca                                        86

<210> SEQ ID NO 123

```
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 123
ggaggagcua cgaugcggcc gauuucguca uccgccauac caucgccuua ccguuccgcg    60
ucagacgacu cgcugaggau ccgaca                                         86

<210> SEQ ID NO 124
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 124
ggaggagcua cgaugcggcc gucucgcucu caucccaugc acgaaaccuc ucucccugca    60
cagacgacuc gcugaggauc cgaca                                          85

<210> SEQ ID NO 125
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 125
ggaggagcua cgaugcggcc gauuucguca uccuccacac caucgccuua ccgcuccgcg    60
ucagacgacu cgcugaggau ccgaca                                         86

<210> SEQ ID NO 126
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 126
ggaggagcua cgaugcggcc gauuucguca uccuccauac caucgccuua ccguuccgcu    60
ucagacgacu cgcugaggau ccgaca                                         86

<210> SEQ ID NO 127
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 127
ggaggagcua cgaugcggcc gauuucguca ucgccauac caucgccuua ccguuccgcg    60
ucagacgacu cgcugaggau ccgaca                                         86

<210> SEQ ID NO 128
<211> LENGTH: 86
<212> TYPE: DNA
<213> ORGANISM: Artificial Sequence
<220> FEATURE:
<223> OTHER INFORMATION: Synthetic Polynucleotide
```

<400> SEQUENCE: 128
ggaggagcua cgaugcggcc gauuucguca uccuccauac caucgccgua ccguuccgcg    60
ucagacgacu cgcugaggau ccgaca                                        86

<210> SEQ ID NO 129
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 129
ggaggagcua cgaugcggcc gauuucguca uccuccauac caucgccuua ccguugcgcg    60
ucagacgacu cgcugaggau ccgaca                                        86

<210> SEQ ID NO 130
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 130
ggaggagcua cgaugcggcc gaugucguca uccuccauac caucgccuua ccguccgcg     60 ucagacgacu cgcugaggau ccgaca                                        86

<210> SEQ ID NO 131
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 131
ggaggagcua cgaugcggcc gauaucguca uccuccauac caucgccuuc cguccgcgu    60 cagacgacuc gcugaggauc cgaca                                         85

<210> SEQ ID NO 132
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 132
ggaggagcua cgaugcggcc gauuucguca uccuccauac caucgccuua ccgucgcgu    60 cagacgacuc gcugaggauc cgaca                                         85

<210> SEQ ID NO 133
<211> LENGTH: 84
<212> TYPE: DNA
<213> ORGANISM: Artificial Sequence
<220> FEATURE:
<223> OTHER INFORMATION: Synthetic Polynucleotide

<400> SEQUENCE: 133
ggaggagcua cgaugcggug aauucuuccg gcacuuuguc aucuucaccc caugcugcac    60
agacgacucg cugaggaucc gaca                                          84

<210> SEQ ID NO 134

<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 134
ggaggagcua cgaugcggug aauucuuccg gcacuuuguc aucuucgccc ccaugcugca    60
cagacgacuc gcugaggauc cgaca                                         85

<210> SEQ ID NO 135
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 135
ggaggagcua cgaugcggca ggugcgggau cuaaugcgua gacagccaua uacugacaca    60
gacagacgac ucgcugagga uccgaca                                       87

<210> SEQ ID NO 136
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 136
ggaggagcua cgaugcggcc gucucgcucu caucccaugc acgaacccuc ucucacugca    60
cagacgacuc gcugaggauc cgaca                                         85

<210> SEQ ID NO 137
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 137
ggaggagcua cgaugcggcc gauugcguca uccuccauac caucgccuua ccguccgcg    60 ucagacgacu cgcugaggau ccgaca                                        86

<210> SEQ ID NO 138
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 138
ggaggagcua cgaugcggug aauucuuccg gcacuuuguc aucuucaccc ccaugcugcu    60
cagacgacuc gcugaggauc cgaca                                         85

<210> SEQ ID NO 139
<211> LENGTH: 85
<212> TYPE: DNA
<213> ORGANISM: Artificial Sequence
<220> FEATURE:
<223> OTHER INFORMATION: Synthetic Polynucleotide -continued

<400> SEQUENCE: 139
ggaggagcua cgaugcggcc gucucgcucu caucccaugc acgaaaccuc ucucacugcg    60
cagacgacuc gcugaggauc cgaca    85

<210> SEQ ID NO 140
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 140
ggaggagcua cgaugcggac ggaaggauag uugcuaaucg agcccugccg acgcuucaga    60
cagacgacuc gcugaggauc cgaca    85

<210> SEQ ID NO 141
<211> LENGTH: 88
<212> TYPE: DNA
<213> ORGANISM: Artificial Sequence
<220> FEATURE:
<223> OTHER INFORMATION: Synthetic Polynucleotide

<400> SEQUENCE: 141
ggaggagcua cgaugcggca aaaacugaua aacacagguc cggcauuuga gcguacaccc    60
agacagacga cucgcugagg auccgaca    88

<210> SEQ ID NO 142
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 142
ggaggagcua cgaugcggug aauucuuccg gcacuuuguc aucuucaccc ccgugcugca    60
cagacgacuc gcugaggauc cgaca    85

<210> SEQ ID NO 143
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 143
ggaggagcua cgaugcggcc gauuucguca uccuccauac cucgccuuac cguccgcgu    60 cagacgacuc gcugaggauc cgaca    85

<210> SEQ ID NO 144
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 144
ggaggagcua cgaugcggcc gauuucguca uccuccauac caucgccuua ccguccgcc    60 ucagacgacu cgcugaggau ccgaca    86

<210> SEQ ID NO 145

```
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 145
ggaggagcua cgaugcggcc caucacuccc gcguguugcg aacgcaucgu uauuuagccg    60
ucagacgacu cgcugaggau ccgaca                                        86

<210> SEQ ID NO 146
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 146
ggaggagcua cgaugcggcu ucccuauucc aaaggaggug cgguacguuu uguuacgcca    60
gacagacgac ucgcugagga uccgaca                                       87

<210> SEQ ID NO 147
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 147
ggaggagcua cgaugcggcc gauuucguca uccuccauac uaucgcccua ccguccgcg    60 ucagacgacu cgcugaggau ccgaca                                        86

<210> SEQ ID NO 148
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 148
ggaggagcua cgaugcggcc gauuucguca uccuccacac caucgccuua ccguccgca    60 ucagacgacu cgcugaggau ccgaca                                        86

<210> SEQ ID NO 149
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 149
ggaggagcua cgaugcggcc gauuucguca uccuccauac caucgccuua ccgugccgcg    60
ucagacgacu cgcugaggau ccgaca                                        86

<210> SEQ ID NO 150
<211> LENGTH: 85
<212> TYPE: DNA
<213> ORGANISM: Artificial Sequence
<220> FEATURE:
<223> OTHER INFORMATION: Synthetic Polynucleotide
```

<400> SEQUENCE: 150
ggaggagcua cgaugcggug aauucuuccg gcaccuuguc aucuucaccc ccaugcugca    60
cagacgacuc gcugaggauc cgaca    85

<210> SEQ ID NO 151
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 151
ggaggagcua cgaugcggug uacccugauu gccuuugugu uaugagcgac agaucugcca    60
gacagacgac ucgcugagga uccgaca    87

<210> SEQ ID NO 152
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 152
ggaggagcua cgaugcggcc caccacuccc gcguauugcg aacgcaucgu uauuuagccg    60
ucagacgacu cgcugaggau ccgaca    86

<210> SEQ ID NO 153
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 153
ggaggagcua cgaugcggug aauucuuccg gcacuuuguc gucuucaccc ccaugcugca    60
cagacgacuc gcugaggauc cgaca    85

<210> SEQ ID NO 154
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 154
ggaggagcua cgaugcggua cacucaguca cguagcaccg cagugacccu uuguaccgca    60
gacagacgac ucgcugagga uccgaca    87

<210> SEQ ID NO 155
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 155
ggaggagcua cgaugcggcc agccacacuu ugaccgaauu ggcaagcgcg ggcaaaucga    60
acagacgacu cgcugaggau ccgaca    86

<210> SEQ ID NO 156

```
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 156
ggaggagcua cgaugcggcc gucucgcucu caucccaugc acgacaccuc ucucacugca     60
cagacgacuc gcugaggauc cgaca                                          85

<210> SEQ ID NO 157
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 157
ggaggagcua cgaugcgguc gucucgcucu caucccaugc acgaaaccuc ucucacugca     60
cagacgacuc gcugaggauc cgaca                                          85

<210> SEQ ID NO 158
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 158
ggaggagcua cgaugcggcc gauuucguca uccuccauac caugccuuac cguuccgcgu     60
cagacgacuc gcugaggauc cgaca                                          85

<210> SEQ ID NO 159
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 159
ggaggagcua cgaugcggcc gucucgcucu ccucccaugc acgaaaccuc ucucacugca     60
cagacgacuc gcugaggauc cgaca                                          85

<210> SEQ ID NO 160
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 160
ggaggagcua cgaugcgggc ugugccggcc cugcucuggu cgccauuguc agucugugca     60
gacagacgac ucgcugagga uccgaca                                        87

<210> SEQ ID NO 161
<211> LENGTH: 85
<212> TYPE: DNA
<213> ORGANISM: Artificial Sequence
<220> FEATURE:
<223> OTHER INFORMATION: Synthetic Polynucleotide
```

```
<400> SEQUENCE: 161
ggaggagcua cgaugcggug aauucucccg gcacuuuguc aucuucaccc ccaugcugca    60
cagacgacuc gcugaggauc cgaca                                         85

<210> SEQ ID NO 162
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 162
ggaggagcua cgaugcggac cuuguuuuuc cucuguaccc cacuuccca uuucucccug    60 cucagacgac ucgcugagga uccgaca                                       87

<210> SEQ ID NO 163
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 163
ggaggagcua cgaugcggau uauuguuuga cguauuccaa gugagauuac gcacgcacca    60
gacagacgac ucgcugagga uccgaca                                       87

<210> SEQ ID NO 164
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 164
ggaggagcua cgaugcggcc gauaucguca uccuccauac caucgccuua ccgucccgcg    60
ucagacgacu cgcugaggau ccgaca                                        86

<210> SEQ ID NO 165
<211> LENGTH: 84
<212> TYPE: DNA
<213> ORGANISM: Artificial Sequence
<220> FEATURE:
<223> OTHER INFORMATION: Synthetic Polynucleotide

<400> SEQUENCE: 165
ggaggagcua cgaugcggug aauucuuccg gcacuuuguc aucuucccc caugcugcac    60 agacgacucg cugaggaucc gaca                                          84

<210> SEQ ID NO 166
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 166
ggaggagcua cgaugcggcc gucucgcucu uaucccaugc acgaaaccuc ucucacugca    60
cagacgacuc gcugaggauc cgaca                                         85

<210> SEQ ID NO 167
```

-continued

```
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 167
ggaggagcua cgaugcggug aauucuuccg gcacuuuguc aucuucaccc ucaugcugca    60
cagacgacuc gcugaggauc cgaca                                         85

<210> SEQ ID NO 168
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 168
ggaggagcua cgaugcggcc caucacuccc gcguauugcg aacgcaucgu uguuuagccg    60
ucagacgacu cgcugaggau ccgaca                                        86

<210> SEQ ID NO 169
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 169
ggaggagcua cgaugcggug aauucuuccg gcacuuuguc auccucaccc ccaugcugca    60
cagacgacuc gcugaggauc cgaca                                         85

<210> SEQ ID NO 170
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 170
ggaggagcua cgaugcggcc caucacuccc acguauugcg aacgcaucgu uauuuagccg    60
ucagacgacu cgcugaggau ccgaca                                        86

<210> SEQ ID NO 171
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 171
ggaggagcua cgaugcggcc gauuucguca ucuccauac caucgccuua ccguuuccgc    60
gucagacgac ucgcugagga uccgaca                                       87

<210> SEQ ID NO 172
<211> LENGTH: 87
<212> TYPE: DNA
<213> ORGANISM: Artificial Sequence
<220> FEATURE:
<223> OTHER INFORMATION: Synthetic Polynucleotide
```

<400> SEQUENCE: 172
ggaggagcua cgaugcgggg aagcaacacu uagucgggau ugauacgugc ccagucagca    60
gucagacgac ucgcugagga uccgaca                                        87

<210> SEQ ID NO 173
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 173
ggaggagcua cgaugcggcc gaucacuccc gcguauugcg aacgcaucgu uauuuagccg    60
ucagacgacu cgcugaggau ccgaca                                         86

<210> SEQ ID NO 174
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 174
ggaggagcua cgaugcggcc gaauuucguc auccuccaua ccaucgccuu accguuccgc    60
gucagacgac ucgcugagga uccgaca                                        87

<210> SEQ ID NO 175
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 175
ggaggagcua cgaugcggcc gauuucguca uccuccauac caucgcuuac cguccgcgu    60 cagacgacuc gcugaggauc cgaca                                          85

<210> SEQ ID NO 176
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 176
ggaggagcua cgaugcggcc gauuucguca uccuccauac caucgcccac cguccgcgu    60 cagacgacuc gcugaggauc cgaca                                          85

<210> SEQ ID NO 177
<211> LENGTH: 84
<212> TYPE: DNA
<213> ORGANISM: Artificial Sequence
<220> FEATURE:
<223> OTHER INFORMATION: Synthetic Polynucleotide

<400> SEQUENCE: 177
ggaggagcua cgaugcggcc gauuucguca uccuccauac caucgccuua ccguccguc    60 agacgacucg cugaggaucc gaca                                           84

<210> SEQ ID NO 178

```
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 178
ggaggagcua cgaugcgggg aagcaccacu uagucgcgau ugauacgugc gcagucauca      60
gacagacgac ucgcugagga uccgaca                                         87

<210> SEQ ID NO 179
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 179
ggaggagcua cgaugcggug aauucuuccg gcacuuuguc aucuuacgc ccaugcugca       60 cagacgacuc gcugaggauc cgaca                                           85

<210> SEQ ID NO 180
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 180
ggaggagcua cgaugcggcc gauuucguca uccuccaagc caucgccuua ccguccgcg      60 ucagacgacu cgcugaggau ccgaca                                          86

<210> SEQ ID NO 181
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 181
ggaggagcua cgaugcggug aauucuuccg acacuuuguc aucuuacccc ccaugcugca     60
cagacgacuc gcugaggauc cgaca                                           85

<210> SEQ ID NO 182
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 182
ggaggagcua cgaugcgggg aagccacacu uagucgcgau ugauacgugc gcagucauca    60
gacagacgac ucgcugagga uccgaca                                         87

<210> SEQ ID NO 183
<211> LENGTH: 85
<212> TYPE: DNA
<213> ORGANISM: Artificial Sequence
<220> FEATURE:
<223> OTHER INFORMATION: Synthetic Polynucleotide
```

-continued

<400> SEQUENCE: 183
ggaggagcua cgaugcggcc gucucguucu caucccaugc acgaaaccuc ucucacugca    60
cagacgacuc gcugaggauc cgaca                                         85

<210> SEQ ID NO 184
<211> LENGTH: 84
<212> TYPE: DNA
<213> ORGANISM: Artificial Sequence
<220> FEATURE:
<223> OTHER INFORMATION: Synthetic Polynucleotide

<400> SEQUENCE: 184
ggaggagcua cgaugcggac ggaggauagu ugcuaaucga gcccugccga cgcuucaguc    60
agacgacucg cugaggaucc gaca                                          84

<210> SEQ ID NO 185
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 185
ggaggagcua cgaugcggac gguuucaccu cuaggagcac ugaaagccaa ccuucgcgca    60
cagacgacuc gcugaggauc cgaca                                         85

<210> SEQ ID NO 186
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 186
ggaggagcua cgaugcggug aauuccuccg gcacuuuguc aucuucaccc ccaugcugca    60
cagacgacuc gcugaggauc cgaca                                         85

<210> SEQ ID NO 187
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 187
ggaggagcua cgaugcggcc gauuucguca uccuccacau caucgccuua ccguccgcg    60 ucagacgacu cgcugaggau ccgaca                                        86

<210> SEQ ID NO 188
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 188
ggaggagcua cgaugcggcc gauuucguca uccccauac caucgccuua ccuuccgcgu    60
cagacgacuc gcugaggauc cgaca                                         85

<210> SEQ ID NO 189

```
<211> LENGTH: 84
<212> TYPE: DNA
<213> ORGANISM: Artificial Sequence
<220> FEATURE:
<223> OTHER INFORMATION: Synthetic Polynucleotide

<400> SEQUENCE: 189
ggaggagcua cgaugcggug aauucuuccg gcacuuguca ucuucacccc caugcugcac     60
agacgacucg cugaggaucc gaca                                          84

<210> SEQ ID NO 190
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 190
ggaggagcua cgaugcggcc gucucgcucu caucccaugc gcgaaaccuc ucucacugca     60
cagacgacuc gcugaggauc cgaca                                         85

<210> SEQ ID NO 191
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 191
ggaggagcua cgaugcggug aauucuuccg gcacuuuguc aucuucaccc cuaugcugca     60
cagacgacuc gcugaggauc cgaca                                         85

<210> SEQ ID NO 192
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 192
ggaggagcua cgaugcggcc gauuuucguc auccuccaua ccaucgcccu accguuccgc     60
gucagacgac ucgcugagga uccgaca                                       87

<210> SEQ ID NO 193
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 193
ggaggagcua cgaugcggcc caucacuccc gcguauugcg aacgcaucgu uauuuagcug     60
ucagacgacu cgcugaggau ccgaca                                        86

<210> SEQ ID NO 194
<211> LENGTH: 86
<212> TYPE: DNA
<213> ORGANISM: Artificial Sequence
<220> FEATURE:
<223> OTHER INFORMATION: Synthetic Polynucleotide
```

```
<400> SEQUENCE: 194
ggaggagcua cgaugcggcc caucgcuccc gcguauugcg aacgcaucgu uauuuagccg    60
ucagacgacu cgcugaggau ccgaca                                        86

<210> SEQ ID NO 195
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 195
ggaggagcua cgaugcggcc gauuucggca uccuccacac caucgccuua ccguccgcg    60 ucagacgacu cgcugaggau ccgaca                                        86

<210> SEQ ID NO 196
<211> LENGTH: 84
<212> TYPE: DNA
<213> ORGANISM: Artificial Sequence
<220> FEATURE:
<223> OTHER INFORMATION: Synthetic Polynucleotide

<400> SEQUENCE: 196
ggaggagcua cgaugcggcc gauuucguca uccccauca ucgccuuacc guccgcguc     60 agacgacucg cugaggaucc gaca                                          84

<210> SEQ ID NO 197
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 197
ggaggagcua cgaugcggug aacucuuccg gcacuuuguc aucuucaccc ccaugcugca    60
cagacgacuc gcugaggauc cgaca                                         85

<210> SEQ ID NO 198
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 198
ggaggagcua cgaugcggcc caucacuccc gcguauugcg aacgcaucgu uauucagccg    60
ucagacgacu cgcugaggau ccgaca                                        86

<210> SEQ ID NO 199
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 199
ggaggagcua cgaugcggcc gucucgcucu caucccaugc acaaaaccuc ucucacugca    60
cagacgacuc gcugaggauc cgaca                                         85

<210> SEQ ID NO 200
```

<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 200
ggaggagcua cgaugcggcc gauuucguca uccccauac caucgccuua ccguuccgca    60
gucagacgac ucgcugagga uccgaca                                       87

<210> SEQ ID NO 201
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 201
ggaggagcua cgaugcggcc gauuucguca ucuccacac caucgccuua cuguuccgcg    60
ucagacgacu cgcugaggau ccgaca                                        86

<210> SEQ ID NO 202
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 202
ggaggagcua cgaugcggcc gucucgcucu caucccaugc acgaaaucuc ucucacugca    60
cagacgacuc gcugaggauc cgaca                                         85

<210> SEQ ID NO 203
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 203
ggaggagcua cgaugcggcc caucacuccc gcguauugcg aacgcaucgc uauuuagccg    60
ucagacgacu cgcugaggau ccgaca                                        86

<210> SEQ ID NO 204
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 204
ggaggagcua cgaugcggcc gauuucguca uccucauacc aucgccuuac cguuccgcgu    60
cagacgacuc gcugaggauc cgaca                                         85

<210> SEQ ID NO 205
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 205
ggaggagcua cgaugcggac cuuguuccc ucguacccc acuuccccau uucucccugc    60
ucagacgacu cgcugaggau ccgaca                                       86

<210> SEQ ID NO 206
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 206
ggaggagcua cgaugcggug aauucuuccg gcacuuuguc aucuccaccc ccaugcugca    60
cagacgacuc gcugaggauc cgaca                                          85

<210> SEQ ID NO 207
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 207
ggaggagcua cgaugcgguc gauuucguca uccuccauac caucgccuua cuguuccgcg    60
ucagacgacu cgcugaggau ccgaca                                          86

<210> SEQ ID NO 208
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 208
ggaggagcua cgaugcggcc gauuucguca uccuccauac caucgucuua ccuuccgcg    60 ucagacgacu cgcugaggau ccgaca                                          86

<210> SEQ ID NO 209
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 209
ggaggagcua cgaugcggcc gauuucguca uccuccauac caucgccuua cguccgcgu    60 cagacgacuc gcugaggauc cgaca                                          85

<210> SEQ ID NO 210
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 210
ggaggagcua cgaugcggcc gauuucguca uccuccauac caucgccuua ccacuccgcg    60
ucagacgacu cgcugaggau ccgaca                                          86

<210> SEQ ID NO 211

```
<211> LENGTH: 84
<212> TYPE: DNA
<213> ORGANISM: Artificial Sequence
<220> FEATURE:
<223> OTHER INFORMATION: Synthetic Polynucleotide

<400> SEQUENCE: 211
ggaggagcua cgaugcggac ggaggauagu ugcuaaucga gcccugcuga cgcuucagac      60
agacgacucg cugaggaucc gaca                                            84

<210> SEQ ID NO 212
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 212
ggaggagcua cgaugcggug uacacugauu gccuuugugu uaugggcgac agaucugcca      60
gacagacgac ucgcugagga uccgaca                                         87

<210> SEQ ID NO 213
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 213
ggaggagcua cgaugcggug aauccuuccg gcacuuuguc aucuucaccc ccaugcugca      60
cagacgacuc gcugaggauc cgaca                                           85

<210> SEQ ID NO 214
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 214
ggaggagcua cgaugcggug aauucuuccg gcacuuugcc aucuucaccc ccaugcugca      60
cagacgacuc gcugaggauc cgaca                                           85

<210> SEQ ID NO 215
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 215
ggaggagcua cgaugcggac cucguuuucc ucguaccccc acuuccccau uucucccugc      60
ucagacgacu cgcugaggau ccgaca                                          86

<210> SEQ ID NO 216
<211> LENGTH: 85
<212> TYPE: DNA
<213> ORGANISM: Artificial Sequence
<220> FEATURE:
<223> OTHER INFORMATION: Synthetic Polynucleotide
```

-continued

<400> SEQUENCE: 216
ggaggagcua cgaugcggcc gucucgcucu caucccaugc acgaaaccuc ucuaacugca    60
cagacgacuc gcugaggauc cgaca                                         85

<210> SEQ ID NO 217
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 217
ggaggagcua cgaugcggcc gucucgcucu caucccaugc acgaaaccuc ccucacugca    60
cagacgacuc gcugaggauc cgaca                                         85

<210> SEQ ID NO 218
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 218
ggaggagcua cgaugcggcc gucucgcucu caucccaugc acgaaaccuc ucucaccgca    60
cagacgacuc gcugaggauc cgaca                                         85

<210> SEQ ID NO 219
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 219
ggaggagcua cgaugcggcc caucacuccc gcguaucgcg aacgcaucgu uauuuagccg    60
ucagacgacu cgcugaggau ccgaca                                        86

<210> SEQ ID NO 220
<211> LENGTH: 88
<212> TYPE: DNA
<213> ORGANISM: Artificial Sequence
<220> FEATURE:
<223> OTHER INFORMATION: Synthetic Polynucleotide

<400> SEQUENCE: 220
ggaggagcua cgaugcggcc gauuuucgu cauccuccau accaucgccu uaccguuccg     60
cgucagacga cucgcugagg auccgaca                                      88

<210> SEQ ID NO 221
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 221
ggaggagcua cgaugcggcc gucucgcucu caucccaugc acgaaacccc ucucacugca    60
cagacgacuc gcugaggauc cgaca                                         85

<210> SEQ ID NO 222

```
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 222
ggaggagcua cgaugcggca gauuucguca ucauccauac caucgccuua ccguuccgcg      60
ucagacgacu cgcugaggau ccgaca                                          86

<210> SEQ ID NO 223
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 223
ggaggagcua cgaugcggcc caucacuccc gcgcacugcg aacgcaucgu uauuuagccg      60
ucagacgacu cgcugaggau ccgaca                                          86

<210> SEQ ID NO 224
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 224
ggaggagcua cgaugcggcc caucccuccc gcguauugcg aacgccucgu uauuuagccg      60
ucagacgacu cgcugaggau ccgaca                                          86

<210> SEQ ID NO 225
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 225
ggaggagcua cgaugcggaa ucucccgaac gcauuaguca gucccauacc cgugugccgc      60
gucagacgac ucgcugagga uccgaca                                         87

<210> SEQ ID NO 226
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 226
ggaggagcua cgaugcggcc caucacuccc guguauugcg aacgcaucgu uauuuagccg      60
ucagacgacu cgcugaggau ccgaca                                          86

<210> SEQ ID NO 227
<211> LENGTH: 85
<212> TYPE: DNA
<213> ORGANISM: Artificial Sequence
<220> FEATURE:
<223> OTHER INFORMATION: Synthetic Polynucleotide
```

<400> SEQUENCE: 227
ggaggagcua cgaugcggcc gauuucguca uccuccaacc aucgccuuac cguuccgcgu    60
cagacgacuc gcugaggauc cgaca                                         85

<210> SEQ ID NO 228
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 228
ggaggagcua cgaugcggcc caucacuccc gcguauugcg aacgcaucgu uaucuagccg    60
ucagacgacu cgcugaggau ccgaca                                        86

<210> SEQ ID NO 229
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 229
ggaggagcua cgaugcggac gauuucguca uccuccauac caucgccuua ccguuccgag    60
ucagacgacu cgcugaggau ccgaca                                        86

<210> SEQ ID NO 230
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 230
ggaggagcua cgaugcggcc caucacuccc gcguauugcg aacguaucgu uauuuagccg    60
ucagacgacu cgcugaggau ccgaca                                        86

<210> SEQ ID NO 231
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 231
ggaggagcua cgaugcggau uaccaacuug aacgccgaga guguggucau guguucugca    60
gacagacgac ucgcugagga uccgaca                                       87

<210> SEQ ID NO 232
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 232
ggaggagcua cgaugcggcc gauuuucguc auccuccaug ccaucgccuu accguuccgc    60
gucagacgac ucgcugagga uccgaca                                       87

<210> SEQ ID NO 233

<210> SEQ ID NO 233
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 233
ggaggagcua cgaugcggug gauucuuccg gcacuuuguc aucuucaccc ccaugcugca    60
cagacgacuc gcugaggauc cgaca                                         85

<210> SEQ ID NO 234
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 234
ggaggagcua cgaugcggcc gauuucguca uccuccacac caucgccuua cccuuccgcg    60
ucagacgacu cgcugaggau ccgaca                                        86

<210> SEQ ID NO 235
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 235
ggaggagcua cgaugcggcc gauuucguca uccuccauac caucgucuua ccguucugcg    60
ucagacgacu cgcugaggau ccgaca                                        86

<210> SEQ ID NO 236
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 236
ggaggagcua cgaugcggug aauucuuccg gcacuuuguc aucuucaccc cccaugcugc    60
acagacgacu cgcugaggau ccgaca                                        86

<210> SEQ ID NO 237
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 237
ggaggagcua cgaugcggac cuuguuuucc ucuguacccc acuucccauu ucucccugcu    60
cagacgacuc gcugaggauc cgaca                                         85

<210> SEQ ID NO 238
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 238
ggaggagcua cgaugcggcc caucacuccc gcguauugcg agcgcaucgu uauuuagccg     60
ucagacgacu cgcugaggau ccgaca                                         86

<210> SEQ ID NO 239
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 239
ggaggagcua cgaugcggcc gauuucguca uccuccauac caucgccuua ccguccgag     60 acagacgacu cgcugaggau ccgaca                                         86

<210> SEQ ID NO 240
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 240
ggaggagcua cgaugcggcc caucacuccc gcgaauugcg aacgcaucgu uauuuagccg     60
ucagacgacu cgcugaggau ccgaca                                         86

<210> SEQ ID NO 241
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 241
ggaggagcua cgaugcggcc gucucgcucc caucccaugc acgaaaccuc ucucacugca     60
cagacgacuc gcugaggauc cgaca                                          85

<210> SEQ ID NO 242
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 242
ggaggagcua cgaugcggcc caucacuccc gcguauugcg aacgcaucgu uauuagccgu     60
cagacgacuc gcugaggauc cgaca                                          85

<210> SEQ ID NO 243
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 243
ggaggagcua cgaugcggac cuuguuuucc uccguacccc acuuccccau uucucccugc     60
ucagacgacu cgcugaggau ccgaca                                         86

<210> SEQ ID NO 244

```
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 244
ggaggagcua cgaugcggcu gauuucguca uccccauac caucgccuua ccguuccgcg    60
ucagacgacu cgcugaggau ccgaca                                       86

<210> SEQ ID NO 245
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 245
ggaggagcua cgaugcggug aauucuuccg gcacuuuguc aucuucaccc ccaugcggca    60
cagacgacuc gcugaggauc cgaca                                        85

<210> SEQ ID NO 246
<211> LENGTH: 84
<212> TYPE: DNA
<213> ORGANISM: Artificial Sequence
<220> FEATURE:
<223> OTHER INFORMATION: Synthetic Polynucleotide

<400> SEQUENCE: 246
ggaggagcua cgaugcggac ggaggauagu ugcuaaucga gcccugcgga cgcuucagac    60
agacgacucg cugaggaucc gaca                                         84

<210> SEQ ID NO 247
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 247
ggaggagcua cgaugcggug aauucuuccg gcacuuuguc aucuucaccc ccaggcugca    60
cagacgacuc gcugaggauc cgaca                                        85

<210> SEQ ID NO 248
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 248
ggaggagcua cgaugcggcc gauuucguau ccuccguacc aucgccuuac cguuccgcgu    60
cagacgacuc gcugaggauc cgaca                                        85

<210> SEQ ID NO 249
<211> LENGTH: 85
<212> TYPE: DNA
<213> ORGANISM: Artificial Sequence
<220> FEATURE:
<223> OTHER INFORMATION: Synthetic Polynucleotide
```

<400> SEQUENCE: 249
ggaggagcua cgaugcggcc gucucgaucu caucccaugc acgaaaccuc ucucacugca    60
cagacgacuc gcugaggauc cgaca    85

<210> SEQ ID NO 250
<211> LENGTH: 84
<212> TYPE: DNA
<213> ORGANISM: Artificial Sequence
<220> FEATURE:
<223> OTHER INFORMATION: Synthetic Polynucleotide

<400> SEQUENCE: 250
ggaggagcua cgaugcggcc gauuucguca uccuccauac caucgccucc guuccgcguc    60
agacgacucg cugaggaucc gaca    84

<210> SEQ ID NO 251
<211> LENGTH: 82
<212> TYPE: DNA
<213> ORGANISM: Artificial Sequence
<220> FEATURE:
<223> OTHER INFORMATION: Synthetic Polynucleotide

<400> SEQUENCE: 251
ggaggacgau gcggccgauu ucgucauccu ccauaccauc gccuuaccgu uccgcgucag    60
acgacucgcu gaggauccga ga    82

<210> SEQ ID NO 252
<211> LENGTH: 81
<212> TYPE: DNA
<213> ORGANISM: Artificial Sequence
<220> FEATURE:
<223> OTHER INFORMATION: Synthetic Polynucleotide

<400> SEQUENCE: 252
ggaggacgau gcggugaauu cuccggcac uuugucaucu ucaccccau gcugcacaga    60 cgacucgcug aggauccgag a    81

<210> SEQ ID NO 253
<211> LENGTH: 81
<212> TYPE: DNA
<213> ORGANISM: Artificial Sequence
<220> FEATURE:
<223> OTHER INFORMATION: Synthetic Polynucleotide

<400> SEQUENCE: 253
ggaggacgau gcggccgucu cgcucucauc ccaugcacga aaccucucuc acugcacaga    60
cgacucgcug aggauccgag a    81

<210> SEQ ID NO 254
<211> LENGTH: 82
<212> TYPE: DNA
<213> ORGANISM: Artificial Sequence
<220> FEATURE:
<223> OTHER INFORMATION: Synthetic Polynucleotide

<400> SEQUENCE: 254
ggaggacgau gcggcccauc acucccgcgu auugcgaacg caucguuauu uagccgucag    60
acgacucgcu gaggauccga ga    82

<210> SEQ ID NO 255

<211> LENGTH: 82
<212> TYPE: DNA
<213> ORGANISM: Artificial Sequence
<220> FEATURE:
<223> OTHER INFORMATION: Synthetic Polynucleotide

<400> SEQUENCE: 255
ggaggacgau gcggaccuug uuuccucug uacccacuu ccccauuucu cccugcucag    60
acgacucgcu gaggauccga ga                                           82

<210> SEQ ID NO 256
<211> LENGTH: 79
<212> TYPE: DNA
<213> ORGANISM: Artificial Sequence
<220> FEATURE:
<223> OTHER INFORMATION: Synthetic Polynucleotide

<400> SEQUENCE: 256
ggaggacgau gcguguaca cugauugccu uguguuaug agcgacagau cugccagacg    60
acucgcugag gauccgaga                                               79

<210> SEQ ID NO 257
<211> LENGTH: 79
<212> TYPE: DNA
<213> ORGANISM: Artificial Sequence
<220> FEATURE:
<223> OTHER INFORMATION: Synthetic Polynucleotide

<400> SEQUENCE: 257
ggaggacgau gcggggaagc aacacuuagu cgcgauugau acgugcgcag ucaucagacg    60
acucgcugag gauccgaga                                               79

<210> SEQ ID NO 258
<211> LENGTH: 79
<212> TYPE: DNA
<213> ORGANISM: Artificial Sequence
<220> FEATURE:
<223> OTHER INFORMATION: Synthetic Polynucleotide

<400> SEQUENCE: 258
ggaggacgau gcggccgauu uucgucaucc uccauaccau cgccuuaccg uucccagacg    60
acucgcugag gauccgaga                                               79

<210> SEQ ID NO 259
<211> LENGTH: 79
<212> TYPE: DNA
<213> ORGANISM: Artificial Sequence
<220> FEATURE:
<223> OTHER INFORMATION: Synthetic Polynucleotide

<400> SEQUENCE: 259
ggaggacgau gcgguaauuc ucaggaggug cggaacggga uauggauugu ucgccagacg    60
acucgcugag gauccgaga                                               79

<210> SEQ ID NO 260
<211> LENGTH: 79
<212> TYPE: DNA
<213> ORGANISM: Artificial Sequence
<220> FEATURE:
<223> OTHER INFORMATION: Synthetic Polynucleotide

<400> SEQUENCE: 260
ggaggacgau gcgguacacu cagucacgua gcaccgcagu gacccuuugu accgcagacg    60
acucgcugag gauccgaga    79

<210> SEQ ID NO 261
<211> LENGTH: 79
<212> TYPE: DNA
<213> ORGANISM: Artificial Sequence
<220> FEATURE:
<223> OTHER INFORMATION: Synthetic Polynucleotide

<400> SEQUENCE: 261
ggaggacgau gcggccuagu acaaaagccu gaucucugug agcagacacu agaacagacg    60
acucgcugag gauccgaga    79

<210> SEQ ID NO 262
<211> LENGTH: 79
<212> TYPE: DNA
<213> ORGANISM: Artificial Sequence
<220> FEATURE:
<223> OTHER INFORMATION: Synthetic Polynucleotide

<400> SEQUENCE: 262
ggaggacgau gcggauuacc aacuugaacg ccgagagugu ggucacgugu ucugcagacg    60
acucgcugag gauccgaga    79

<210> SEQ ID NO 263
<211> LENGTH: 79
<212> TYPE: DNA
<213> ORGANISM: Artificial Sequence
<220> FEATURE:
<223> OTHER INFORMATION: Synthetic Polynucleotide

<400> SEQUENCE: 263
ggaggacgau gcggggaagc aacacuuagu cgcgauugau acgugcgcag ucaucagacg    60
acucgcugag gauccgaga    79

<210> SEQ ID NO 264
<211> LENGTH: 79
<212> TYPE: DNA
<213> ORGANISM: Artificial Sequence
<220> FEATURE:
<223> OTHER INFORMATION: Synthetic Polynucleotide

<400> SEQUENCE: 264
ggaggacgau gcggcaacaa acuaaucaga cacgagacag agagauagau cugccagacg    60
acucgcugag gauccgaga    79

<210> SEQ ID NO 265
<211> LENGTH: 79
<212> TYPE: DNA
<213> ORGANISM: Artificial Sequence
<220> FEATURE:
<223> OTHER INFORMATION: Synthetic Polynucleotide

<400> SEQUENCE: 265
ggaggacgau gcggcaggug cgggaucuaa ugcguagaca gccauauacu gacacagacg    60
acucgcugag gauccgaga    79

<210> SEQ ID NO 266

```
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 266
ggaggagcua cgaugcggca ggugcggggu cuaaugcgua gacagccaua uacugacaca    60
gacagacgac ucgcugagga uccgaca                                       87

<210> SEQ ID NO 267
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 267
ggaggagcua cgaugcggca ggggcggggu cuaaugcgua gacagccaua uacugacaca    60
gacagacgac ucgcugagga uccgaca                                       87

<210> SEQ ID NO 268
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 268
ggaggagcua cgaugcgggg aagcaacacu uagucgcgau ugaugcgugc gcagucauca    60
gacagacgac ucgcugagga uccgaca                                       87

<210> SEQ ID NO 269
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 269
ggaggagcua cgaugcgggg aagcaacacu uagucgcgau ugauaugugc gcagucauca    60
gacagacgac ucgcugagga uccgaca                                       87

<210> SEQ ID NO 270
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 270
ggaggagcua cgaugcgggg aagcaacacu uagucgcgau ugauacgugc guagucauca    60
gacagacgac ucgcugagga uccgaca                                       87

<210> SEQ ID NO 271
<211> LENGTH: 87
<212> TYPE: DNA
<213> ORGANISM: Artificial Sequence
<220> FEATURE:
<223> OTHER INFORMATION: Synthetic Polynucleotide
```

<400> SEQUENCE: 271
ggaggagcua cgaugcgggg aagcaacacu uagucgcgau gguacgugc gcagucauca    60 gacagacgac ucgcugagga uccgaca    87

<210> SEQ ID NO 272
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 272
ggaggagcua cgaugcgggg aagcaacacu uagucgcgau ugauacgugc gcggucauca    60
gacagacgac ucgcugagga uccgaca    87

<210> SEQ ID NO 273
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 273
ggaggagcua cgaugcgggg aagcaacgcu uagucgcgau ugauacgugc gcagucauca    60
gacagacgac ucgcugagga uccgaca    87

<210> SEQ ID NO 274
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 274
ggaggagcua cgaugcggua auucucagga ggugcggaac gggauauggu uuguucgcca    60
gucagacgac ucgcugagga uccgaca    87

<210> SEQ ID NO 275
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 275
ggaggagcua cgaugcggua auucucagga ggugcggaac gggauaugga uuguccgcca    60
gucagacgac ucgcugagga uccgaca    87

<210> SEQ ID NO 276
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 276
ggaggagcua cgaugcggua auucucagga ggugcggaac gggauaugga auguucgcca    60
gucagacgac ucgcugagga uccgaca    87

<210> SEQ ID NO 277

```
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 277
ggaggagcua cgaugcggua auucucagga ggugcggagc gggauaugga uuguucgcca    60
gucagacgac ucgcugagga uccgaca                                       87

<210> SEQ ID NO 278
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 278
ggaggagcua cgaugcggac caucgcuccc gcguauugcg aacgcaucgu uauuuagccg    60
ucagacgacu cgcugaggau ccgaca                                        86

<210> SEQ ID NO 279
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 279
ggaggagcua cgaugcggcc caucacuccc gcguauugcg uacgcaucgu uauuuagccg    60
ucagacgacu cgcugaggau ccgaca                                        86

<210> SEQ ID NO 280
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 280
ggaggagcua cgaugcggcc ggaggcaguc acuaaucuuc acuucccuua gacaugcgca    60
gacagacgac ucgcugagga uccgaca                                       87

<210> SEQ ID NO 281
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 281
ggaggagcua cgaugcgggg aagcaacacu uagucgcgau ugauacgugu gcagucauca    60
gacagacgac ucgcugagga uccgaca                                       87

<210> SEQ ID NO 282
<211> LENGTH: 87
<212> TYPE: DNA
<213> ORGANISM: Artificial Sequence
<220> FEATURE:
<223> OTHER INFORMATION: Synthetic Polynucleotide
```

```
<400> SEQUENCE: 282
ggaggagcua cgaugcgggg aagcaacauu uagucgcgau ugauacgugc gcagucauca      60
gacagacgac ucgcugagga uccgaca                                         87

<210> SEQ ID NO 283
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 283
ggaggagcua cgaugcgggg aggcaacacu uagucgcgau ugauacgugc gcagucauca      60
gacagacgac ucgcugagga uccgaca                                         87

<210> SEQ ID NO 284
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 284
ggaggagcua cgaugcgggg gagcaacacu uagucgcgau ugauacgugc gcagucauca      60
gacagacgac ucgcugagga uccgaca                                         87

<210> SEQ ID NO 285
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 285
ggaggagcua cgaugcgggg aagcaauacu uagucgcgau ugauacgugc gcagucauca      60
gacagacgac ucgcugagga uccgaca                                         87

<210> SEQ ID NO 286
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 286
ggaggagcua cgaugcgggg aagcaacacu uagucgggau ugauacgugc ccagucauca      60
gacagacgac ucgcugagga uccgaca                                         87

<210> SEQ ID NO 287
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 287
ggaggagcua cgaugcggcc gucucgcucu caucccaugc acgacaccuc ucucacugca      60
cagacgacuc gcugaggauc cgaca                                           85

<210> SEQ ID NO 288
```

```
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 288
ggaggagcua cgaugcggua auucucagga gguacggaac gggauaugga uuguucgcca      60
gucagacgac ucgcugagga uccgaca                                         87

<210> SEQ ID NO 289
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 289
ggaggagcua cgaugcggua auucucagga ggugcggaac gggauaugga ugguucgcca      60
gucagacgac ucgcugagga uccgaca                                         87

<210> SEQ ID NO 290
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 290
ggaggagcua cgaugcggua auucucagga ggugcggaac gggauauggg uuguucgcca      60
uacagacgac ucgcugagga uccgaca                                         87

<210> SEQ ID NO 291
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 291
ggaggagcua cgaugcggua auucccagga ggugcggaac gggauaugga uuguucgcca      60
gucagacgac ucgcugagga uccgaca                                         87

<210> SEQ ID NO 292
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 292
ggaggagcua cgaugcggua auucacagga ggugcggaac gggauaugga uuguucgcca      60
gucagacgac ucgcugagga uccgaca                                         87

<210> SEQ ID NO 293
<211> LENGTH: 86
<212> TYPE: DNA
<213> ORGANISM: Artificial Sequence
<220> FEATURE:
<223> OTHER INFORMATION: Synthetic Polynucleotide
```

<400> SEQUENCE: 293
ggaggagcua cgaugcggcc gauugcguca uccuccauac caucgccuua ccguuccgcg    60
ucagacgacu cgcugaggau ccgaca                                         86

<210> SEQ ID NO 294
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 294
ggaggagcua cgaugcggcc caucacucac gcguagugcg aacgcaucgu uauuuagccg    60
ucagacgacu cgcugaggau ccgaca                                         86

<210> SEQ ID NO 295
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 295
ggaggagcua cgaugcggug uacacugauu gccuuggggu uaagagcgac agauccggca    60
gacagacgac ucgcugagga uccgaca                                        87

<210> SEQ ID NO 296
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 296
ggaggagcua cgaugcgggg aagcgacacu uagucgcgau ugauacgugc gcagucauca    60
gacagacgac ucgcugagga uccgaca                                        87

<210> SEQ ID NO 297
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 297
ggaggagcua cgaugcgggg aagcaacacu uagucgggau ugauacgugc ccagucagca    60
gacagacgac ucgcugagga uccgaca                                        87

<210> SEQ ID NO 298
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 298
ggaggagcua cgaugcggua auucucagga ggcgcggaac gggauaugga uuguucgcca    60
gucagacgac ucgcugagga uccgaca                                        87

<210> SEQ ID NO 299

```
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 299
ggaggagcua cgaugcggua auucucagga ggagcggaac gggauaugga uuguucgcca    60
gucagacgac ucgcugagga uccgaca                                        87

<210> SEQ ID NO 300
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 300
ggaggagcua cgaugcggua auucucagga ggugcggaac gggauacgga uuguucgcca    60
gucagacgac ucgcugagga uccgaca                                        87

<210> SEQ ID NO 301
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 301
ggaggagcua cgaugcggua auucucagga ggugcggaac gggauaagga uuguucgcca    60
gucagacgac ucgcugagga uccgaca                                        87

<210> SEQ ID NO 302
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 302
ggaggagcua cgaugcggua auucucagga ggugcggaac gggauaugga uugcucgcca    60
gucagacgac ucgcugagga uccgaca                                        87

<210> SEQ ID NO 303
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 303
ggaggagcua cgaugcggua auucucagga ggugcggaac gggauaugga uuauucgcca    60
gucagacgac ucgcugagga uccgaca                                        87

<210> SEQ ID NO 304
<211> LENGTH: 87
<212> TYPE: DNA
<213> ORGANISM: Artificial Sequence
<220> FEATURE:
<223> OTHER INFORMATION: Synthetic Polynucleotide
```

<400> SEQUENCE: 304
ggaggagcua cgaugcggua auucucagga ggugcggaac gggauaugga uugugcgcca      60
gucagacgac ucgcugagga uccgaca      87

<210> SEQ ID NO 305
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 305
ggaggagcua cgaugcggua auucucagga ggugcggaac gggauaugga uuguacgcca      60
gucagacgac ucgcugagga uccgaca      87

<210> SEQ ID NO 306
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 306
ggaggagcua cgaugcggua auucucagga ggugcggaac gggauaugga uuguucgcaa      60
gucagacgac ucgcugagga uccgaca      87

<210> SEQ ID NO 307
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 307
ggaggagcua cgaugcggua auucucagga ggugcggaau gggauaugga uuguucgcca      60
gucagacgac ucgcugagga uccgaca      87

<210> SEQ ID NO 308
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 308
ggaggagcua cgaugcggua auucgcagga ggugcggaac gggauaugga uuguucgcca      60
gacagacgac ucgcugagga uccgaca      87

<210> SEQ ID NO 309
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 309
ggaggagcua cgaugcggcc caucacuccc gcguauugcg accgcaucgu uauuuagccg      60
ucagacgacu cgcugaggau ccgaca      86

<210> SEQ ID NO 310

<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 310
ggaggagcua cgaugcggau uaccaacuug aacgccgaaa guggggucac guuuuccgca    60
gacagacgac ucgcugagga uccgaca                                       87

<210> SEQ ID NO 311
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 311
ggaggagcua cgaugcgggg aagcaacacu uagucgcgau ugauacgugc gcagucaucg    60
gacagacgac ucgcugagga uccgaca                                       87

<210> SEQ ID NO 312
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 312
ggaggagcua cgaugcggua auucucaggu ggugcggaac gggauaugga uuguucgcca    60
gucagacgac ucgcugagga uccgaca                                       87

<210> SEQ ID NO 313
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 313
ggaggagcua cgaugcggug auucucagga ggugcggaac gggauaugga uuguucgcca    60
gucagacgac ucgcugagga uccgaca                                       87

<210> SEQ ID NO 314
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 314
ggaggagcua cgaugcggua auucucagga ggugcggaac gggauauggg uuguucgcca    60
gucagacgac ucgcugagga uccgaca                                       87

<210> SEQ ID NO 315
<211> LENGTH: 87
<212> TYPE: DNA
<213> ORGANISM: Artificial Sequence
<220> FEATURE:
<223> OTHER INFORMATION: Synthetic Polynucleotide

```
<400> SEQUENCE: 315
ggaggagcua cgaugcggcc caucacuccc gcguauugcg aacgcaucgu uauuuagcca    60
gacagacgac ucgcugagga uccgaca                                        87

<210> SEQ ID NO 316
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 316
ggaggagcua cgaugcggcc caucacucac gcgaauugcg aacgcaucgu uauuuagccg    60
ucagacgacu cgcugaggau ccgaca                                         86

<210> SEQ ID NO 317
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 317
ggaggagcua cgaugcggcg caucacuccc gcguauugcg aacgcaucgu uauuuagccg    60
ucagacgacu cgcugaggau ccgaca                                         86

<210> SEQ ID NO 318
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 318
ggaggagcua cgaugcggau uaccaacuug aacgccgaga guguggucac guguucugca    60
gacagacgac ucgcugagga uccgaca                                        87

<210> SEQ ID NO 319
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 319
ggaggagcua cgaugcggca cauacugaca augguuacca gagcaggucc ggcacaucca    60
gacagacgac ucgcugagga uccgaca                                        87

<210> SEQ ID NO 320
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 320
ggaggagcua cgaugcgguu acgcguuuaa gucauugacg cguuacacug gaggggcca     60 gacagacgac ucgcugagga uccgaca                                        87

<210> SEQ ID NO 321
```

```
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 321
ggaggagcua cgaugcggua cacucaguca cguagcaccg cagugacccu uuguaccgca      60
gacagacgac ucgcugagga uccgaca                                         87

<210> SEQ ID NO 322
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 322
ggaggagcua cgaugcgggg aagcaacacu uagucgugau ugauacgugc gcagucauca      60
gacagacgac ucgcugagga uccgaca                                         87

<210> SEQ ID NO 323
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 323
ggaggagcua cgaugcggua auucucggga ggugcggaac gggauaugga uuguucgcca      60
gucagacgac ucgcugagga uccgaca                                         87

<210> SEQ ID NO 324
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 324
ggaggagcua cgaugcggua auucucagga ggugcagaac gggauaugga uuguucgcca      60
gucagacgac ucgcugagga uccgaca                                         87

<210> SEQ ID NO 325
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 325
ggaggagcua cgaugcggua auucucagga ggugcggaac gggauaugga uuguuggcca      60
gucagacgac ucgcugagga uccgaca                                         87

<210> SEQ ID NO 326
<211> LENGTH: 87
<212> TYPE: DNA
<213> ORGANISM: Artificial Sequence
<220> FEATURE:
<223> OTHER INFORMATION: Synthetic Polynucleotide
```

<400> SEQUENCE: 326
ggaggagcua cgaugcggua auucucagga ggugcggaac gggauaugga uuguuagcca    60
gucagacgac ucgcugagga uccgaca                                        87

<210> SEQ ID NO 327
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 327
ggaggagcua cgaugcggcg gaucacuccc gcguauugcg aacgcaucgu uauuuagccg    60
ucagacgacu cgcugaggau ccgaca                                         86

<210> SEQ ID NO 328
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 328
ggaggagcua cgaugcggcc caucacuccc gcguauugcg aacgcaucgu uauugagccg    60
ucagacgacu cgcugaggau ccgaca                                         86

<210> SEQ ID NO 329
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 329
ggaggagcua cgaugcggcc caucacucgc gcguauugcg aacgcauagu uauuuagccg    60
ucagacgacu cgcugaggau ccgaca                                         86

<210> SEQ ID NO 330
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 330
ggaggagcua cgaugcggca acaaacuaau cagacacgag gcagaaagau agguccggca    60
gacagacgac ucgcugagga uccgaca                                        87

<210> SEQ ID NO 331
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 331
ggaggagcua cgaugcggug uagcgagaau cgcguuguug ggugucugu ugucagacga    60 cucgcugagg auccgaca                                                  78

<210> SEQ ID NO 332

-continued

```
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 332
ggaggagcua cgaugcgggg aagcaacacu uagucgcgau ugauacgugc gcaguuauca      60
gacagacgac ucgcugagga uccgaca                                         87

<210> SEQ ID NO 333
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 333
ggaggagcua cgaugcgggg aagcaacacu uagucgcgau ugauacgugc gcagucauca      60
gacagacgac ucgcugagga uccgaca                                         87

<210> SEQ ID NO 334
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 334
ggaggagcua cgaugcggug aagcaacacu uagucgcgau ugauacgugc gcagucauca      60
gacagacgac ucgcugagga uccgaca                                         87

<210> SEQ ID NO 335
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 335
ggaggagcua cgaugcgggg aagcaacacu uggucgcgau ugauacgugc gcagucauca      60
gacagacgac ucgcugagga uccgaca                                         87

<210> SEQ ID NO 336
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 336
ggaggagcua cgaugcgggg aagcaacacu uagucgcgau ugauacgugc gcagucauca      60
ggcagacgac ucgcugagga uccgaca                                         87

<210> SEQ ID NO 337
<211> LENGTH: 86
<212> TYPE: DNA
<213> ORGANISM: Artificial Sequence
<220> FEATURE:
<223> OTHER INFORMATION: Synthetic Polynucleotide
```

-continued

<400> SEQUENCE: 337
ggaggagcua cgaugcggga agcaacacuu agucgcgauu gauacgugcg cagucaucag    60
acagacgacu cgcugaggau ccgaca                                         86

<210> SEQ ID NO 338
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 338
ggaggagcua cgaugcgggg aagcagcacu uagucgcgau ugauacgugc gcagucauca    60
gacagacgac ucgcugagga uccgaca                                        87

<210> SEQ ID NO 339
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 339
ggaggagcua cgaugcgggg aaguaacacu uagucgcgau ugauacgugc gcagucauca    60
gacagacgac ucgcugagga uccgaca                                        87

<210> SEQ ID NO 340
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 340
ggaggagcua cgaugcggua acucucagga ggugcggaac gggauaugga uuguucgcca    60
gucagacgac ucgcugagga uccgaca                                        87

<210> SEQ ID NO 341
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 341
ggaggagcua cgaugcggua auucucagga gguguggaac gggauaugga uuguucgcca    60
gucagacgac ucgcugagga uccgaca                                        87

<210> SEQ ID NO 342
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 342
ggaggagcua cgaugcggua auucucagga ggugcggaac ggguuaugga uuguucgcca    60
gucagacgac ucgcugagga uccgaca                                        87

<210> SEQ ID NO 343

```
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 343
ggaggagcua cgaugcggua auucucagga ggugcggaac gggauaugga uuguucgcga    60
gucagacgac ucgcugagga uccgaca                                        87

<210> SEQ ID NO 344
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 344
ggaggagcua cgaugcggcc gauuucguca ugcuccauac caucgccuua ccguccgcg     60 ucagacgacu cgcugaggau ccgaca                                         86

<210> SEQ ID NO 345
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 345
ggaggagcua cgaugcggcc caucacucgc gcguauugcg aacgcaucgu uauuuagccg    60
ucagacgacu cgcugaggau ccgaca                                         86

<210> SEQ ID NO 346
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 346
ggaggagcua cgaugcggca ggugcgggau cuaaugcgua gacagccaua uacugacaca    60
gacagacgac ucgcugagga uccgaca                                        87

<210> SEQ ID NO 347
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 347
ggaggagcua cgaugcggca ggggcgggau cuaaugcgua gacagccaua uacugacaca    60
gacagacgac ucgcugagga uccgaca                                        87

<210> SEQ ID NO 348
<211> LENGTH: 87
<212> TYPE: DNA
<213> ORGANISM: Artificial Sequence
<220> FEATURE:
<223> OTHER INFORMATION: Synthetic Polynucleotide
```

<400> SEQUENCE: 348
ggaggagcua cgaugcggcc uaguacaaaa gccugaucuc ugugagcaga cacuagaaca    60
gacagacgac ucgcugagga uccgaca    87

<210> SEQ ID NO 349
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 349
ggaggagcua cgaugcggug uacacugauu gccuuugugu uaugagcgac agaucugcca    60
gacagacgac ucgcugagga uccgaca    87

<210> SEQ ID NO 350
<211> LENGTH: 88
<212> TYPE: DNA
<213> ORGANISM: Artificial Sequence
<220> FEATURE:
<223> OTHER INFORMATION: Synthetic Polynucleotide

<400> SEQUENCE: 350
ggaggagcua cgaugcggca uacacacuug acuuuaggga acgaaccucu agccguggcc    60
agacagacga cucgcugagg auccgaca    88

<210> SEQ ID NO 351
<211> LENGTH: 84
<212> TYPE: DNA
<213> ORGANISM: Artificial Sequence
<220> FEATURE:
<223> OTHER INFORMATION: Synthetic Polynucleotide

<400> SEQUENCE: 351
ggaggagcua cgaugcggac ggaggauagu ugcuaaucga gcccugcuga cgcuucagac    60
agacgacucg cugaggaucc gaca    84

<210> SEQ ID NO 352
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 352
ggaggagcua cgaugcggcc gucucgcucu caucccaugc acgaaaccuc ucucagugca    60
cagacgacuc gcugaggauc cgaca    85

<210> SEQ ID NO 353
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 353
ggaggagcua cgaugcggua auucucaggg ggugcggaac gggauaugga uuguucgcca    60
gucagacgac ucgcugagga uccgaca    87

<210> SEQ ID NO 354

<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 354
ggaggagcua cgaugcggua auucucagga ggugcggaac gggacaugga uuguucgcca    60
gucagacgac ucgcugagga uccgaca                                        87

<210> SEQ ID NO 355
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 355
ggaggagcua cgaugcggua auucucagga ggugcggaac gagauaugga uuguucgcca    60
gucagacgac ucgcugagga uccgaca                                        87

<210> SEQ ID NO 356
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 356
ggaggagcua cgaugcggua auucucagga ggugcggaac gggauaugaa uuguucgcca    60
gucagacgac ucgcugagga uccgaca                                        87

<210> SEQ ID NO 357
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 357
ggaggagcua cgaugcggua auucucagga agugcggaac gggauaugga uuguucgcca    60
gucagacgac ucgcugagga uccgaca                                        87

<210> SEQ ID NO 358
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 358
ggaggagcua cgaugcggcc caucacuccc gcguauggcg aacgcaucgu uauuuagccg    60
ucagacgacu cgcugaggau ccgaca                                         86

<210> SEQ ID NO 359
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 359
ggaggagcua cgaugcgguc auggauucau uacaggaggu gcggugcuau augcacgcca    60
gacagacgac ucgcugagga uccgaca    87

<210> SEQ ID NO 360
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 360
ggaggagcua cgaugcggcc agccacacuu ugaccgaauu ggcaagcgcg ggcaaaucga    60
acagacgacu cgcugaggau ccgaca    86

<210> SEQ ID NO 361
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 361
ggaggagcua cgaugcggcc uaguacaaaa gccugaucuu ugggaaccga cccuaggaca    60
gacagacgac ucgcugagga uccgaca    87

<210> SEQ ID NO 362
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 362
ggaggagcua cgaugcggcu uacagcucac cauuuauggg aggcccggug uuguguucca    60
gacagacgac ucgcugagga uccgaca    87

<210> SEQ ID NO 363
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 363
ggaggagcua cgaugcggau uauuguuuga cguauuccaa gugagauuac gcacgcacca    60
gacagacgac ucgcugagga uccgaca    87

<210> SEQ ID NO 364
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 364
ggaggagcua cgaugcggaa cagcuuaauc gccagucgau acgcgccaua caucaucaca    60
gacagacgac ucgcugagga uccgaca    87

<210> SEQ ID NO 365

```
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 365
ggaggagcua cgaugcggua auucucagga gaugcggaac gggauaugga uuguucgcca      60
gucagacgac ucgcugagga uccgaca                                         87

<210> SEQ ID NO 366
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 366
ggaggagcua cgaugcggua auucucagga ggugcgaaac gggauaugga uuguucgcca      60
gucagacgac ucgcugagga uccgaca                                         87

<210> SEQ ID NO 367
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 367
ggaggagcua cgaugcggac gauuucguca uccuccauac caucgccuua ccguucagcg      60
ucagacgacu cgcugaggau ccgaca                                          86

<210> SEQ ID NO 368
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 368
ggaggagcua cgaugcggca acaaacuaau cagacacgag acagagagau agaucugcca      60
gacagacgac ucgcugagga uccgaca                                         87

<210> SEQ ID NO 369
<211> LENGTH: 92
<212> TYPE: DNA
<213> ORGANISM: Artificial Sequence
<220> FEATURE:
<223> OTHER INFORMATION: Synthetic Polynucleotide

<400> SEQUENCE: 369
ggaggagcua cgaugcgguu augcguuuaa gucauugacg cguuacacug gaggggcca       60 gacgacucag acgacucgcu gaggauccga ca                                   92

<210> SEQ ID NO 370
<211> LENGTH: 84
<212> TYPE: DNA
<213> ORGANISM: Artificial Sequence
<220> FEATURE:
<223> OTHER INFORMATION: Synthetic Polynucleotide
```

<400> SEQUENCE: 370
ggaggagcua cgaugcggac ggaggauagu ugcuaaucga gcccugcgga cgcuucagac    60
agacgacucg cugaggaucc gaca    84

<210> SEQ ID NO 371
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 371
ggaggagcua cgaugcggcu uacagcucac cauuuuuggg aggcccggug uuguguucca    60
gacagacgac ucgcugagga uccgaca    87

<210> SEQ ID NO 372
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 372
ggaggagcua cgaugcggac ggaaggauag uugcuaaucg agcccugccg acgcuucaga    60
cagacgacuc gcugaggauc cgaca    85

<210> SEQ ID NO 373
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 373
ggaggagcua cgaugcggua auucucagga ggugcggaac gggauauaga uuguucgcca    60
gucagacgac ucgcugagga uccgaca    87

<210> SEQ ID NO 374
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 374
ggaggagcua cgaugcggua auucucagaa ggugcggaac gggauaugga uuguucgcca    60
gucagacgac ucgcugagga uccgaca    87

<210> SEQ ID NO 375
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 375
ggaggagcua cgaugcggua auucucagga ggugcggaac gggauaugga uuguucgccc    60
gucagacgac ucgcugagga uccgaca    87

<210> SEQ ID NO 376

<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 376
ggaggagcua cgaugcggua auucucaaga ggugcggaac gggauaugga uuguucgcca    60
gucagacgac ucgcugagga uccgaca                                       87

<210> SEQ ID NO 377
<211> LENGTH: 88
<212> TYPE: DNA
<213> ORGANISM: Artificial Sequence
<220> FEATURE:
<223> OTHER INFORMATION: Synthetic Polynucleotide

<400> SEQUENCE: 377
ggaggagcua cgaugcggca aaaacugaua aacacagguc cggcauuuga gcguacaccc    60
agacagacga cucgcugagg auccgaca                                      88

<210> SEQ ID NO 378
<211> LENGTH: 84
<212> TYPE: DNA
<213> ORGANISM: Artificial Sequence
<220> FEATURE:
<223> OTHER INFORMATION: Synthetic Polynucleotide

<400> SEQUENCE: 378
ggaggagcua cgaugcgguc ggaggauagu ugcuaaucga gcccugccga cgcuucagac    60
agacgacucg cugaggaucc gaca                                          84

<210> SEQ ID NO 379
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 379
ggaggagcua cgaugcgguu augcguuuaa gucauugacg cguuacacug gaggggcca     60 gacagacgac ucgcugagga uccgaca                                       87

<210> SEQ ID NO 380
<211> LENGTH: 89
<212> TYPE: DNA
<213> ORGANISM: Artificial Sequence
<220> FEATURE:
<223> OTHER INFORMATION: Synthetic Polynucleotide

<400> SEQUENCE: 380
ggaggagcua cgaugcggca aaaaacugau aaacacaggu ccggcauuug agcguacacc    60
cagacagacg acucgcugag gauccgaca                                     89

<210> SEQ ID NO 381
<211> LENGTH: 84
<212> TYPE: DNA
<213> ORGANISM: Artificial Sequence
<220> FEATURE:
<223> OTHER INFORMATION: Synthetic Polynucleotide

<400> SEQUENCE: 381
ggaggagcua cgaugcggac ggaggauagu ugcuaaucga gcccugccga cgcuucagac    60
agacgacucg cugaggaucc gaca                                          84

<210> SEQ ID NO 382
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 382
uagcugaagu ucaucucucu u                                             21

<210> SEQ ID NO 383
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 383
uuucagccuu aaggaugguu u                                             21

<210> SEQ ID NO 384
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 384
uuuauucucc ccuuggugu u                                              21

<210> SEQ ID NO 385
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 385
uacucccucu gccuaugugu u                                             21

<210> SEQ ID NO 386
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 386
uuuacuguuu uggcugggcu u                                             21

<210> SEQ ID NO 387
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 387
aaaaugcugg ucauacccuu u                                             21

```
<210> SEQ ID NO 388
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 388
uuguucaaac uacucccucu u                                              21

<210> SEQ ID NO 389
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 389
uuuuccugcc uuccgcuaau u                                              21

<210> SEQ ID NO 390
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 390
uuacagggua auguggugau u                                              21

<210> SEQ ID NO 391
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 391
gauugggagg ugaagggaau u                                              21

<210> SEQ ID NO 392
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 392
aaugcugguc auacccuggu u                                              21

<210> SEQ ID NO 393
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 393
uacaagauau gauccucccu u                                              21

<210> SEQ ID NO 394
<211> LENGTH: 21
<212> TYPE: DNA
<213> ORGANISM: Artificial Sequence
<220> FEATURE:
<223> OTHER INFORMATION: Synthetic Polynucleotide
```

<400> SEQUENCE: 394
uuuaucagaa aggcgucccu u                                            21

<210> SEQ ID NO 395
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 395
uuaaggcugc ggaagccuau u                                            21

<210> SEQ ID NO 396
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 396
uugaccucaa gugauccgcu u                                            21

<210> SEQ ID NO 397
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 397
gacuuccuca aaguuccucu u                                            21

<210> SEQ ID NO 398
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 398
uaaggcugcg gaagccuauu u                                            21

<210> SEQ ID NO 399
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 399
uaaaaaguca gcagcagacu u                                            21

<210> SEQ ID NO 400
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 400
aagucagcag cagacccauu u                                            21

<210> SEQ ID NO 401

```
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 401
gugaggguua agaaagcccu u                                              21

<210> SEQ ID NO 402
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 402
cugcaguuca aaauacugcu u                                              21

<210> SEQ ID NO 403
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 403
uuuggguuag ugaaugggcu u                                              21

<210> SEQ ID NO 404
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 404
uuuacuuaag uauuaucccu u                                              21

<210> SEQ ID NO 405
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 405
gaagccuauu cuaggugagu u                                              21

<210> SEQ ID NO 406
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 406
aaagucagca gcagacccau u                                              21

<210> SEQ ID NO 407
<211> LENGTH: 21
<212> TYPE: DNA
<213> ORGANISM: Artificial Sequence
<220> FEATURE:
<223> OTHER INFORMATION: Synthetic Polynucleotide
```

-continued

<400> SEQUENCE: 407
aaaagucagc agcagacccu u					21

<210> SEQ ID NO 408
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 408
ugaggguuaa gaaagcccuu u					21

<210> SEQ ID NO 409
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 409
cuaggugcuc ucuuuucucu u					21

<210> SEQ ID NO 410
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 410
cuuuggguua gugaaugggu u					21

<210> SEQ ID NO 411
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 411
ugacuuccuc aaaguuccuu u					21

<210> SEQ ID NO 412
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 412
uuccucaaag uuccucgacu u					21

<210> SEQ ID NO 413
<211> LENGTH: 82
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (26)..(65)
<223> OTHER INFORMATION: n is a, c, g, t or u

<400> SEQUENCE: 413
tctcggatcc tcagcgagtc gtctgnnnnn nnnnnnnnnn nnnnnnnnnn     60
nnnnnccgca tcgtcctccc ta                                   82

<210> SEQ ID NO 414
<211> LENGTH: 501
<212> TYPE: PRT
<213> ORGANISM: Artificial Sequence
<220> FEATURE:
<223> OTHER INFORMATION: Synthetic Polypeptide

<400> SEQUENCE: 414

Met Gln Val Cys Ser Gln Pro Gln Arg Gly Cys Val Arg Glu Gln Ser
1               5                   10                  15

Ala Ile Asn Thr Ala Pro Pro Ser Ala His Asn Ala Ala Ser Pro Gly
            20                  25                  30

Gly Ala Arg Gly His Arg Val Pro Leu Thr Glu Ala Cys Lys Asp Ser
        35                  40                  45

Arg Ile Gly Gly Met Met Lys Thr Leu Leu Leu Phe Val Gly Leu Leu
    50                  55                  60

Leu Thr Trp Glu Ser Gly Gln Val Leu Gly Asp Gln Thr Val Ser Asp
65                  70                  75                  80

Asn Glu Leu Gln Glu Met Ser Asn Gln Gly Ser Lys Tyr Val Asn Lys
                85                  90                  95

Glu Ile Gln Asn Ala Val Asn Gly Val Lys Gln Ile Lys Thr Leu Ile
            100                 105                 110

Glu Lys Thr Asn Glu Glu Arg Lys Thr Leu Leu Ser Asn Leu Glu Glu
        115                 120                 125

Ala Lys Lys Lys Lys Glu Asp Ala Leu Asn Glu Thr Arg Glu Ser Glu
    130                 135                 140

Thr Lys Leu Lys Glu Leu Pro Gly Val Cys Asn Glu Thr Met Met Ala
145                 150                 155                 160

Leu Trp Glu Glu Cys Lys Pro Cys Leu Lys Gln Thr Cys Met Lys Phe
                165                 170                 175

Tyr Ala Arg Val Cys Arg Ser Gly Ser Gly Leu Val Gly Arg Gln Leu
            180                 185                 190

Glu Glu Phe Leu Asn Gln Ser Ser Pro Phe Tyr Phe Trp Met Asn Gly
        195                 200                 205

Asp Arg Ile Asp Ser Leu Leu Glu Asn Asp Arg Gln Gln Thr His Met
    210                 215                 220

Leu Asp Val Met Gln Asp His Phe Ser Arg Ala Ser Ser Ile Ile Asp
225                 230                 235                 240

Glu Leu Phe Gln Asp Arg Phe Phe Thr Arg Glu Pro Gln Asp Thr Tyr
                245                 250                 255

His Tyr Leu Pro Phe Ser Leu Pro His Arg Arg Pro His Phe Phe Phe
            260                 265                 270

Pro Lys Ser Arg Ile Val Arg Ser Leu Met Pro Phe Ser Pro Tyr Glu
        275                 280                 285

Pro Leu Asn Phe His Ala Met Phe Gln Pro Phe Leu Glu Met Ile His
    290                 295                 300

Glu Ala Gln Gln Ala Met Asp Ile His Phe His Ser Pro Ala Phe Gln
305                 310                 315                 320

His Pro Pro Thr Glu Phe Ile Arg Glu Gly Asp Asp Arg Thr Val
                325                 330                 335

```
Cys Arg Glu Ile Arg His Asn Ser Thr Gly Cys Leu Arg Met Lys Asp
            340             345                 350

Gln Cys Asp Lys Cys Arg Glu Ile Leu Ser Val Asp Cys Ser Thr Asn
            355             360                 365

Asn Pro Ser Gln Ala Lys Leu Arg Arg Glu Leu Asp Glu Ser Leu Gln
    370             375             380

Val Ala Glu Arg Leu Thr Arg Lys Tyr Asn Glu Leu Leu Lys Ser Tyr
385             390             395                 400

Gln Trp Lys Met Leu Asn Thr Ser Ser Leu Leu Glu Gln Leu Asn Glu
            405             410                 415

Gln Phe Asn Trp Val Ser Arg Leu Ala Asn Leu Thr Gln Gly Glu Asp
            420             425                 430

Gln Tyr Tyr Leu Arg Val Thr Thr Val Ala Ser His Thr Ser Asp Ser
            435             440                 445

Asp Val Pro Ser Gly Val Thr Glu Val Val Lys Leu Phe Asp Ser
            450             455             460

Asp Pro Ile Thr Val Thr Val Pro Val Glu Val Ser Arg Lys Asn Pro
465             470             475                 480

Lys Phe Met Glu Thr Val Ala Glu Lys Ala Leu Gln Glu Tyr Arg Lys
            485             490                 495

Lys His Arg Glu Glu
            500

<210> SEQ ID NO 415
<211> LENGTH: 103
<212> TYPE: DNA
<213> ORGANISM: Artificial Sequence
<220> FEATURE:
<223> OTHER INFORMATION: Synthetic Polynucleotide

<400> SEQUENCE: 415
gaggacgaug cggauuacca acuugaacgc cgagagugug gucacguguu cugcaggacg    60
acucgcugag gauccgagac ccaattctga gatgtgtaaa gat                     103

<210> SEQ ID NO 416
<211> LENGTH: 21
<212> TYPE: DNA
<213> ORGANISM: Artificial Seugence
<220> FEATURE:
<223> OTHER INFORMATION: Synthetic Polynucleotide

<400> SEQUENCE: 416
uuaagacucu acacauuucu a                                              21
```